US007186407B2

(12) United States Patent
Whitehouse

(10) Patent No.: US 7,186,407 B2
(45) Date of Patent: Mar. 6, 2007

(54) METHODS AND COMPOSITIONS FOR THE TREATMENT OF PERIPHERAL ARTERY DISEASE

(75) Inventor: Martha Jo Whitehouse, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 10/845,911

(22) Filed: May 14, 2004

(65) Prior Publication Data

US 2004/0209817 A1 Oct. 21, 2004

Related U.S. Application Data

(63) Continuation of application No. 09/886,856, filed on Jun. 21, 2001, now abandoned.

(60) Provisional application No. 60/276,549, filed on Mar. 16, 2001, provisional application No. 60/264,572, filed on Jan. 26, 2001, provisional application No. 60/213,504, filed on Jun. 22, 2000.

(51) Int. Cl.
*A61K 31/00* (2006.01)
*A61K 38/00* (2006.01)
*A61K 38/16* (2006.01)
*A61K 45/00* (2006.01)

(52) U.S. Cl. ............... 424/85.1; 424/184.1; 424/185.1; 424/198.1; 514/2; 514/12

(58) Field of Classification Search ................... 514/2, 514/12
See application file for complete search history.

(56) References Cited

U.S. PATENT DOCUMENTS

| 5,604,293 | A | 2/1997 | Fiddes et al. |
| 5,792,453 | A | 8/1998 | Hammond et al. |
| 5,852,177 | A | 12/1998 | Senoo et al. |
| 5,879,713 | A | 3/1999 | Roth et al. |
| 5,941,868 | A | 8/1999 | Kaplan et al. |
| 6,440,934 | B1 | 8/2002 | Whitehouse |
| 6,451,303 | B1 * | 9/2002 | Whitehouse et al. ...... 424/85.1 |

OTHER PUBLICATIONS

Hiatt et al. (Oct. 1994) Superiority of treadmill walking excercise versus strength training for patients with peripheral arterial disease, Implications for the mechanism of the training response, Circulation 90(4): 1866-74.*
American Heart Association website downloaded Jan. 13, 2005.*
Baffour, R., et al., "Enhanced Angiogensis and Growth of Collaterals by *In Vivo* Administration of Recombinant Basic Fibroblast Growth Factor in a Rabbit Model of Acute Lower Limb Ischemia: Dose-Response Effect of Basic Fibroblast Growth Factor," *Journal of Vascular Surgery*, Aug. 1992, pp. 181-191, vol. 16(2).
Baumgartner, I., and J.M. Isner, "Stimulation of Peripheral Angiogenesis by Vascular Endothelial Growth Factor (VEGF)," *VASA*, Nov. 1998, pp. 201-206, vol. 27(4).
Cooke, J.P., et al., "Fibroblast Growth Factor as Therapy for Critical Limb Ischemia: A Case Report," *Vascular Medicine*, 1999, pp. 89-91, vol. 4.
Fisher, R.K., and P.L. Harris, "Epidemiological and Economic Considerations in the Critically Ischemic Limb," *Critical Limb Ischemia*, Jul. 1999, pp. 19-25, Futura Publishing Co., New York.
Gerwins, P., et al., "Function of Fibroblast Growth Factors and Vascular Endothelial Growth Factors and Their Receptors in Angiogenesis," *Critical Reviews in Oncology/Hematology*, 2000, pp. 185-194, vol. 34(3), Elsevier Science Publishers Ltd., Ireland.
Hiatt, W.R., et al., "Clinical Trials for Claudication—Assessment of Exercise Performance, Functional Status, and Clinical End Points," *Circulation*, Aug. 1, 1995, pp. 614-621, vol. 92(3).
Lazarous, D.F., et al., "Basic Fibroblast Growth Factor in Patients with Intermittent Claudication: Results of a Phase I Trial," *Journal of the American College of Cardiology*, Oct. 2000, pp. 1239-1244, vol. 36(4), Elsevier Science Inc.
Moyer, et al:, "bFGF: A Potential Therapeutic Agent for the Treatment of Acute Neurodegenerative and Vascular Insufficiency," *Expert Opinion on TherapeuticPatients*, 1998, pp. 1425-1446, vol. 8 (11).
Pantley, G.A., and J.M. Porter, "Therapeutic Angiogenesis: Time for the Next Phase," *Journal of the American College of Cardiology*, Oct. 2000, pp. 1245-1247, vol. 36(4), Elsevier Science Inc.
Regensteiner, J.G., et al., "Evaluation of Walking Impairment by Questionnaire in Patients wtih Peripheral Arterial Disease," *Journal of Vascular Medicine and Biology*, Jun. 1990, pp. 142-152, vol. 2(3).
Santilli, J.D., and S.M. Santilli, "Chronic Critical Limb Ischemia: Diagnosis, Treatment and Prognosis," *American Family Physician*, Apr. 1, 1999, pp. 1899-1908, vol. 59(7).
Weitz, J.I. et al., "Diagnosis and Treatment of Chronic Arterial Insufficiency of the Lower Extremities: A Critical Review," *Circulation*, 1996, pp. 3026-3049, vol. 94.
Yang, H.T. et al., "Basic Fibroblast Growth Factor Increases Collateral Blood Flow in Rats with Femoral Arterial Ligation, " *Circulation Research*, Jul. 1996, pp. 62-69, vol. 79(1).

(Continued)

*Primary Examiner*—Brenda Brumback
*Assistant Examiner*—Daniel Gamett
(74) *Attorney, Agent, or Firm*—Lisa E. Alexander; Leslie Henry; Alisa A. Harbin

(57) ABSTRACT

Compositions and methods for treating peripheral artery disease in a patient are provided. Compositions comprise recombinant fibroblast growth factor-2. Fibroblast growth factor, such as FGF-2, is administered in therapeutically effective amounts to treat or prevent peripheral artery disease including claudication and critical limb ischemia. Pharmaceutical compositions comprising a therapeutically effective amount of FGF-2 and a pharmaceutically acceptable carrier are also provided. The methods of the invention to treat peripheral artery disease and claudication comprise administering at least a single dose of a pharmaceutical composition comprising the FGF, such as FGF-2, via intra-arterial, intravenous, or intramuscular infusion to the patient. It is recognized that increased benefits may result from multiple dosing, including intermittent dosing.

77 Claims, 20 Drawing Sheets

OTHER PUBLICATIONS

Yang, H.T., and Y. Feng, "bFGF Increase Collateral Blood Flow in Aged Rats with Femoral Artery Ligation," *Am. J. Physiol. Heart Circ. Physiol.*, 2000, pp. H85-H93, vol. 278, American Physiological Society, USA.

Yang, H.T., et al., "Efficacy and Specificity of bFGF Increased Collateral Flow in Experimental Peripheral Arterial Insufficiency," *Am. J. Physiol. Heart Circ. Physiol.*, 2000, pp. H1966-H1973, vol. 278, American Physiological Society, USA.

Yang, H.T., et al., "Exercise Training Enhances Basic Fibroblast Growth Factor-Induced Collateral Blood Flow,"*Am. J. Physiol. Heart Circ. Physiol.*, 1998, pp. H2053-H2061, vol. 274, American Physiological Society, USA.

Lazarous, D.F., et al., "Effect of Basic Fibroblast Growth Factor on Lower Extremity Blood Flow in Patients with Intermittent Claudication: Preliminary Results," *Supplement to Circulation*, Abstracts from the 71st *Scientific Sessions*, Oct. 27, 1998, p. I-456, Abstract No. 2398, vol. 98(17), Supplement I.

\* cited by examiner

| | |
|---|---|
| cca gcc cta cca gaa gat ggg ggg tcc ggg gcc ttc cca cca ggg cac<br>Pro Ala Leu Pro Glu Asp Gly Gly Ser Gly Ala Phe Pro Pro Gly His<br>1                   5                       10                       15 | 48 |
| ttc aaa gat cca aaa cga cta tat tgt aaa aac ggg ggg ttc ttc cta<br>Phe Lys Asp Pro Lys Arg Leu Tyr Cys Lys Asn Gly Gly Phe Phe Leu<br>                   20                      25                       30 | 96 |
| cga atc cac cca gat ggg cga gta gat ggg gta cga gaa aaa tcc gat<br>Arg Ile His Pro Asp Gly Arg Val Asp Gly Val Arg Glu Lys Ser Asp<br>        35                              40                          45 | 144 |
| cca cac atc aaa cta caa cta caa gcc gaa gaa cga ggg gta gta tcc<br>Pro His Ile Lys Leu Gln Leu Gln Ala Glu Glu Arg Gly Val Val Ser<br>      50                      55                       60 | 192 |
| atc aaa ggg gta tgt gcc aac cga tat cta gcc atg aaa gaa gat ggg<br>Ile Lys Gly Val Cys Ala Asn Arg Tyr Leu Ala Met Lys Glu Asp Gly<br>65                        70                         75                   80 | 240 |
| cga cta cta gcc tcc aaa tgt gta acc gat gaa tgt ttc ttc ttc gaa<br>Arg Leu Leu Ala Ser Lys Cys Val Thr Asp Glu Cys Phe Phe Phe Glu<br>                        85                     90                       95 | 288 |
| cga cta gaa tcc aac aac tat aac acc tat cga tcc cga aaa tat tcc<br>Arg Leu Glu Ser Asn Asn Tyr Asn Thr Tyr Arg Ser Arg Lys Tyr Ser<br>              100                     105                     110 | 336 |
| tcc tgg tat gta gcc cta aaa cga acc ggg caa tat aaa cta ggg cca<br>Ser Trp Tyr Val Ala Leu Lys Arg Thr Gly Gln Tyr Lys Leu Gly Pro<br>        115                     120                     125 | 384 |
| aaa acc ggg cca ggg caa aaa gcc atc cta ttc cta cca atg tcc gcc<br>Lys Thr Gly Pro Gly Gln Lys Ala Ile Leu Phe Leu Pro Met Ser Ala<br>        130                     135                     140 | 432 |
| aaa tcc taa<br>Lys Ser *<br>145 | 441 |

FIG. 1.

Pro Ala Leu Pro Glu Asp Gly Gly Ser Gly Ala Phe Pro Pro Gly His
1              5                    10                   15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Ser
            100                 105                 110

Ser Trp Tyr Val Ala Leu Lys Arg Thr Gly Gln Tyr Lys Leu Gly Pro
        115                 120                 125

Lys Thr Gly Pro Gly Gln Lys Ala Ile Leu Phe Leu Pro Met Ser Ala
        130                 135                 140

Lys Ser
145

FIG. 2.

```
ccc gcc ttg ccc gag gat ggc ggc agc ggc gcc ttc ccg ccc ggc cac    48
Pro Ala Leu Pro Glu Asp Gly Gly Ser Gly Ala Phe Pro Pro Gly His
 1               5                  10                 15 ttc aag gac ccc aag cgg ctg tac tgc aaa aac ggg ggc ttc ttc ctg    96
Phe Lys Asp Pro Lys Arg Leu Tyr Cys Lys Asn Gly Gly Phe Phe Leu
                20                  25                 30 cgc atc cac ccc gac ggc cga gtt gac ggg gtc cgg gag aag agc gac   144
Arg Ile His Pro Asp Gly Arg Val Asp Gly Val Arg Glu Lys Ser Asp
            35                  40                 45 cct cac atc aag cta caa ctt caa gca gaa gag aga gga gtt gtg tct   192
Pro His Ile Lys Leu Gln Leu Gln Ala Glu Glu Arg Gly Val Val Ser
        50                  55                 60 atc aaa gga gtg tgt gct aac cgt tac ctg gct atg aag gaa gat gga   240
Ile Lys Gly Val Cys Ala Asn Arg Tyr Leu Ala Met Lys Glu Asp Gly
 65                 70                 75                 80 aga tta ctg gct tct aaa tgt gtt acg gat gag tgt ttc ttt gaa      288
Arg Leu Leu Ala Ser Lys Cys Val Thr Asp Glu Cys Phe Phe Phe Glu
                85                  90                 95 cga ttg gaa tct aat aac tac aat act tac cgg tca agg aaa tac acc   336
Arg Leu Glu Ser Asn Asn Tyr Asn Thr Tyr Arg Ser Arg Lys Tyr Thr
            100                 105                110 agt tgg tat gtg gca ctg aaa cga act ggg cag tat aaa ctt gga tcc   384
Ser Trp Tyr Val Ala Leu Lys Arg Thr Gly Gln Tyr Lys Leu Gly Ser
        115                 120                125 aaa aca gga cct ggg cag aaa gct ata ctt ttt ctt cca atg tct gct   432
Lys Thr Gly Pro Gly Gln Lys Ala Ile Leu Phe Leu Pro Met Ser Ala
    130                 135                140 aag agc tga                                                      441
Lys Ser  *
145
```

FIG. 3.

```
atg gca gcc ggg agc atc acc acg ctg cca gcc cta cca gaa gat ggg    48
Met Ala Ala Gly Ser Ile Thr Thr Leu Pro Ala Leu Pro Glu Asp Gly
 1               5                  10                  15 ggg tcc ggg gcc ttc cca cca ggg cac ttc aaa gat cca aaa cga cta    96
Gly Ser Gly Ala Phe Pro Pro Gly His Phe Lys Asp Pro Lys Arg Leu
                 20                  25                  30 tat tgt aaa aac ggg ggg ttc ttc cta cga atc cac cca gat ggg cga    144
Tyr Cys Lys Asn Gly Gly Phe Phe Leu Arg Ile His Pro Asp Gly Arg
         35                  40                  45 gta gat ggg gta cga gaa aaa tcc gat cca cac atc aaa cta caa cta    192
Val Asp Gly Val Arg Glu Lys Ser Asp Pro His Ile Lys Leu Gln Leu
     50                  55                  60 caa gcc gaa gaa cga ggg gta gta tcc atc aaa ggg gta tgt gcc aac    240
Gln Ala Glu Glu Arg Gly Val Val Ser Ile Lys Gly Val Cys Ala Asn
 65                  70                  75                  80 cga tat cta gcc atg aaa gaa gat ggg cga cta cta gcc tcc aaa tgt    288
Arg Tyr Leu Ala Met Lys Glu Asp Gly Arg Leu Leu Ala Ser Lys Cys
                 85                  90                  95 gta acc gat gaa tgt ttc ttc ttc gaa cga cta gaa tcc aac aac tat    336
Val Thr Asp Glu Cys Phe Phe Phe Glu Arg Leu Glu Ser Asn Asn Tyr
            100                 105                 110 aac acc tat cga tcc cga aaa tat tcc tcc tgg tat gta gcc cta aaa    384
Asn Thr Tyr Arg Ser Arg Lys Tyr Ser Ser Trp Tyr Val Ala Leu Lys
        115                 120                 125 cga acc ggg caa tat aaa cta ggg cca aaa acc ggg cca ggg caa aaa    432
Arg Thr Gly Gln Tyr Lys Leu Gly Pro Lys Thr Gly Pro Gly Gln Lys
    130                 135                 140 gcc atc cta ttc cta cca atg tcc gcc aaa tcc taa                    468
Ala Ile Leu Phe Leu Pro Met Ser Ala Lys Ser  *
145                 150                 155
```

FIG. 4.

| | |
|---|---|
| atg gca gcc ggg agc atc acc acg ctg ccc gcc ttg ccc gag gat ggc<br>Met Ala Ala Gly Ser Ile Thr Thr Leu Pro Ala Leu Pro Glu Asp Gly<br>1               5                  10              15 | 48 |
| ggc agc ggc gcc ttc ccg ccc ggc cac ttc aag gac ccc aag cgg ctg<br>Gly Ser Gly Ala Phe Pro Pro Gly His Phe Lys Asp Pro Lys Arg Leu<br>             20                  25              30 | 96 |
| tac tgc aaa aac ggg ggc ttc ttc ctg cgc atc cac ccc gac ggc cga<br>Tyr Cys Lys Asn Gly Gly Phe Phe Leu Arg Ile His Pro Asp Gly Arg<br>         35                  40              45 | 144 |
| gtt gac ggg gtc cgg gag aag agc gac cct cac atc aag cta caa ctt<br>Val Asp Gly Val Arg Glu Lys Ser Asp Pro His Ile Lys Leu Gln Leu<br>    50                  55                  60 | 192 |
| caa gca gaa gag aga gga gtt gtg tct atc aaa gga gtg tgt gct aac<br>Gln Ala Glu Glu Arg Gly Val Val Ser Ile Lys Gly Val Cys Ala Asn<br>65                70                75              80 | 240 |
| cgt tac ctg gct atg aag gaa gat gga aga tta ctg gct tct aaa tgt<br>Arg Tyr Leu Ala Met Lys Glu Asp Gly Arg Leu Leu Ala Ser Lys Cys<br>             85                  90              95 | 288 |
| gtt acg gat gag tgt ttc ttt ttt gaa cga ttg gaa tct aat aac tac<br>Val Thr Asp Glu Cys Phe Phe Phe Glu Arg Leu Glu Ser Asn Asn Tyr<br>              100                105             110 | 336 |
| aat act tac cgg tca agg aaa tac acc agt tgg tat gtg gca ctg aaa<br>Asn Thr Tyr Arg Ser Arg Lys Tyr Thr Ser Trp Tyr Val Ala Leu Lys<br>      115                120              125 | 384 |
| cga act ggg cag tat aaa ctt gga tcc aaa aca gga cct ggg cag aaa<br>Arg Thr Gly Gln Tyr Lys Leu Gly Ser Lys Thr Gly Pro Gly Gln Lys<br>    130                135              140 | 432 |
| gct ata ctt ttt ctt cca atg tct gct aag agc tga ttttaa<br>Ala Ile Leu Phe Leu Pro Met Ser Ala Lys Ser *<br>145               150              155 | 474 |

FIG. 5.

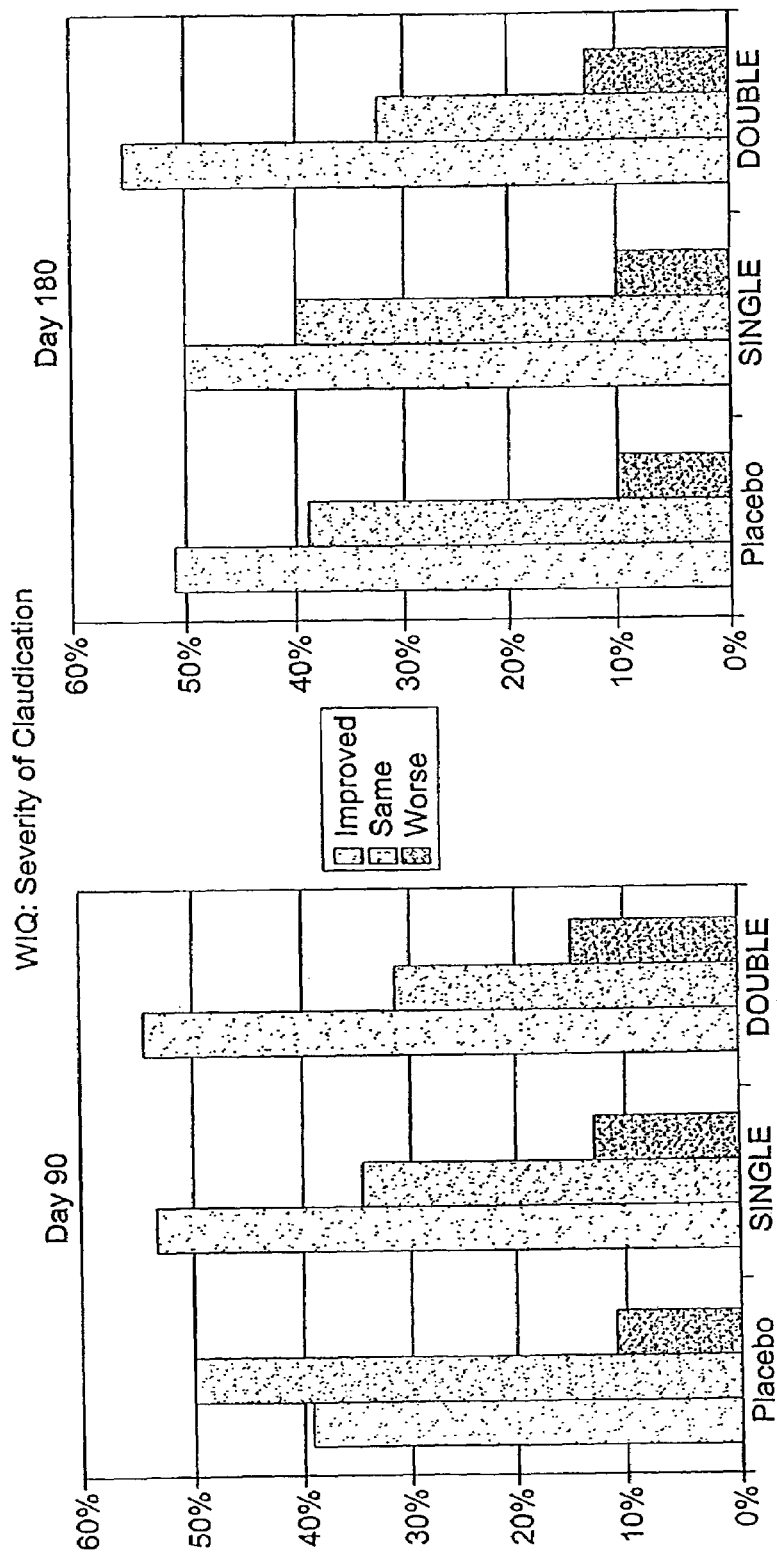
FIG. 10.B.
FIG. 10.A.

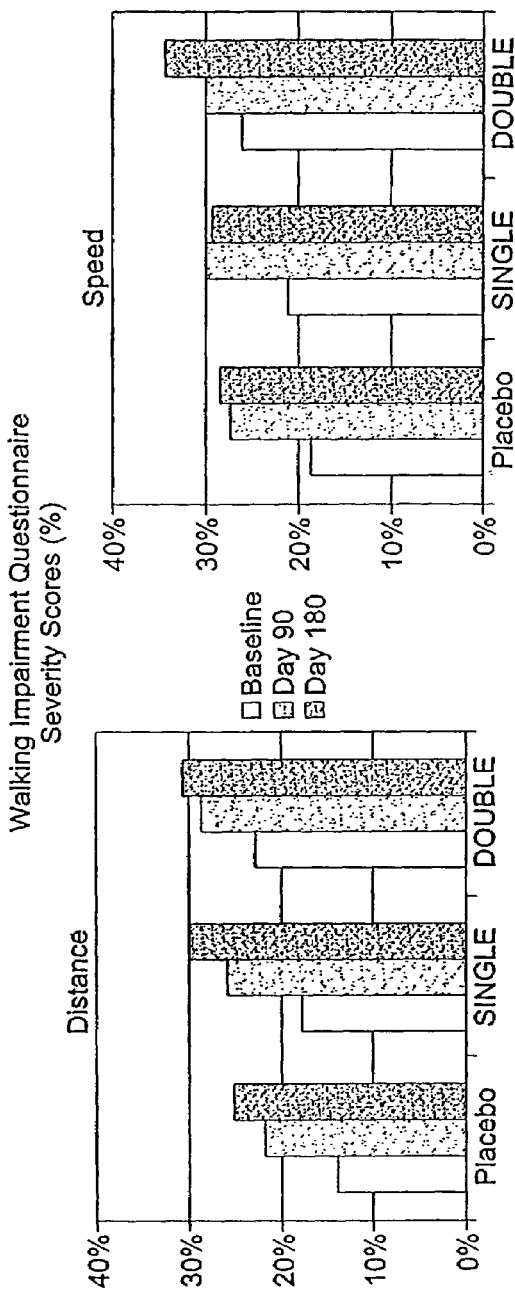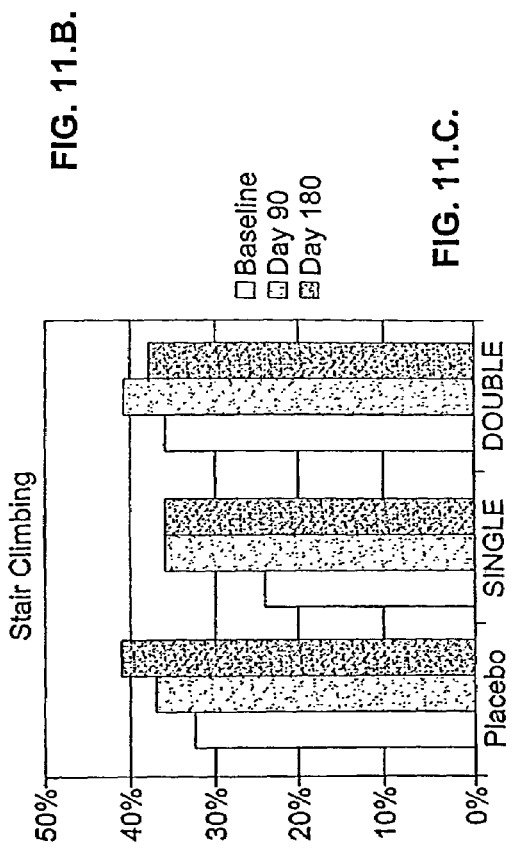
FIG. 11.A.
FIG. 11.B.
FIG. 11.C.

All PAD: Summary of Results

| VARIABLE | Day 90 | Day 180 |
|---|---|---|
| PWT - primary overall | ++ | |
| PWT: pairwise/geometric | +++/+ | +/- |
| Claudication Onset Time | +/+ | -/- |
| Ankle Brachial Index | +/+ | +/+ |
| WIQ: claudication | +/+ | -/+ |
| WIQ: distance | 0/- | +/- |
| WIQ: speed | +/- | +/0 |
| WIQ: stairs | ++/+ | +/- |
| SF-36: Physical Score | ++/+ | +/- |
| SF-36: Mental Score | +/- | +/- |

+++=p<.05;++=p<.15;+,0,-=directional change relative to placebo
SINGLE/DOUBLE

FIG. 13.

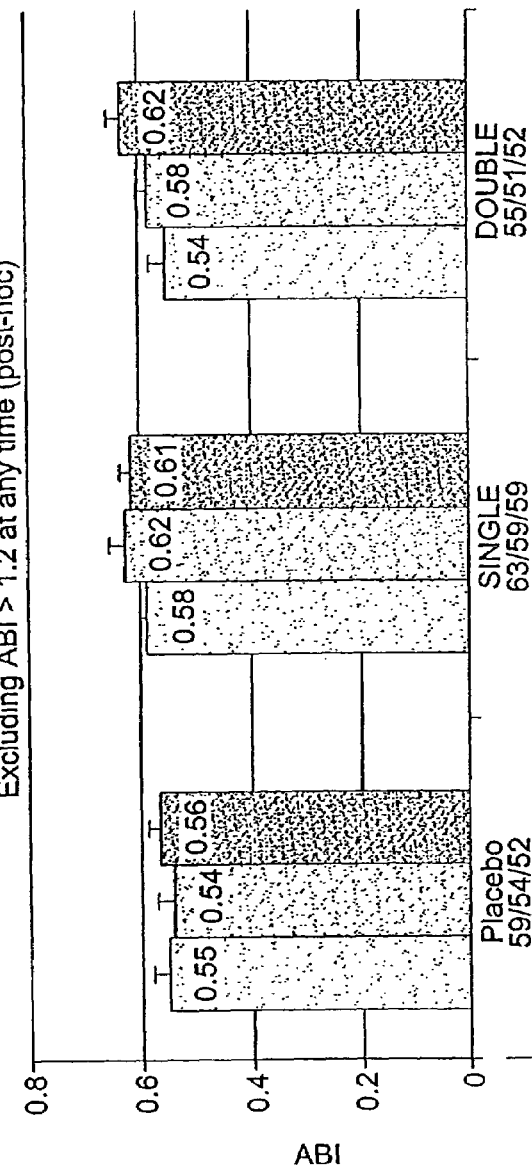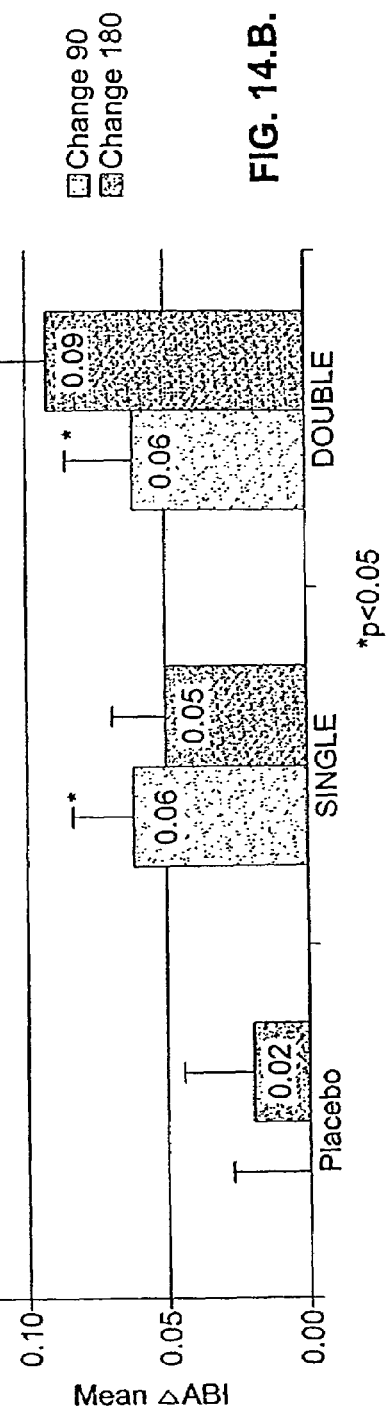
FIG. 14.A.
FIG. 14.B.

METHODS AND COMPOSITIONS FOR THE TREATMENT OF PERIPHERAL ARTERY DISEASE

CROSS-REFERENCE TO RELATED APPLICATIONS

This application is a continuation of U.S. application Ser. No. 09/886,856; filed Jun. 21, 2001, now abandoned, which claims the benefit of U.S. Provisional Application Ser. Nos. 60/213,504, filed Jun. 22, 2000, 60/264,572, filed Jan. 26, 2001, and 60/276,549, filed Mar. 16, 2001, each of which is entitled "Methods and Compositions for the Treatment of Peripheral Artery Disease," the contents of which are herein incorporated by reference in their entirety.

FIELD OF THE INVENTION

The invention relates to methods and pharmaceutical compositions for treating peripheral artery disease, particularly the administration of compositions that contain recombinant fibroblast growth factor-2 (rFGF-2).

BACKGROUND OF THE INVENTION

Coronary artery disease (CAD) and peripheral artery disease (PAD) are conditions characterized by insufficient blood flow, usually secondary to atherosclerosis. Symptoms of ischemia (angina pectoris for CAD or intermittent claudication for PAD) are brought on by stress and relieved by rest. In CAD, symptoms may become life threatening due to myocardial infarction, arrhythmia, and progressive heart failure. In PAD, symptoms are less likely to be life threatening except when critical limb ischemia develops, but the risk of adverse cardiovascular events and death is increased.

Identification and management of risk factors are important in the medical management of both CAD and PAD. Pharmacologic management of risk factors may include anti-hypertensives, lipid-lowering agents, and hypoglycemic agents; smoking cessation, diet, and exercise are often prescribed with variable compliance. Pharmacologic management aimed at reduction of symptoms of ischemia often includes vasodilators, anti-anginal, and anti-platelet therapy. Mechanical revascularization by percutaneous angioplasty (with or without a stent) and direct surgical reconstruction improve blood flow and reduce symptoms. However, restenosis after angioplasty and progression of disease may limit the duration of the benefit.

PAD afflicts approximately 11 million patients in the United States. Approximately one third of these patients experience intermittent claudication (discomfort, pain, fatigue, or heaviness in the leg muscles that consistently is brought on by the same amount of muscular activity and relieved by rest). Claudication is similar to angina and represents ischemic muscle pain that may be localized to the hip, buttock, thigh, or calf. It occurs predictably with the same amount of physical stress. Atherosclerosis is systemic, but often one lower limb is more affected than the other. Patients may develop critical limb ischemia, with rest pain, non-healing ulcers, and/or gangrene. Rest pain occurs when blood supply is inadequate to meet the basic nutritional requirements at rest and typically localizes in the toes or foot of the affected limb.

The prevalence of CAD and PAD is expected to increase in countries with aging populations, as aging is a primary risk factor for atherosclerosis. Less invasive catheter-based treatment methods and more cost-effective programs and treatment methodologies are needed to manage these conditions.

SUMMARY OF THE INVENTION

Compositions and methods for treating peripheral artery disease (PAD) in a patient are provided. Pharmaceutical compositions comprising a therapeutically effective amount of fibroblast growth factor, such as FGF-2, and a pharmaceutically acceptable carrier are provided. Such compositions when administered in accordance with the methods of the invention provide effective treatment for PAD patients including those suffering intermittent claudication associated with this disease. Such compositions may also be administered to PAD patients to prevent progression of critical limb ischemia to amputation.

The methods of the invention comprise administering pharmaceutical compositions comprising a therapeutically effective amount of a growth factor, such as FGF-2, as an intra-arterial infusion (IA), intravenous infusion (IV), intramuscular injection (IM), or subcutaneous injection (SC). A single-dose administration of FGF-2 is efficacious for the treatment of PAD. Therapeutic benefits may be obtained with multiple doses without compromising safety. Administration of FGF-2 improves peak walking time in patients with PAD for at least 90 days after FGF-2 administration. FGF-2 can be used to treat patients suffering from critical limb ischemia including those with resting pain with and without non-healing ulcers. Additionally, FGF-2 can be used to treat PAD patients suffering from critical limb ischemia. The FGF-containing composition of the invention can be administered as adjuncts to vascular surgery involving mechanical bypass and percutaneous transluminal interventions with balloon catheters, with or without stents.

BRIEF DESCRIPTION OF THE DRAWINGS

FIG. 1 sets forth the DNA sequence (SEQ ID NO:1) encoding fibroblast growth factor-2 (FGF-2) having the amino acid sequence set forth in FIG. 2; this FGF-2 is of bovine origin. The translated amino acid sequence (SEQ ID NO:2) is also shown.

FIG. 2 sets forth the amino acid sequence (SEQ ID NO: 2) for the 146 amino acid residue bovine FGF-2 encoded by the DNA sequence set forth in FIG. 1.

FIG. 3 sets forth the DNA sequence (SEQ ID NO:3) encoding the translated amino acid sequence (SEQ ID NO:4) for the 146 amino acid residue FGF-2 of human origin.

FIG. 4 sets forth the DNA sequence (SEQ ID NO:5) encoding the translated amino acid sequence (SEQ ID NO:6) for the 155 amino acid residue FGF-2 of bovine origin.

FIG. 5 sets forth the DNA sequence (SEQ ID NO:7) encoding the translated amino acid sequence (SEQ ID NO:8) for the 155 amino acid residue FGF-2 of human origin.

FIG. 10 shows the results of the WIQ severity of claudication for the three patient groups in the phase II clinical study at day 90 (FIG. 10A) and day 180 (FIG. 10B). Values represent the percentage of patients in each group indicating an improvement, no change, or worsening of this condition.

FIG. 11 shows the severity scores at baseline, day 90, and day 180 for distance, speed, and stair climbing for each group. The figure demonstrates that the results for the single-dose group were better than the results for the placebo group for WIQ distance (FIG. 11A), speed (FIG. 11B), and stair climbing (FIG. 11C). The figure is shown with a scale where higher scores are better.

FIG. 13 summarizes the results of the study.

FIG. 14 shows the measured ABI (ankle-brachial index) (FIG. 14A) for the three patient groups of the phase II clinical study, when subjects having an ABI>1.2 at anytime (i.e., baseline, day 90, and/or day 180) are excluded from the analysis. A baseline measurement, a day-90 measurement, and the corresponding change between the baseline and day-90 measurement are indicated. The mean change in ABI (FIG. 14B) is also shown for the three patient groups.

DETAILED DESCRIPTION OF THE INVENTION

Figure 6:
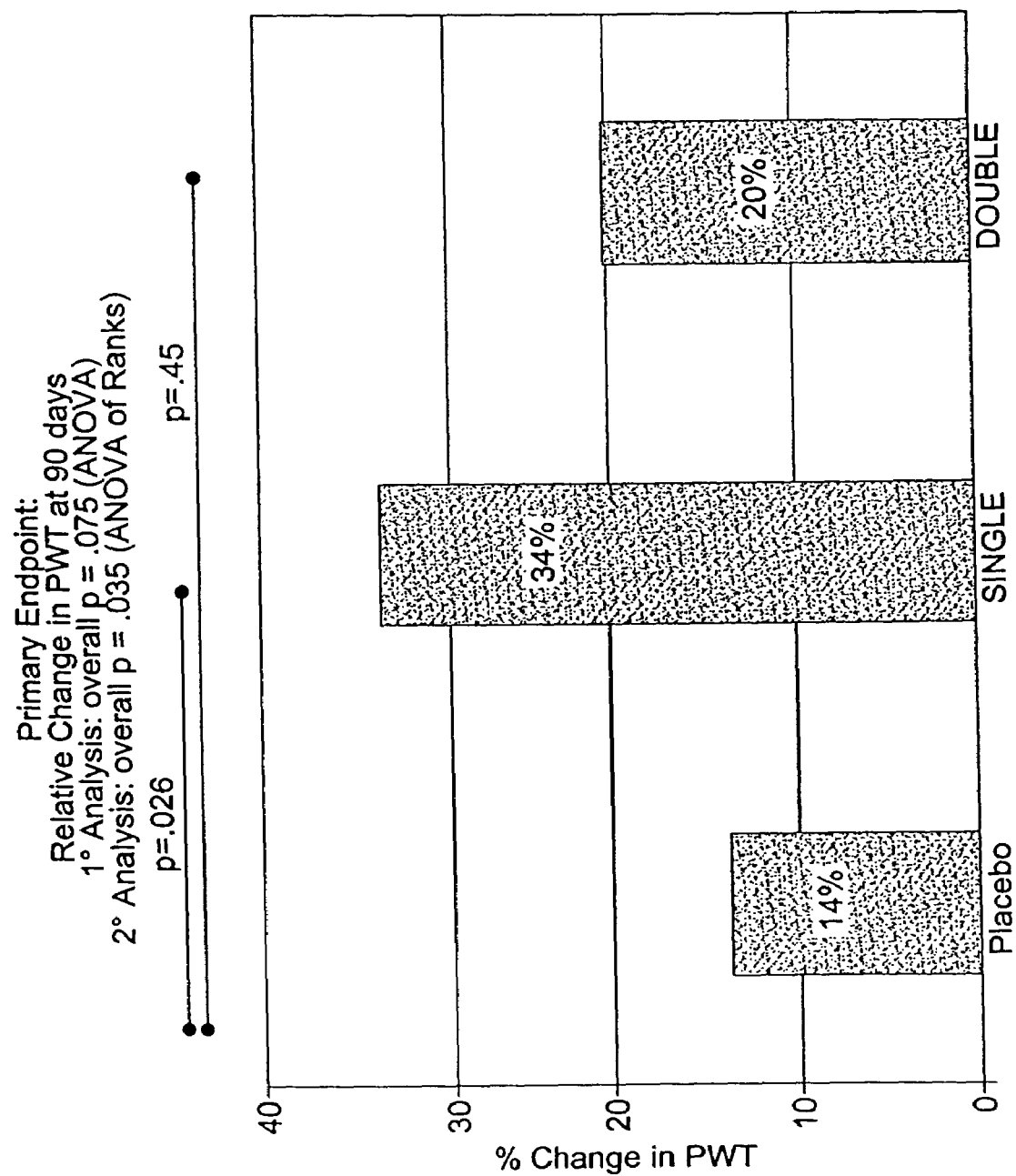
FIG. 6 shows the relative change in peak walking time (PWT) at day 90 with administration of rFGF-2 in patients in a phase II clinical study. In this study, three patient groups were assessed: a group administered a placebo on both days 1 and 30; a group administered a single dose of rFGF-2 (30 μg/kg) on day 1 and a placebo on day 30; and a group administered a dose of rFGF-2 (30 μg/kg) on both days 1 and 30. The mean and standard error are indicated for the measured PWT in each of these groups. The ANOVA analysis excluded patients with missing data and revascularized patients. The ANOVA of Ranks test included patients with missing data and revascularized patients by assigning the lowest rank. Pairwise comparison indicated a p value of 0.026 between the single dose and placebo groups and a p value of 0.45 between the double dose and placebo group. The figure provides the primary efficacy analysis of the clinical trial, which specified the use of log-transformed data. This is considered appropriate statistical management of data when the results have skewness or kertosis such as is often seen in treadmill tests.

One potential new alternative for the treatment of intermittent claudication due to peripheral artery disease (PAD) is the use of angiogenic growth factors that promote the formation of new blood vessels from preexisting ones (angiogenesis) and also restore endothelial cell function. In angiogenesis, endothelial cells leave their resting state and start to digest the underlying basement membrane followed by proliferation, migration, and finally formation of a hollow tube (Gerwins et al. (2000) *Crit. Rev. Oncol. Hematol.* 34(3):185–194). Fibroblast growth factors bind to cell surface receptors that are ligand-stimulatable tyrosine kinases. Binding of these growth factors to their receptors leads to activation of the intrinsic tyrosine kinase and signal transduction to downstream signaling cascades (Gerwins et al. (2000) *Crit. Rev. Oncol. Hematol.* 34(3):185–194). Angiogenesis in ischemic tissues can be promoted by the transmural delivery of angiogenic growth factors such as VEGF, FGF, and PDGF using an intravascular infusion catheter. See, for example, U.S. Pat. No. 5,941,868.

Compositions and methods for treating PAD in a patient are provided. The compositions and methods are useful in the treatment and prevention of claudication and critical limb ischemia due to PAD. The term "critical limb ischemia" is used for all patients with chronic ischemic rest pain, ulcers, or gangrene attributable to objectively proven arterial occlusive disease. The term "critical limb ischemia" implies chronicity and is to be distinguished from acute limb ischemia. By "acute limb ischemia" is intended any sudden decrease or worsening in limb perfusion causing a threat to extremity viability. See, *J. Vasc. Surg.* 31:S135, S168, herein incorporated by reference. The methods of the invention utilize angiogenic agents, such as angiogenic members, of the fibroblast growth factor (FGF) family, including preferably FGF-1, FGF-2, FGF-4, FGF-5, FGF-18, and most preferably FGF-2. It is recognized that all angiogenic growth factors herein described may be recombinant molecules. Also, it is recognized that compositions of the invention may comprise one or more fibroblast growth factors as angiogenic agents as well as biologically active variants thereof. Variants of an FGF sequence include, but are not limited to, angiogenically active fragments, analogues, and derivatives. By "fragment" is intended a polypeptide consisting of only a part of the intact FGF sequence and structure, and can be a C-terminal deletion, N-terminal deletion, or both. By "analogues" is intended analogues of either the angiogenic agent FGF or fragment thereof that comprise a native FGF sequence and structure having one or more amino acid substitutions, insertions, or deletions. Peptides having one or more peptoids (peptide mimics) and muteins, or mutated forms of the angiogenic agent, are also encompassed by the term analogue. By "derivatives" is intended any suitable modification of the angiogenic agent, fragments of the angiogenic agent, or their respective analogues, such as glycosylation, phosphorylation, or other addition of foreign moieties, so long as the angiogenic activity is retained. Methods for making fragments, analogues, and derivatives are available in the art. See generally U.S. Pat. Nos. 4,738,921, 5,158,875, and 5,077,276; International Publication Nos. WO 85/0083 1, WO 92/04363, WO 87/01038, and WO 89/05822; and European Patent Nos. EP 135094, EP 123228, and EP 128733; herein incorporated by reference.

Such variants should retain angiogenic activities and thus be "angiogenically active." The variants may be measured for angiogenic activity using standard bioassays. Representative assays include known radioreceptor assays using placental membranes (see, e.g., U.S. Pat. No. 5,324,639; Hall et al. (1974) *J. Clin. Endocrinol. and Metab.* 39:973–976; and Marshall et al. (1974) *J. Clin. Endocrinol. and Metab.* 39:283–292). Additional assays include mitogenic activity as determined in an in vitro assay of endothelial cell proliferation. This activity is preferably determined in a human umbilical vein endothelial (HUVE) cell-based assay, as described, for example, in any of the following publications: Gospodarowicz et al. (1989) *Proc. Natl. Acad. Sci. USA* 87:7311–7315; Ferrara and Henzel (1989) *Biochem. Biophys. Res. Commun.* 161:851–858; Conn et al. (1990) *Proc. Natl. Acad. Sci. USA* 87:1323–1327; Soker et al. (1998) *Cell* 92:735–745; Waltenberger et al. (1994) *J. Biol. Chem.* 269:26988–26995; Siemmeister et al. (1996) *Biochem. Biophys. Res. Commun.* 222:249–255; Fiebich et al. (1993) *Eur. J. Biochem.* 211: 19–26; Cohen et al. (1993) *Growth Factors* 7:131–138. A further biological activity is involvement in angiogenesis and/or vascular remodeling, which can be tested, for example, in the corneal pocket angiogenesis assay as described in Connolly et al. (1989) *J. Clin. Invest.* 84:1470–1478 and Lobb et al. (1985) *Biochemistry* 24:4969–4973; the endothelial cell tube formation assay, as described for example in Pepper et al. (1992) *Biochem. Biophys. Res. Commun.* 189:824–831; Goto et al. (1993) *Lab. Invest.* 69:508–517; or Koolwijk et al. (1996) *Cell Biol.* 132:1177–1188; the chick chorioallantoic membrane (CAM) angiogenesis assay as described for example in Pluet et al. (1989) *EMBO. J.* 8:3801–3806; the endothelial cell mitogenesis assay as described in Bohlen et al. (1984) *Proc. Natl. Acad. Sci. USA* 81:5364–5368; Presta et al. (1986) *Mol. Gen. Biol.* 6:4060–4066; Klagsbrun and Shing (1985) *Proc. Natl. Acad. Sci. USA* 82:805–809; Gosodarowicz et al. (1985) *J. Cell. Physiol.* 122:323–332; or the endothelial cell migration assay as described in Moscatelli et al. (1986) *Proc. Natl. Acad. Sci. USA* 83:2091–2095; and Presta et al. (1986) *Mol. and Cell. Biol.* 6:4060–4066; all of which are herein incorporated by reference. It is recognized that one or more of the assays may be used. Preferably, the variant has at least the same activity as the native molecule.

Fibroblast growth factor-2 (FGF-2), including recombinantly produced forms (rFGF-2), is a potent mitogen and angiogenic agent that has utility for treatment of coronary artery disease (angina) and peripheral artery disease (claudication). Although FGF-2 is normally made in many body tissues and is involved in the body's response to certain ischemic conditions, the body's own supply of FGF-2 may not be sufficient to circumvent the complications of atherosclerosis and arterial insufficiency/ischemia.

Compositions and methods of the invention can be used to treat PAD patients, even those suffering a wide spectrum of related clinical ailments, including but not limited to coronary artery disease (CAD), myocardial infarctions, stroke, diabetes, dyslipidemias, hypertension, and patients who have had surgical or catheter-based revascularizations. Fibroblast growth factors, particularly FGF-2, can be used to treat PAD patients suffering from claudication, including those having critical limb ischemia. Critical limb ischemia, when left untreated, can progress to acute limb ischemia and ultimately necessitate amputation of the limb. As such, the methods of the invention can be used to prevent acute limb ischemia.

The FGF-containing compositions of the invention are administered intra-arterially (IA), intravenously (IV), intramuscularly (IM), subcutaneously (SC), transmurally, and the like to a patient in need thereof. By "transmural" administration is intended localized delivery of the composition into the blood vessel or body lumen wall including neointimal, intimal, medial, advential, and perivascular spaces, particularly adjacent to the target site. By "target site" is intended the area surrounding or immediately surrounding the blood supply into the extremities, e.g, legs.

Intra-arterial administration (IA) involves delivery of the FGF-containing composition into at least one artery. In an IA infusion, the infusion is typically divided into several arteries in the legs, e.g., the left and right common femoral arteries, but is sometimes administered into a single artery. The infusion can be administered for about 1 minute, 1 to 5 minutes, 10 to 20 minutes, or 20 to 30 minutes into each artery in both legs. The infusion can be repeated from time to time to achieve or sustain the predicted benefit. The timing for repeat administration is based on the patient's response as measured by symptoms and hemodynamic measures. A therapeutically effective dose or amount of FGF, such as FGF-2, that is to be given as an infusion can be divided into two doses, and a single dose administered into each leg of a patient undergoing treatment. In this manner, the total dose is delivered such that the angiogenic agent is presented to both legs of the patient.

Thus in one embodiment, a therapeutically effective dose or amount of FGF as defined elsewhere herein is administered via IA infusion using a bilateral delivery method such that the procedure can be completed with a single puncture. In this manner, one-half of the therapeutically effective amount or total dose of FGF, such as rFGF-2, is infused into the common femoral artery of the first leg, followed by guiding the catheter over the bifurcation of the aorta to the contralateral iliac artery and common femoral artery and then infusing the remainder of the total dose into the femoral artery of the second leg. The rate of each infusion, one into each leg, is about 1 mL/per minute over about a 10-minute period, with a short interruption between the first and second infusion. Thus, the second infusion generally begins within about 1 hour of the first infusion, but can begin up to 2, 3, or 4 hours after the first infusion. Preferably the second infusion begins within about 30 minutes, more preferably within about 20 minutes, even more preferably within about 10 minutes, still more preferably within about 5 minutes of the completion of the first infusion. Each infusion can take less than about 10 minutes, such as 3, 4, or 5 minutes, so long as the FGF is not administered as a bolus. It is recognized by one of skill in the art that the therapeutically effective dose or amount of FGF, such as rFGF-2, can be divided between the two legs of the patient such that unequal portions of the total dose are delivered to each leg, for example, one-third to one leg, and two-thirds to the other leg. The advantage of the bilateral delivery method is that the two infusions, one into each leg, can be accomplished with a single puncture to the subject. In this embodiment, the sight of the puncture is preferably at groin level. A brachial approach may be used if deemed preferable by the treating physician. With this procedure, the catheter can be guided more distally, such as in the area just above the knee, as long as the obstruction to blood flow remains distal to the point of infusion.

Alternatively, the therapeutically effective amount of FGF, such as rFGF-2, can be delivered by direct IA puncture into each common femoral artery. In this manner, one-half of the dose of FGF is administered into one common femoral artery, while the other half of the dose of FGF is administered into the other common femoral artery. Direct IA puncture can be advantageous in that it avoids the catheterization procedure required with bilateral delivery, but it necessitates two punctures when the therapeutically effective dose is to be divided and infused into both legs. As with bilateral delivery, each infusion is delivered at a rate of about 1 mL per minute over about a 10-minute period, with a short interruption between the first and second infusion. Thus, the second infusion generally begins within about 1 hour of the first infusion, but can begin up to 2, 3, or 4 hours after the first infusion. Preferably the second infusion begins within about 30 minutes, more preferably within about 20 minutes, even more preferably within about 10 minutes, still more preferably within about 5 minutes of the completion of the first infusion. Each infusion can take less than about 10 minutes, such as 3, 4, or 5 minutes, so long as the FGF is not administered as a bolus. Again, it is recognized that the therapeutically effective dose or amount of FGF, such as rFGF-2, can be divided between the two legs of the patient such that unequal portions of the total dose are delivered to each leg.

Delivery of the FGF-containing compositions in accordance with the methods of the invention may be accomplished through a variety of known intravascular drug delivery systems. Such delivery systems include intravascular catheter delivery systems. A variety of catheter systems useful for the direct transmural infusion of angiogenic growth factors into the blood vessel are well known in the art. For purposes of practicing the invention, any of a variety of diagnostic or therapeutic type catheters could be used. Where the FGF is administered in conjunction with an angioplasty, balloon catheters can be used. Balloon catheters having expandable distal ends capable of engaging the inner wall of a blood vessel and infusing an angiogenic growth factor directly therein are well described in the patent literature. See, for example, U.S. Pat. Nos. 5,318,531; 5,304, 121; 5,295,962; 5,286,254; 5,254,089; 5,213,576; 5,197, 946; 5,087,244; 5,049,132; 5,021,044; 4,994,033; and 4,824,436. Catheters having spaced-apart or helical balloons for expansion within the lumen of a blood vessel and delivery of a therapeutic agent to the resulting isolated treatment site are described in U.S. Pat. Nos. 5,279,546; 5,226,888; 5,181,911; 4,824,436; and 4,636,195. Non-balloon drug delivery catheters are described in U.S. Pat. Nos. 5,180,366; 5,112,305; and 5,021,044; and PCT Publication WO 92/11890. Catheters that provide for distal vessel access, as well as stents also can be used. Ultrasonically assisted drug delivery catheters (phonophoresis devices) are described in U.S. Pat. Nos. 5,362,309; 5,318,014; and 5,315, 998. Other iontophoresis and phonophoresis drug delivery catheters are described in U.S. Pat. Nos. 5,304,120; 5,282, 785; and 5,267,985. Sleeve catheters having drug delivery lumens intended for use in combination with conventional angioplasty balloon catheters are described in U.S. Pat. Nos. 5,364,356 and 5,336,178. All of these references are herein incorporated by reference.

Direct intramuscular (IM) injections can be used to administer the angiogenic agents of the invention. The agents for injection can include the FGF protein or angiogenically active fragments of the protein as well as the gene or plasmid encoding the angiogenically active FGF protein or fragment. Injections are administered to the affected limb(s), in the thigh or calf, in the vicinity of existing vessels, near collateral flow vessels or conduit vessels such as arteries and arterials. The therapeutically effective dose of angiogenic agent is administered as a single injection, or can be divided and administered as multiple injections. Preferably the therapeutically effective amount or dose is delivered as 1 to about 20 injections, 1 to about 15 injections, more preferably 1 to about 10 injections. A single dose of angiogenic agent can be administered intramuscularly, and repeated as needed based on symptoms and/or hemodynamic measures. Local delivery such as with IM injection can provide the added benefit of administering lower doses of the angiogenic agent. See Example 4 herein, and the copending application entitled *"Dose of an Angiogenic Factor and Method of Administering to Improve Myocardial Blood Flow,"* filed Aug. 11, 2000 and assigned U.S. patent application Ser. No. 09/637,471, based on U.S. provisional application No. 60/148,746, filed Aug. 13, 1999, both of which herein incorporated by reference. The advantage to IM injection(s) is that it is less likely to result in hypotension, is more likely to have a longer half-life in the ischemic area, is less invasive, and therefore, can be repeated more frequently than the IA infusion. An IA infusion or an IM injection(s) could be "boosted" by an IM injection(s) every 1–2 months as warranted by clinical symptoms.

Recombinant FGF-2 releases nitric oxide, a potent vasodilator, aggressive fluid management prior to (proactively) and during the infusion is critical to patient's safety. Administration of IV fluids (e.g., 500–1000 mL of normal saline) to establish an estimated wedge pressure of 12 mm Hg prior to infusion and administration of boluses of IV fluids (e.g., 200 mL normal saline) for decreases of systolic blood pressure (e.g., <90 mm Hg) associated with infusion optimized the safety of administration of rFGF-2 by IC or IV infusion to human patients.

Because a sudden bolus of rFGF-2 is associated with profound hypotension in animals, the rate of infusion is critical to patient's safety. Administration at 0.5 to 2 mL per minute, typically 1 mL per minute, optimized the safety of administration of rFGF-2 by IC or IV infusion to human patients.

In another embodiment of the invention, compositions comprising fibroblast growth factor (FGF), including but not limited to FGF-2, can be administered to a patient with peripheral artery disease, including those with claudication, in conjunction with vascular or mechanical bypass surgery or angioplasty. The FGF, including but not limited to FGF-2, can be administered with and without a stent during surgery. The FGF may thus be administered as an adjunct to vascular surgery involving mechanical bypass and angioplasty.

The compositions of the invention provide a safe and therapeutically effective amount of fibroblast growth factor to improve blood flow. By "safe and therapeutically effective amount" is intended an amount of a fibroblast growth factor such as FGF-2, or angiogenically active variant or fragment thereof, that when administered in accordance with the invention is free from major complications that cannot be medically managed, and that provides for objective improvement in patients having symptoms of PAD. It is recognized that the therapeutically effective amount may vary from patient to patient depending upon age, weight, severity of symptoms, general health, physical condition, and the like. Other factors include the mode of administration and the respective amount of FGF included in the pharmaceutical composition. Typically, a therapeutically effective amount of an angiogenic agent of the invention, such as FGF-2, is about 0.1 µg/kg to about 100 µg/kg, preferably about 0.20 µg/kg to about 75 µg/kg, more preferably about 0.4 µg/kg to about 50 µg/kg, even more preferably about 0.50 µg/kg to about 35 µg/kg, more preferably still about 1.0 µg/kg to about 30 µg/kg based on actual body weight. Thus, when the angiogenic agent is FGF-2, a therapeutically effective amount of FGF-2 is about 0.1 µg/kg to about 1 µg/kg, 0.1 µg/kg to about 1 µg/kg, about 1 µg/kg to 3 µg/kg, about 3 µg/kg to about 5 µg/kg, about 5 µg/kg to about 7 µg/kg, about 7 µg/kg to about 8 µg/kg, about 8 µg/kg to about 9 µg/kg, about 9 µg/kg to about 9.9 µg/kg, such as about 9.0, 9.1, 9.2, 9.3, 9.4, 9.5, 9.6, 9.7, 9.8, or 9.9 µg/kg, up to about 10 µg/kg, about 10 µg/kg to about 15 µg/kg, about 15 µg/kg to about 20 µg/kg, about 20 µg/kg to about 30 µg/kg, about 30 µg/kg to about 40 µg/kg, about 40 µg/kg to about 60 µg/kg, about 60 µg/kg to about 80 µg/kg of the rFGF-2, depending upon the route and the mode of administration.

As indicated, the compositions and methods of the invention are useful for treating or preventing PAD and symptoms associated with PAD, including claudication and critical limb ischemia. In this manner, the desired therapeutic responses include increased exercise capacity, improvement in ankle-brachial index, reduction in body pain and claudication. In cases of PAD patients with critical limb ischemia, desired therapeutic responses include resolution of unremitting rest pain that is not controllable by analgesic, healing of ulcers, and prevention of gangrene and amputation.

Methods for monitoring efficacy of administration of FGF, particularly FGF-2, for treatment of PAD are well known in the art. See, for example, methods for monitoring increased blood flow into affected limbs, including, but not limited to, Doppler ultrasound, plethysmography (Macdonald (1994) *J. Vas. Tech.* 18:241–248), and magnetic resonance spectroscopy, ankle-brachial or toe systolic pressure index at rest and after a period of exercise, and increased collateral vessel density using angiography. Clinical indicators of efficacy include total treadmill walk time (i.e., peak walking time, PWT) and time to onset of claudication; and patient quality of life questionnaires.

The FGF-containing pharmaceutical compositions of the invention will be delivered for a time sufficient to achieve the desired physiological effect, i.e., angiogenesis, and/or restoration of endothelial cell function and the promotion of collateral blood vessels. The compositions may be administered as a single bolus, or multiple injections. Typically, the angiogenic factor will be delivered as an infusion over a period of time. It is recognized that any means for administration are encompassed including sustained-release formulations, plasmids, or genes, as well as other routes of administration. The total amount of time may vary depending on the delivery rate and drug concentration in the composition being delivered. For example, for intra-arterial administration, the time of administration may vary from 1 second to about 24 hours, more usually from about 1 minute to about 6 hours, specifically from about 5 minutes to about 30 minutes. A single intra-arterial dose administration is efficacious in the treatment of PAD.

When administered in accordance with the methods of the invention, FGF-containing compositions provide the patient with a safe and therapeutically efficacious treatment for PAD that lasts at least 1 month, 2 months, generally 3 months, 4 months, 6 months, and, in some cases, more than 6 months before a further treatment is needed. The angiogenic agent, such as FGF-2, can be administered once or twice per day about every week, preferably every month or more preferably every other month, even more preferably every 3 months, even more preferably every 4 months, and even more preferably still about every 6 months.

As indicated, fibroblast growth factors and related molecules are able to restore endothelial cell function and to promote endothelial and/or smooth muscle cell proliferation. The fibroblast growth factors (FGF) are a family of at least twenty-three structurally related polypeptides (named FGF-1 to FGF-23) that are characterized by a high degree of affinity for proteoglycans, such as heparin. The various FGF molecules range in size from 15 to at least 32.5 kDa, and exhibit a broad range of biological activities in normal and malignant conditions including nerve cell adhesion and differentiation (Schubert et al. (1987) *J. Cell. Biol.* 104: 635–643); wound healing (U.S. Pat. No. 5,439,818 (Fiddes)); as mitogens toward many mesodermal and ectodermal cell types, as trophic factors, as differentiation inducing or inhibiting factors (Clements et al. (1993) *Oncogene* 8:1311–1316); and as an angiogenic factor (Harada (1994) *J. Clin. Invest.* 94:623–630). Thus, the FGF family is a family of pluripotent growth factors that stimulate to varying extents fibroblasts, smooth muscle cells, epithelial cells, endothelial cells, myocytes, and neuronal cells. FGF-like polypeptides are also contemplated for use in the compositions and methods of the present invention. By "FGF-like" is intended polypeptides that bind FGF receptor 1, particularly receptor 1-C, bind to heparin-like molecules, and have angiogenic activity. By heparin-like molecule is intended heparin, proteoglycans, and other polyanionic compounds that bind FGF, that dimerize FGF, and that facilitate receptor activation. Of particular interest in the practice of the invention is the FGF designated FGF-2 as well as variants and fragments thereof, which are known in the art. For example, see U.S. Pat. Nos. 5,989,866; 5,925,528; 5,874,254; 5,852,177; 5,817,485; 5,714,458; 5,656,458; 5,604,293; 5,576,288; 5,514,566; 5,482,929; 5,464,943; and 5,439,818.

The FGF, more particularly FGF-2, to be administered can be from any animal species including, but not limited to, avian, canine, bovine, porcine, equine, and human. Generally, the FGF is from a mammalian species, preferably bovine or human in the case of FGF-2. The FGF may be in the native, recombinantly produced, or chemically synthesized forms as outlined below. Where the FGF is FGF-2, it may be the 146 amino acid form, the 153–155 amino acid form, or a mixture thereof depending upon the method of recombinant production. See U.S. Pat. No. 5,143,829, herein incorporated by reference. Further, angiogenically active muteins of the FGF-2 molecule can be used. See, for example, U.S. Pat. Nos. 5,859,208 and 5,852,177, herein incorporated by reference.

Biologically active variants of the FGF polypeptide of interest, more particularly FGF-2, are also encompassed by the methods of the present invention. As noted previously, such variants include fragments, analogues, and derivatives. Such variants should retain angiogenic activities and thus be "angiogenically active" as measured using standard bioassays noted above.

Variants of the native FGF used in the compositions and methods of the invention will generally have at least 70%, preferably at least 80%, more preferably about 90% to 95% or more, and most preferably about 98% or more amino acid sequence identity to the amino acid sequence of the reference FGF molecule. By "sequence identity" is intended the same amino acid residues are found within the variant and the reference FGF molecule when a specified, contiguous segment of the amino acid sequence of the variant is aligned and compared to the amino acid sequence of the reference FGF molecule, which serves as the basis for comparison. Thus, for example, where the reference FGF-2 molecule is human FGF-2, an angiogenically active variant thereof will generally have at least 70%, preferably at least 80%, more preferably about 90% to 95% or more, most preferably about 98% or more, sequence identify to the full-length amino acid sequence set forth in FIG. 3 (SEQ ID NO:4). In addition, other FGF receptor-binding peptides can be used as described in, for example, WO98/21237 or U.S. application Ser. No. 09/407,687, filed Sep. 28, 1999, herein incorporated by reference.

A polypeptide that is a biologically active variant of a reference polypeptide molecule of interest may differ from the reference molecule by as few as 1–15 amino acids, as few as 1–10, such as 6–10, as few as 5, as few as 4, 3, 2, or even 1 amino acid residue. The percentage sequence identity between two amino acid sequences is calculated by determining the number of positions at which the identical amino acid residue occurs in both sequences to yield the number of matched positions, dividing the number of matched positions by the total number of positions in the segment undergoing comparison to the reference molecule, and multiplying the result by 100 to yield the percentage of sequence identity.

For purposes of optimal alignment of the two sequences, the contiguous segment of the amino acid sequence of the variant polypeptide may have additional amino acid residues or deleted amino acid residues with respect to the amino acid sequence of the reference polypeptide molecule. The contiguous segment used for comparison to the reference amino acid sequence will comprise at least twenty (20) contiguous amino acid residues, and may be 30, 40, 50, 100, or more residues. Corrections for increased sequence identity associated with inclusion of gaps in the variant's amino acid sequence can be made by assigning gap penalties. Methods of sequence alignment are well known in the art for both amino acid sequences and for the nucleotide sequences encoding amino acid sequences.

Thus, the determination of percent identity between any two sequences can be accomplished using a mathematical algorithm. One preferred, non-limiting example of a mathematical algorithm utilized for the comparison of sequences is the algorithm of Myers and Miller (1988) *CABIOS* 4:11–17. Such an algorithm is utilized in the ALIGN program (version 2.0), which is part of the GCG sequence alignment software package. A PAM120 weight residue table, a gap length penalty of 12, and a gap penalty of 4 can be used with the ALIGN program when comparing amino acid sequences. Another preferred, nonlimiting example of a mathematical algorithm for use in comparing two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to a nucleotide sequence encoding the polypeptide of interest. BLAST protein searches can be performed with the XBLAST program, score=50, wordlength=3, to obtain amino acid sequences homologous to the polypeptide of interest. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See ncbi.nlm.nih.gov (a www prefix must be used). Also see the ALIGN program (Dayhoff (1978) in *Atlas of Protein Sequence and Structure* 5:Suppl. 3 (National Biomedical Research Foundation, Washington, D.C.) and programs in the Wisconsin Sequence Analysis Package, Version 8 (available from Genetics Computer Group, Madison, Wis.), for example, the GAP program, where default parameters of the programs are utilized.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Myers and Miller (1988) *Computer Applic. Biol. Sci.* 4:11–17.

The art provides substantial guidance regarding the preparation and use of FGF polypeptide variants. In preparing the polypeptide variants, one of skill in the art can readily determine which modifications to the native nucleotide or amino acid sequence will result in a variant that is suitable for use as a therapeutically active component of a pharmaceutical composition of the present invention for use in the methods of the invention directed to treatment of patients having peripheral artery disease.

Fibroblast growth factors, such as FGF-2, are formulated into pharmaceutical compositions for use in the methods of the invention. In this manner, a pharmaceutically acceptable carrier may be used in combination with the angiogenic agent such as FGF-2 and other components in the pharmaceutical composition. By "pharmaceutically acceptable carrier" is intended a carrier or diluent that is conventionally used in the art to facilitate the storage, administration, and/or the desired effect of the therapeutic ingredients. A carrier may also reduce any undesirable side effects of the angiogenic agent, i.e., FGF or variant thereof. A suitable carrier should be stable, i.e., incapable of reacting with other ingredients in the formulation. It should not produce significant local or systemic adverse effect in recipients at the dosages and concentrations employed for therapy. Such carriers are generally known in the art. Suitable carriers for this invention are those conventionally used large stable macromolecules such as albumin, gelatin, collagen, polysaccharide, monosaccarides, polyvinylpyrrolidone, polylactic acid, polyglycolic acid, polymeric amino acids, fixed oils, ethyl oleate, liposomes, glucose, sucrose, lactose, mannose, dextrose, dextran, cellulose, mannitol, sorbitol, polyethylene glycol (PEG), heparin alginate, and the like. Slow-release carriers, such as hyaluronic acid, may also be suitable. Stabilizers, such as trehalose, thioglycerol, and dithiothreitol (DTT), may also be added. See, for example, copending U.S. application Ser. No. 60/229,238, entitled "Stabilized FGF Formulations Containing Reducing Agents," herein incorporated by reference. FGF formulations comprising DTT as described in this application are defined herein as "stabilized FGF-DTT formulations and include stabilized FGF-2-DTT formatting." Other acceptable components in the composition include, but are not limited to, buffers that enhance isotonicity such as water, saline, phosphate, citrate, succinate, acetic acid, and other organic acids or their salts. Further, the angiogenic agents of the invention may be administered using a patch for slow release. Such formulation may include DMSO.

Preferred pharmaceutical compositions may incorporate buffers having reduced local pain and irritation resulting from injection. Such buffers include, but are not limited to, low phosphate buffers and succinate buffers. The pharmaceutical composition may additionally comprise a solubilizing compound that is capable of enhancing the solubility of an angiogenic agent or variant.

For the purposes of this invention, the pharmaceutical composition comprising the angiogenic agent FGF or angiogenically active variant thereof should be formulated in a unit dosage and in an injectable or infusible form such as solution, suspension, or emulsion. It can also be in the form of lyophilized powder, which can be converted into solution, suspension, or emulsion before administration. The pharmaceutical composition may be sterilized by membrane filtration, which also removes aggregates, and stored in unit-dose or multi-dose containers such as sealed vials or ampules.

The method for formulating a pharmaceutical composition is generally known in the art. A thorough discussion of formulation and selection of pharmaceutically acceptable carriers, stabilizers, and isomolytes can be found in *Remington's Pharmaceutical Sciences* (18$^{th}$ ed.; Mack Pub. Co.: Eaton, Pa. 1990), herein incorporated by reference.

The pharmaceutical compositions of the present invention can also be formulated in a sustained-release form to prolong the presence of the pharmaceutically active agent in the treated patient, generally for longer than one day. Many methods of preparation of a sustained-release formulation are known in the art and are disclosed in *Remington's Pharmaceutical Sciences* (18$^{th}$ ed.; Mack Pub. Co.: Eaton, Pa., 1990), herein incorporated by reference. Generally, the agent can be entrapped in semipermeable matrices of solid hydrophobic polymers. The matrices can be shaped into films or microcapsules. Examples of such matrices include, but are not limited to, polyesters, copolymers of L-glutamic acid and gamma ethyl-L-glutamate (Sidman et al. (1983) Biopolymers 22:547–556), poly-actides (U.S. Pat. No. 3,773,919 and EP 58,481), polyactate polyglycolate (PLGA), hydrogels (see, for example, Langer et al. (1981) *J. Biomed. Mater. Res.* 15:167–277; Langer (1982) *Chem. Tech.* 12:98–105), non-degradable ethylene-vinyl acetate, degradable lactic acid-glycolic acid copolymers such as the Lupron Depot™, and poly-D-(−)-3-hydroxybutyric acid (EP 133,988). Suitable microcapsules can also include hydroxymethylcellulose or gelatin-microcapsules and polymethylmethacylate microcapsules prepared by coacervation techniques or by interfacial polymerization. Microparticles such as heparin alginate beads may also be used. In addition, microemulsions or colloidal drug delivery systems such as liposomes and albumin microspheres, may also be used See a *Remington's Pharmaceutical Sciences* (18$^{th}$ ed.; Mack Pub. Co.: Eaton, Pa., 1990).

In particular, a mammalian fibroblast growth factor of bovine origin, FGF-2 of FIG. 2 (SEQ ID NO:2) also known as basic FGF (bFGF), and human FGF-2 of FIG. 3 (SEQ ID NO:4), or an angiogenically active fragment or mutein thereof, can be utilized in the practice of the invention. The nucleotide sequence encoding bovine FGF-2 is set forth in FIG. 1 (SEQ ID NO: 1). The nucleotide sequence encoding human FGF-2 is set forth in FIG. 3 (SEQ ID NO:3). See also, U.S. Pat. No. 5,604,293, herein incorporated by reference. The dose of FGF-2 that is predicted to result in clinical benefit to a patient whose exercise capacity is limited by claudication associated with PAD ranges from about 0.1 µg/kg to about 100 µg/kg of the FGF-2, preferably about 0.20 µg/kg to about 75 µg/kg, more preferably about 0.4 µg/kg to about 50 µg/kg, even more preferably about 0.50 µg/kg to about 35 µg/kg, more preferably still about 1.0 µg/kg to about 30 µg/kg, and most likely from 0.3 to 3.5 mg as a standard dose. Thus, in one embodiment, the therapeutically effective dose of FGF-2, such as recombinant FGF-2 (rFGF-2), is about 0.1 µg/kg to about 1 µg/kg, about 1 µg/kg to 3 µg/kg, about 3 µg/kg to about 5 µg/kg, about 5 µg/kg to about 7 µg/kg, about 7 µg/kg to about 8 µg/kg, about 8 µg/kg to about 9 µg/kg, about 9 µg/kg to about 9.9 µg/kg, such as about 9.0, 9.1, 9.2, 9.3, 9.4, 9.5, 9.6, 9.7, 9.8, or 9.9 µg/kg, up to about 10 µg/kg, about 10 µg/kg to about 15 µg/kg, about 15 µg/kg to about 20 µg/kg, about 20 µg/kg to about 30 µg/kg, about 30 µg/kg to about 40 µg/kg, about 40 µg/kg to about 60 µg/kg, about 60 µg/kg to about 80 µg/kg of the FGF-2, depending on the route and mode of administration.

It is convenient to define the dose of angiogenic agent in more absolute terms that are not dependent upon the weight of the patient to be treated. In this embodiment, the dose is referred to as a "standard" dose. When so defined, the standard dose to be administered in accordance with the methods of the present invention ranges from about 4.0 µg to about 7.2 mg, such as about 4.0 µg to about 0.3 mg, preferably from about 0.3 mg to about 1.0 mg, even more preferably from about 1.0 mg to about 2.0 mg, more preferably still from about 2.0 mg to about 2.5 mg, from about 2.5 mg to 3.5 mg, from about 3.5 mg to about 4.5 mg, from about 4.5 mg to about 5.5 mg, from about 5.5 mg to about 6.5 mg, up to about 7.2 mg. In this embodiment, the standard dose is a sufficient amount of FGF-2 to accommodate dosing any one of the majority of human PAD patients, ranging from the smallest patient (e.g., 40 kg) at the lowest dosage (about 0.1 µg/kg) through the larger patients (e.g., 150 kg) at higher dosages (about 48 µg/kg for this embodiment). For example, when a patient weighs 70 kg the standard dose ranges from about 0.2 mg to about 3.0 mg, from about 0.5 mg to about 2.5 mg, preferably about 2.1 mg, depending upon the route and mode of administration.

Where lower doses of FGF-2 are contemplated, such as between 0.1 µg/kg up to about 10 µg/kg, the standard dose to be administered in accordance with the methods of the present invention ranges from about 7.0 µg to about 0.7 mg, about 8 µg to about 0.6 mg, about 9 µg to about 0.5 mg, about 0.1 mg to about 0.4 mg, preferably about 0.21 mg for a 70 kg patient. Thus, in some embodiments, the standard dose for a 70 kg patient ranges from about 7.0 µg to about 0.7 mg, including 8 µg, 9 µg, 0.1 mg, 0.2 mg. 0.3 mg, 0.4 mg, 0.5 mg, 0.6 mg, 0.65 mg, up to about 0.7 mg.

Because FGF-2 is a glycosaminoglycan- (e.g., heparin) binding protein and the presence of a glycosaminoglycan (also known as a "proteoglycan" or a "mucopolysaccharide") optimizes activity and area under the curve (AUC), the dosages of FGF-2 of the present invention may be administered within 20 to 30 minutes of an intravenous (IV) administration of a glycosaminoglycan, such as a heparin. Various fractionated and unfractionated heparins, proteoglycans, and sulfated mucopolysaccharides such as chondroitin sulfate can be used in the practice of the invention. Low molecular weight heparins (<10,000 d) and unfractionated (i.e., high molecular weight) heparins (>10,000 d) can be used in the practice of the invention. These molecules can be administered together with the rFGF-2 or within 20 to 30 minutes of administration of the rFGF-2. Heparin is suitably dosed at 20–80 units/kg, and preferably at 40 units/kg.

In one embodiment, the unit dose contains a sufficient amount of FGF-2 ranging from about 0.1 µg/kg to about 80 µg/kg. More typically, the systemic unit dose comprises 0.3 mg to 3.5 mg of the FGF-2 of FIG. 2 (SEQ ID NO:2) or the FGF-2 of FIG. 3 (SEQ ID NO:4), or an angiogenically active fragment or mutein thereof. Dosages for local delivery comprising about 0.01 µg to about 500 µg up to about 3 mg may be used. When administered locally as with IM injections, the dose may be the same as, one-tenth of, or one-hundredth of the dose administered intra-arterially. The unit dose is typically provided in solution or reconstituted lyophilized form containing the above-referenced amount of FGF-2 and an effective amount of one or more pharmaceutically acceptable buffers, stabilizers, and/or other excipients as described elsewhere herein.

The recombinant FGF-2 having the amino acid sequence of FIG. 2 (SEQ ID NO:2) is made as described in U.S. Pat. No. 5,155,214, entitled "Basic Fibroblast Growth Factor," which issued on Oct. 13, 1992, and which is incorporated herein by reference in its entirety. As disclosed in the '214 patent, a DNA of FIG. 1 (SEQ ID NO: 1), which encodes a bFGF (hereinafter "FGF-2") of FIG. 2 (SEQ ID NO:2), is inserted into a cloning vector, such as pBR322, pMB9, Col E 1, pCRI, RP4 or λ-phage, and the cloning vector is used to transform either a eukaryotic or prokaryotic cell, wherein the transformed cell expresses the FGF-2. In one embodiment, the host cell is a yeast cell, such as *Saccharomyces cerevisiae*. The resulting full length FGF-2 that is expressed has 146 amino acids in accordance with FIG. 2 (SEQ ID NO:2). Although the FGF-2 of FIG. 2 (SEQ ID NO:2) has four cysteines, i.e., at residue positions 25, 69, 87 and 92, there are no internal disulfide linkages. ['214 at col. 6, lines 59–61.] However, in the event that cross-linking occurred under oxidative conditions, it would likely occur between the residues at positions 25 and 69.

The 146-residue mammalian FGF-2 of FIG. 2 (SEQ ID NO:2), which is of bovine origin, like the corresponding 146-residue human FGF-2 of FIG. 3 (SEQ ID NO:4) is initially synthesized in vivo as a polypeptide having 155 amino acids (Abraham et al. (1986) *EMBO J.* 5(10):2523–2528; FIG. 4 (SEQ ID NO:6) of bovine origin; FIG. 5 (SEQ ID NO:8) of human origin). When compared to the full-length 155-residue FGF-2 molecules, the 146-residue FGF-2 molecules lack the first nine amino acid residues, Met-Ala-Ala-Gly-Ser-Ile-Thr-Thr-Leu (SEQ ID NO:9), at the N-terminus of the corresponding full-length bovine and human 155-residue FGF-2 molecules (FIG. 4 (SEQ ID NO:6) and FIG. 5 (SEQ ID NO:8), respectively). The 155-residue FGF-2 of human or bovine origin, and biologically active variants thereof, can also be used in the compositions and methods of the present invention in the manner described for the bovine and human 146-residue FGF-2 molecules. Again it is recognized that the 155-residue form may exist as 153–155 residues, or mixtures thereof, depending upon the method of recombinant protein production. The mammalian FGF-2 of FIG. 2 (SEQ ID NO:2) differs from human FGF-2 of FIG. 3 (SEQ ID NO:4) in two residue positions. In particular, the amino acids at residue positions 112 and 128 of the mammalian FGF-2 of FIG. 2 (SEQ ID NO:2) are Ser and Pro, respectively, whereas in human FGF-2 (FIG. 3; SEQ ID NO:4), they are Thr and Ser, respectively. For the 155-residue forms, these differences appear at residue positions 121 and 137 of FIG. 4 (SEQ ID NO:6; FGF-2 of bovine origin) and FIG. 5 (SEQ ID NO:8; FGF-2 of human origin).

The recombinant FGF-2 employed in the present compositions and methods was purified to pharmaceutical quality (90% or greater purity by weight of total proteins, preferably 92% or greater purity, more preferably 95% or greater purity, preferably substantially pure, that is about 98% purity by weight of total proteins) using the techniques described in detail in U.S. Pat. No. 4,956,455, entitled "Bovine Fibroblast Growth Factor," which issued on Sep. 11, 1990 and which is incorporated herein by reference in its entirety. In particular, the first two steps employed in the purification of the recombinant FGF-2 used in a unit dose of a pharmaceutical composition of the invention are "conventional ion-exchange and HPLC purification steps as described previously." [U.S. Pat. No. 4,956,455, citing to Bolen et al. (1984) *Proc. Natl. Acad. Sci. USA* 81:5364–5368. I'm not sure about these references.] The third step, which the '455 patent refers to as the "key purification step" ['455 at col. 7, lines 5–6], is heparin-SEPHAROSE® affinity chromatography, wherein the strong heparin binding affinity of the FGF-2 is utilized to achieve several thousand-fold purification when eluting at approximately 1.4 M and 1.95 M NaCl ['455 at col. 9, lines 20–25]. Polypeptide homogeneity may be confirmed by reverse-phase high pressure liquid chromatography (RP-HPLC). Buffer exchange was achieved by SEPHADEX® G-25(M) gel filtration chromatography.

In addition to the 146-residue FGF-2 of FIG. 2 (SEQ ID NO:2), the therapeutically active agent in the unit dose of the present invention also comprises an "angiogenically active fragment" of the FGF-2 of FIG. 2 (SEQ ID NO:2). By the term "angiogenically active fragment of the FGF-2 of FIG. 2 (SEQ ID NO:2)" is meant a fragment of FGF-2 that has about 80% of the 146 residues of FIG. 2 (SEQ ID NO:2) and that retains the angiogenic effect of the FGF-2 of FIG. 2 (SEQ ID NO:2). This definition of "angiogenically active fragment" also applies to human FGF-2 of FIG. 3 (SEQ ID NO:4). An "angiogenically active fragment" of the FGF-2 of FIG. 4 (SEQ ID NO:6) or FIG. 5 (SEQ ID NO:8) is a fragment of FGF-2 that has about 80% of the 155 residues of FIG. 4 (SEQ ID NO:6) or FIG. 5 (SEQ ID NO:8), respectively.

To be angiogenically active, the FGF-2 fragment should have two cell binding sites and at least one of the two heparin binding sites. The two putative cell binding sites of the analogous 146-residue human FGF-2 (hFGF-2; SEQ ID NO:4) occur at about residue positions 36–39 and about 77–81 thereof. See Yoshida et al. (1987) *Proc. Natl. Aca. Sci. USA* 84:7305–7309, at FIG. 3. The two putative heparin binding sites of hFGF-2 occur at about residue positions 18–22 and 107–111 thereof. See Yoshida (1987), at FIG. 3. Given the substantial similarity between the amino acid sequences for human FGF-2 (hFGF-2) and bovine FGF-2 (bFGF-2), it is expected that the cell binding sites for bFGF-2 (FIG. 2 (SEQ ID NO:2)) are also at about residue positions 36–39 and about 77–81 thereof, and that the heparin binding sites are at about residue positions 18–22 and about 107–111 thereof The additional 9 residues of the 155-residue form do not affect the relative positions of these binding sites with respect to residues 1–146 shown in FIG. 2 (SEQ ID NO:2; FGF-2 of bovine origin) or FIG. 3 (SEQ ID NO:4; FGF-2 of human origin). Thus, for the 155-residue form of human FGF-2 (FIG. 5; SEQ ID NO:8), the two putative cell binding sites occur at about residue positions 45–48 and about 86–90 thereof, and the two putative heparin binding sites occur at about residue positions 27–31 and about 116–120 thereof. Again, given the substantial similarity between the 155-residue bovine and human proteins, it is expected that the two putative cell binding sites are at about residue positions 45–48 and about 86–90, and the two putative heparin binding sites are at about residue positions 27–31 and about 116–120 of the 155-residue bovine FGF-2 (FIG. 4; SEQ ID NO:6). Consistent with the above, it is well known in the art that N-terminal truncations of the FGF-2 of FIG. 2 (SEQ ID NO:2) do not eliminate its angiogenic activity in cows. In particular, the art discloses several naturally occurring and biologically active fragments of the FGF-2 that have N-terminal truncations relative to the FGF-2 of FIG. 2 (SEQ ID NO:2). An active and truncated bFGF-2 having residues 12–146 of FIG. 2 (SEQ ID NO:2) was found in bovine liver and another active and truncated bFGF-2, having residues 16–146 of FIG. 2 (SEQ ID NO:2) was found in the bovine kidney, adrenal glands, and testes. (See U.S. Pat. No. 5,155,214 at col. 6, lines 41–46, citing to Ueno et al. (1986) *Biochem. Biophys. Res. Comm.* 138: 580–588.) Likewise, other fragments of the bFGF-2 of FIG. 2 (SEQ ID NO:2) that are known to have FGF activity are FGF-2 (24–120)-OH and FGF-2 (30–110)-N1712-[U.S. Pat. No. 5,155,214 at col. 6, lines 48–52.] These latter fragments retain both of the cell binding portions of FGF-2 (FIG. 2 (SEQ ID NO:2)) and one of the heparin binding segments (residues 107–111). Accordingly, the angiogenically active fragments of a mammalian FGF typically encompass those terminally truncated fragments of an FGF-2 that have at least residues that correspond to residues 30-110 of the FGF-2 of FIG. 2 (SEQ ID NO:2); more typically, at least residues that correspond to residues 18–146 of the FGF-2 of FIG. 2 (SEQ ID NO:2).

It is recognized that other synthetic peptides based on native FGF sequences may be used as long as these peptides bind FGF receptors. Additionally hybrid FGF molecules may be constructed comprising peptides from different native sequences as well as combinations of native and synthetic sequences. Again, the hybrid molecules will retain the ability to bind with FGF receptors.

The unit dose of the present invention also comprises an "angiogenically active mutein" of the FGF-2 of FIG. 2 (SEQ ID NO:2), FIG. 3 (SEQ ID NO:4), FIG. 4 (SEQ ID NO:6), or FIG. 5 (SEQ ID NO:8). By the term "angiogenically active mutein" is intended a mutated form of the FGF-2 of FIG. 2 (SEQ ID NO:2), FIG. 3 (SEQ ID NO:4), FIG. 4 (SEQ ID NO:6), or FIG. 5 (SEQ ID NO:8) that structurally retains at least 80%, preferably 90%, of the 146 residues of the FGF-2 sequence shown in FIG. 2 (SEQ ID NO: 2), the 146 residues of the human FGF-2 sequence shown in FIG. 3 (SEQ ID NO:4), the 155 residues of the FGF-2 sequence shown in FIG. 4 (SEQ ID NO:6), or the 155 residues of the FGF-2 sequences shown in FIG. 5 (SEQ ID NO:8), respectively, in their respective positions, and that functionally retains the angiogenic activity of the respective unmutated form of FGF-2. Preferably, the mutations are "conservative substitutions" using L-amino acids, wherein one amino acid is replaced by another biologically similar amino acid. Examples of conservative substitutions include the substitution of one hydrophobic residue such as Ile, Val, Leu, Pro, or Gly for another, or the substitution of one polar residue for another, such as between Arg and Lys, between Glu and Asp, or between Gln and Asn, and the like. Generally, the charged amino acids are considered interchangeable with one another. However, to make the substitution more conservative, one takes into account both the size and the likeness of the charge, if any, on the side chain. Suitable substitutions include the substitution of serine for one or both of the cysteines at residue positions 87 and 92, which are not involved in disulfide formation. Other suitable substitutions include any substitution wherein at least one constituent cysteine is replaced by another amino acid so that the mutein has greater stability under acidic conditions, see for example U.S. Pat. No. 5,852,177 which is herein incorporated by reference. One such substitution is the replacement of cysteine residues with neutral amino acids such as for example: glycine, valine, alanine, leucine, isoleucine, tyrosine, phenylalanine, histidine, tryptophan, serine, threonine, and methionine (U.S. Pat. No. 5,852,177). Preferably, substitutions are introduced at the FGF-2 N-terminus, which is not associated with angiogenic activity. However, as discussed above, conservative substitutions are suitable for introduction throughout the molecule.

One skilled in the art, using well-known techniques, is able to make one or more point mutations in the DNA of FIG. 1 (SEQ ID NO:1), FIG. 3 (SEQ ID NO:3), FIG. 4 (SEQ ID NO:5), or FIG. 5 (SEQ ID NO:7) to obtain expression of an FGF-2 polypeptide mutein (or fragment of a mutein) having angiogenic activity for use within the unit dose, compositions, and methods of the present invention. To prepare an angiogenically active mutein of the FGF-2 of FIG. 2 (SEQ ID NO:2), FIG. 3 (SEQ ID NO:4), FIG. 4 (SEQ ID NO:6), or FIG. 5 (SEQ ID NO:8), one uses standard techniques for site-directed mutagenesis, as known in the art and/or as taught in Gilman et al. (1979) *Gene* 8:81 or Roberts et al. (1987) *Nature* 328:731, to introduce one or more point mutations into the cDNA of FIG. 1 (SEQ ID NO:1), FIG. 3 (SEQ ID NO:3) FIG. 4 (SEQ ID NO:5), or FIG. 5 (SEQ ID NO:7) that encodes the FGF-2 of FIG. 2 (SEQ ID NO:2), FIG. 3 (SEQ ID NO:4), FIG. 4 (SEQ ID NO:6), or FIG. 5 (SEQ ID NO:8), respectively.

Pharmaceutical compositions of the invention comprise an angiogenically effective dose of a mammalian FGF-2 of FIG. 2 (SEQ ID NO:2), FIG. 3 (SEQ ID NO:4), FIG. 4 (SEQ ID NO:6), FIG. 5 (SEQ ID NO:8) or an angiogenically active fragment or mutein thereof, and a pharmaceutically acceptable carrier. Typically, the safe and angiogenically effective dose of the pharmaceutical composition of the present invention is in a form and a size suitable for administration to a human patient and comprises (i) 1.0 µg/kg to 30.0 µg/kg of an FGF-2 of FIG. 2 (SEQ ID NO:2) or an angiogenically active fragment or mutein thereof, (ii) and a pharmaceutically acceptable carrier. In other embodiments, the safe and angiogenically effective dose comprises about 0.1 µg/kg to about 1 µg/kg, about 1 µg/kg to 3 µg/kg, about 3 µg/kg to about 5 µg/kg, about 5 µg/kg to about 7 µg/kg, about 7 µg/kg to about 8 µg/kg, about 8 µg/kg to about 9 µg/kg, about 9 µg/kg to about 9.9 µg/kg, such as about 9.0, 9.1, 9.2, 9.3, 9.4, 9.5, 9.6, 9.7, 9.8, or 9.9 µg/kg, up to about 10 µg/kg, about 10 µg/kg to about 15 µg/kg, about 15 µg/kg to about 20 µg/kg, about 20 µg/kg to about 30 µg/kg, about 30 µg/kg to about 40 µg/kg, about 40 µg/kg to about 60 µg/kg, about 60 µg/kg to about 80 µg/kg of the FGF-2 of FIG. 2 (SEQ ID NO:2), FIG. 3 (SEQ ID NO:4), FIG. 4 (SEQ ID NO:6), FIG. 5 (SEQ ID NO:8) or an angiogenically active fragment or mutein thereof, and a pharmaceutically acceptable carrier.

A typical pharmaceutical composition comprises 0.1 mg/ml to 10 mg/ml, more typically 0.3 mg/ml to 0.5 mg/ml, of FGF-2, more particularly recombinant FGF-2 (rFGF-2), having the sequence set forth in FIG. 2 (SEQ ID NO:2), or in FIG. 3 (SEQ ID NO:4), or an angiogenically active fragment or mutein thereof, 10 mM thioglycerol, 135 mM NaCl, 10 mM Na citrate, and 1 mM EDTA, pH 5.0. A suitable diluent or flushing agent for the above-described composition is any of the above-described carriers. Typically, the diluent is the carrier solution itself comprising 10 mM thioglycerol, 135 mM NaCl, 10 mM Na citrate, and 1 mM EDTA, pH 5.0. The rFGF-2 of FIG. 2 (SEQ ID NO:2) or an angiogenically active fragment or mutein thereof is unstable for long periods of time in liquid form. To maximize stability and shelf life, the pharmaceutical composition of the present invention comprising an effective amount of rFGF-2 or an angiogenically fragment or mutein thereof, in a pharmaceutically acceptable aqueous carrier should be stored frozen at −60° C. Thawed, the solution is stable for 1 month at refrigerated conditions. A typical unit dose would comprise about 5–10 ml of the above described composition having 1.5–8 mg of FGF-2 of FIG. 2 (SEQ ID NO:2), or FIG. 3 (SEQ ID NO:4).

In another embodiment, the pharmaceutical composition comprises a unit dose of FGF-2 of FIG. 2 (SEQ ID NO:2), FIG. 3 (SEQ ID NO:4), or an angiogenically active fragment or mutein thereof in lyophilized (freeze-dried) form. In this form, the unit dose of FGF-2 would be capable of being stored at room temperature for substantially longer than 6 months without loss of therapeutic effectiveness. Lyophilization is accomplished by the rapid freeze drying under reduced pressure of a plurality of vials, each containing a unit dose of the FGF-2 of the present invention therein. Lyophilizers, which perform the above described lyophilization, are commercially available and readily operable by those skilled in the art. Prior to administration to a patient, the lyophilized product is reconstituted to a known concentration, preferably in its own vial, with an appropriate sterile aqueous diluent, typically 0.9% (or less) sterile saline solution, or a compatible sterile buffer, or even sterile deionized water. See, for example, copending U.S. application Serial No. 60/229,238, entitled "Stabilized FGF Formulations containing Reducing Agents," herein incorporated by reference. Depending upon the weight of the patient in kg, a single dose comprising from 0.2 µg/kg to 36 µg/kg of the FGF-2 of FIG. 2 (SEQ ID NO:2), the FGF-2 of FIG. 3 (SEQ ID NO:4), or an angiogenically active fragment or mutein thereof is withdrawn from the vial as reconstituted product for administration to the patient. For example, an average 70 kg man that is being dosed at 24 µg/kg, would have a sufficient volume of the reconstituted product withdrawn from the vial to receive an infusion of (70 kg×24 µg/kg) 1680 µg (i.e., 1.680 mg).

The pharmaceutical composition in solution form is generally administered by infusing the unit dose substantially continuously over a period of about 10 to about 30 minutes, although it is recognized that the composition may be administered over a longer period of time. When the composition is administered into more than one blood vessel, typically, a portion (e.g., one half) of the unit dose is administered in a first vessel followed by administration into a second secondary vessel. Using the above-described repositioning procedure, portions of the unit dose may be administered to a plurality of vessels until the entire unit dose has been administered. After administration, the catheter is withdrawn using conventional protocols known in the art. Signs of angiogenesis and a therapeutic benefit, such as reduced claudication, improvement in ankle-brachial index, improvement in peak walking time, increase in ability to climb stairs, reduced body pain, improvement in or prevention of critical limb ischemia, and improved patient quality of life are seen as early as two weeks to one month following the FGF-2 administration.

The following examples are offered by way of illustration and not by way of limitation.

EXPERIMENTAL

Example 1

Unit Dose of rFGF-2 Employed in a Phase I Clinical Trial

The recombinantly produced FGF-2 (rFGF-2) having the sequence shown in FIG. 2 (SEQ ID NO:2) was formulated as a unit dose and pharmaceutical composition. The various formulations are described below.

The rFGF-2 unit dose was provided as a liquid in 3 cc type I glass vials with a laminated gray butyl rubber stopper and red flip-off overseal. The rFGF-2 unit dose contained 1.2 ml of 0.3 mg/ml rFGF-2 of FIG. 2 (SEQ ID NO:2) in 10 mM sodium citrate, 10 mM monothioglycerol, 1 mM disodium dihydrate EDTA (molecular weight 372.2), 135 mM sodium chloride, pH 5.0. Thus, in absolute terms, each vial (and unit dose) contained 0.36 mg rFGF-2. The vials containing the unit dose in liquid form were stored at 2° to 8° C.

The diluent was supplied in 5 cc type I glass vials with a laminated gray butyl rubber stopper and red flip-off overseal. The rFGF-2 diluent contains 10 mM sodium citrate, 10 mM monothioglycerol, 135 mM sodium chloride, pH 5.0. Each vial contained 5.2 ml of rFGF-2 diluent solution that was stored at 2° to 8° C. Such agents may also be administered to prevent progression of critical limb ischemia to amputation.

The rFGF-2 pharmaceutical composition that was infused was prepared by diluting the rFGF-2 unit dose with the rFGF diluent. In order to keep the EDTA concentration below the limit of 100 µg/ml, the total infusion volume was increased up to 40 ml when proportionately higher absolute amounts of FGF-2 were administered to patients.

Example 2

Phase II PAD Clinical Trial

Peripheral artery disease (PAD), as defined by resting anklebrachial index (ABI) less than 0.9, is a common condition afflicting about 15% of adults greater than 55 years of age. About 33% of these individuals are symptomatic with claudication; about 25% will progress. With worsening blood flow limitation, the spectrum of PAD runs from mild to moderate to severe claudication, followed by limb-threatening ischemia, initially characterized by rest pain, then poor wound healing, and impending or overt gangrene.

A phase II trial was undertaken to assess the efficacy of intra-arterial administration of rFGF-2 on exercise capacity in patients with intermittent claudication due to infra-inguinal PAD. The phase II PAD trial was a multicenter, randomized, double-blind, placebo-controlled, regimen finding study of rFGF-2 to evaluate the safety, pharmocokinetics, and efficacy by intra-arterial (IA) infusion over 20 minutes in PAD subjects with moderate to severe intermittent claudication. Major selection criteria for inclusion of a patient in the trial were age greater than 40 years, exercise limited by claudication, index ankle brachial index (ABI) of less than 0.8 at rest, patent femoral inflow, medically stable for greater than 4 months, and informed consent. Major selection criteria for exclusion of a patient from the trial were evidence of malignancy (according to ACS guidelines), creatinine greater than 2.0 mg/dL, urine protein greater than or equal to 2+ or greater than 300 mg/day, proliferative retinopathy, and/or other conditions impacting safety or compliance. 190 patients participated in the phase II PAD trial. Baseline characteristics of the patient population are shown in Tables 1–3.

TABLE 1

Baseline characteristics of the phase II PAD clinical trial patient population. ABI (ankle-brachial pressure index); PWT (peak walking time as measured on a treadmill at 2 mph with the incline increasing every 2 minutes; COT (claudication onset time).

|  | Placebo | SINGLE | DOUBLE | Any FGF |
|---|---|---|---|---|
| Number of Subjects | 63 | 66 | 61 | 127 |
| Median Age (yrs) | 67 | 65 | 68 | 67 |
| Male | 73% | 71% | 82% | 76% |
| Female | 27% | 29% | 18% | 24% |
| ABI at Rest (index) | 0.55 | 0.57 | 0.55 | 0.56 |
| PWT at Baseline | 5.32 | 5.15 | 5.81 | 5.48 |
| COT at Baseline | 1.97 | 2.03 | 2.20 | 2.13 |
| Current Smoker | 38% | 24% | 21% | 23% |
| Past Smoker | 43% | 59% | 61% | 60% |
| Never Smoker | 19% | 17% | 18% | 17% |
| Structured Exercise | 56% | 50% | 49% | 50% |

TABLE 2

Concurrent diagnoses of the target patient population in the phase II PAD clinical trial. CAD = coronary artery disease; CHF = congestive heart failure; MI = myochardial infarction; PTCA = percutaneous transluminal coronary angioplasty; S/P CABG = coronary artery bypass graft; PTI = percutaneous transluminal intervention-angioplasty.

|  | Placebo | SINGLE | DOUBLE | Any FGF |
|---|---|---|---|---|
| CARDIAC |  |  |  |  |
| History of CAD | 62% | 58% | 62% | 60% |
| History of CHF | 8% | 14% | 11% | 13% |
| Previous MI | 29% | 30% | 31% | 30% |
| CAD Angioplasty (PTCA) | 21% | 27% | 21% | 24% |
| S/P CABG | 41% | 33% | 31% | 32% |
| Prior PAD Surgery | 48% | 44% | 56% | 50% |
| Prior PTI | 21% | 27% | 21% | 24% |
| CEREBROVASCULAR |  |  |  |  |
| Previous Stroke | 8% | 6% | 7% | 6% |
| RISK FACTORS |  |  |  |  |
| Diabetes Mellitus | 36% | 27% | 38% | 33% |
| Hyperlipidemia | 75% | 77% | 75% | 76% |
| Hypertension | 79% | 67% | 75% | 71% |

TABLE 3

Incidence of peripheral angioplasty and limb revascularization in the target population of the phase II PAD clinical trial. Indicators of quality of life as measured by WIQ and SF-36 are also shown.

|  | Placebo | SINGLE | DOUBLE | Any FGF |
|---|---|---|---|---|
| Peripheral Angioplasty |  |  |  |  |
| None | 71% | 71% | 71% | 71% |
| One | 7% | 14% | 17% | 16% |
| >one | 22% | 14% | 12% | 13% |
| Limb Revascularization |  |  |  |  |
| None | 72% | 68% | 66% | 67% |
| One | 16% | 16% | 17% | 17% |
| >one | 12% | 16% | 17% | 17% |
| WIQ - distance score | 14% | 18% | 23% | 21% |
| WIQ - speed score | 19% | 21% | 26% | 23% |
| WIQ - stair climbing score | 32% | 23% | 37% | 30% |
| SF-36 - PCSS | 30.3 | 29.9 | 32.9 | 31.6 |

Approximately two-thirds of the patients had a history of coronary artery disease (CAD), slightly less than one-third had experienced myocardial infarction, one-third were diabetic, approximately three-fourths had hypertension, and/or dyslipidemia (Table 2). Approximately 20–30% of this target population had undergone greater than one vascularization procedure (Table 3). The low baseline quality of life scores (WIQ and SF-36) are indicative of a target PAD patient population with moderate to severe disease. The scores are based on a scale where 1 or 100% is normal. Thus an increase in the score represents an improvement. Scores are tabulated based on a questionnaire where patients perform a self-evaluation.

The rFGF-2 was administered by intra-arterial (IA) infusion over 20 minutes divided between two legs on days 1 and 30. The dose administered was 30 µg/kg of rFGF-2. The trial patients were divided into three groups: placebo; single dose (rFGF-2 on day 1); and double dose (rFGF-2 on days 1 and 30). The primary endpoint used in the study was a change in peak walking time (PWT) at day 90 on a Gardner graded exercise protocol. Secondary endpoints measured included: change in PWT at day 180, claudication onset time (COT; noted as the time at which the patient indicates claudication and/or pain begins), ankle-brachial pressure index (ABI; as determined using standard ultrasound device), and health-related quality of life (QOL) by Walking Impairment Questionnaire (WIQ) and Short-Form-36 (SF-36) at day 90 and day 180.

Recombinant FGF-2 (rFGF-2) was formulated in a solution containing 0.3 mg/ml rFGF-2, 10 mM sodium citrate, 0.3 mM EDTA, 10 mM thioglycerol, 135 mM sodium chloride, pH 5.0. Each 5 ml vial contained 3.7 ml of clear colorless solution (1.1 mg rFGF-2 per vial). Vials containing rFGF-2 were labeled "rFGF-2" and supplied frozen. Drug product was thawed at room temperature prior to preparation of dose; detailed instruction for pharmacists were provided in study manuals. Thawed, undiluted active drug product could be stored refrigerated at 2–8° C. for 30 days.

Drug product was diluted with placebo (diluent) and filtered before administration. The filter was sterile, non-pyrogenic, and low protein binding. Filtration of the drug product through a 0.22 micron syringe filter (e.g., Millipore, Millex-GV, #SLGVR25LS or equivalent) would remove particle with no resultant loss in strength or potency. Thawed, undiluted drug product was used within 8 hours.

Placebo (diluent) was supplied as a clear, colorless solution indistinguishable from the drug product. It contained 10 mM sodium citrate, 0.3 mM EDTA, 10 mM thioglycerol, 135 mM sodium chloride, pH 5.0. Vials containing diluent were labeled "placebo," supplied in a liquid state, and stored refrigerated at 2–8° C.

The results of the trial indicated that rFGF-2 had an acceptable safety profile at 90 days for both the single- and double-dose treatment groups. Dosing at day 1 and day 30 yielded similar safety data as single dosing at day 1 (data not shown).

Patient disposition and adverse events for patients at day 180 of the study are shown in Tables 4 and 5, respectively.

TABLE 4

Patient follow-up.

|  | Placebo | SINGLE | DOUBLE |
|---|---|---|---|
| Randomized: | 63 | 66 | 61 |
| Safety: 180 day FU | 57 | 63 | 56 |
| PWT: 90/180 days | 58/54 | 62/61 | 54/53 |
| Premature Termination | 6 | 3 | 5 |
| Death | 1 | 0 | 1 |
| Adverse Event | 1 | 0 | 0 |
| Withdrew Consent | 2 | 1 | 2 |
| Lost to FU | 2 | 2 | 2 |
| Revascularized/Amputation | 3 | 2 | 3 |

TABLE 5

Safety: Adverse Events

|  | Placebo | SINGLE | DOUBLE | Any FGF |
|---|---|---|---|---|
| Number of Subjects | 63 | 66 | 61 | 127 |
| Any AE | 41 (65%) | 43 (65%) | 46 (75%) |  |
| Any Cardiac AE | 8 | 6 | 7 | 13 |
| Hypotension | 2 | 4 | 5 | 9 |
| Proteinuria | 2 | 6 | 7 | 13 |
| Serious AEs | 13 (21%) | 9 (14%) | 14 (23%) |  |
| Deaths | 1 | 0 | 1 | 1 |
| Serious Cardiac AEs | 3 | 4 | 2 | 6 |
| Revascularizations/ Amputations | 3 | 2 | 3 | 5 |
| Gangrene | (2) | 0 | 0 | 0 |
| Malignancy | 1 | 0 | 0 | 0 |
| Retinal Disorders | 1 | 1 | 0 | 1 |
| Pleural/Pericardial Effusion | 1 | 0 | 0 | 0 |

Data Analysis

Primary analysis of the data was performed by ANOVA. Ten subjects with missing PWT and 6 subjects who were revascularized were excluded from the analysis. Secondary analysis was performed by ANOVA of Ranks. The 16 subjects excluded from the primary analysis were assigned lowest rank. This represents a more conservative approach. See, for example, Table 6.

TABLE 6

Evaluable vs intent to treat analysis.

1° Analysis by ANOVA: "Evaluable" = 174/190
Excludes 16 subjects who were revascularized (2 placebo, 3 single, 4 double) or missing data (3 placebo, 3 single, 4 double)
2° Analysis by ANOVA of Ranks: "Intent to Treat"
Assigns lowest rank to 16 subjects excluded above

| Hypothetical subjects | | | | |
|---|---|---|---|---|
| Baseline PWT n = 6 | Day 90 PWT | ANOVA n = 4 | Ranks n = 6 | |
| a | 8:40 | 10:20 | 1:40 | 4 |
| b | 5:30 | 6:55 | 1:25 | 3 |

TABLE 6-continued

Evaluable vs intent to treat analysis.

| c | 4:30 | 5:00 | → 0:30 | 2 |
|---|---|---|---|---|
| d | 6:20 | 6:00 | −0:20 | 1 |
| e | 4:00 | Angioplasty day 60 |  | 1 |
| f | 2:30 | Surgery day 89 |  | 1 |

Primary Endpoint: Peak Walking Time at Day 90

Recombinant FGF-2 was efficacious at treating PAD as measured by a statistically significant improvement in the PWT (p=0.026) at day 90 in the patients in the trial receiving a single dose of rFGF-2 compared to the control placebo group (FIG. 6). Also, results indicated that a double dose of rFGF-2 (days 1 and 30) was not better than a single dose (day 1).

Secondary Efficacy Variables

Secondary efficacy variables included PWT at day 180, claudication onset time (COT) and ankle brachial index (ABI) at days 90 and 180, and WIQ and SF-36 quality of life questionnaires at days 90 and 180. Results at day 180 reflect a large increase in placebo response.

Figure 7:
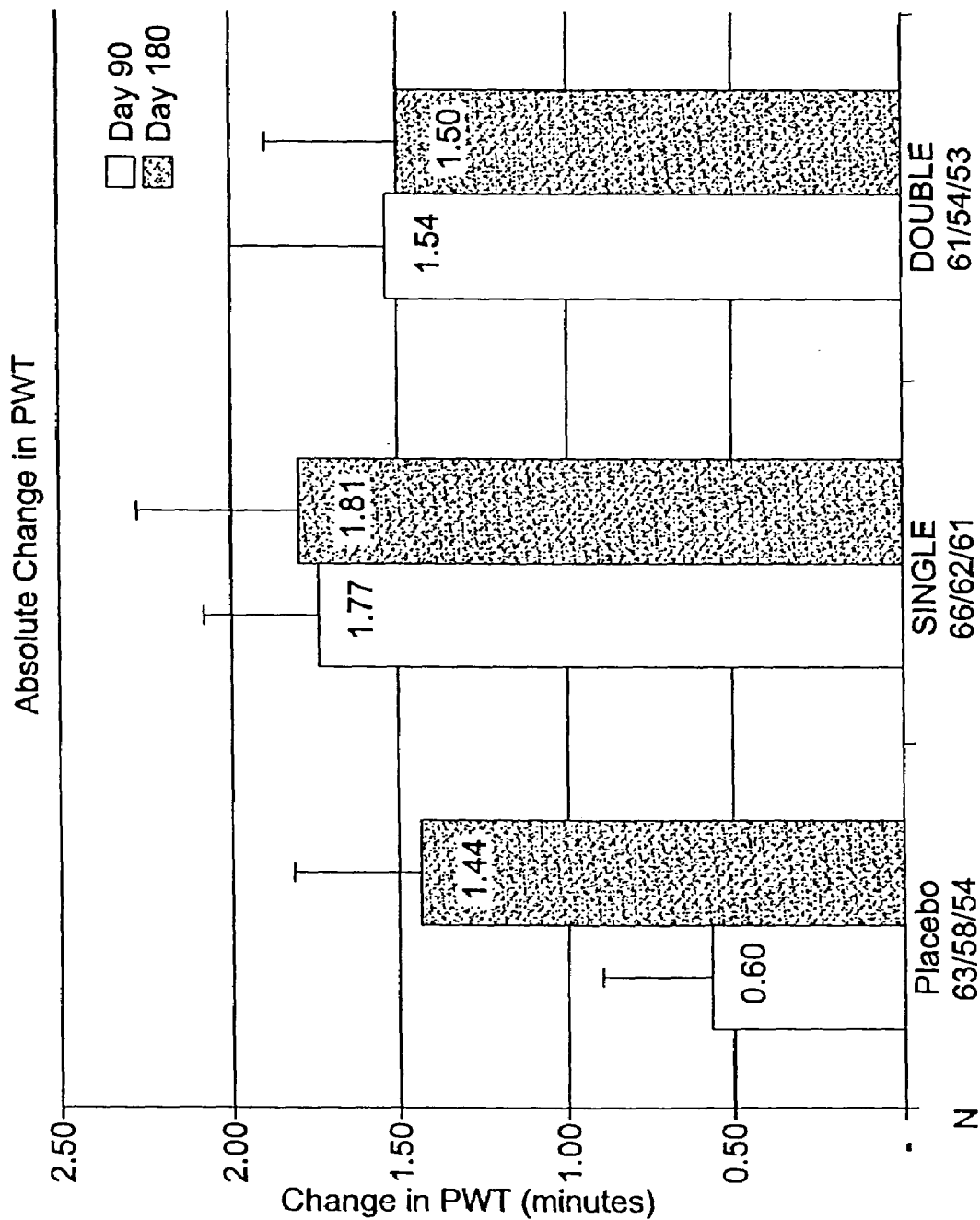
FIG. 7 shows absolute change in PWT at days 90 and 180 for the patient groups receiving placebo, single-dose rFGF-2, or double-dose rFGF-2. For each patient the PWT at baseline is subtracted from the PWT at day 90 and the differences are summed for each group and a mean determined; the data are analyzed by an analysis of variance (ANOVA).

FIG. 7 shows absolute change in PWT at days 90 and 180 for the patient groups receiving placebo, single-dose rFGF-2, or double-dose rFGF-2. For each patient the PWT at baseline is subtracted from the PWT at day 90 and the differences are summed for each group and a mean determined. The data are analyzed by an analysis of variance (ANOVA).

Figure 8:
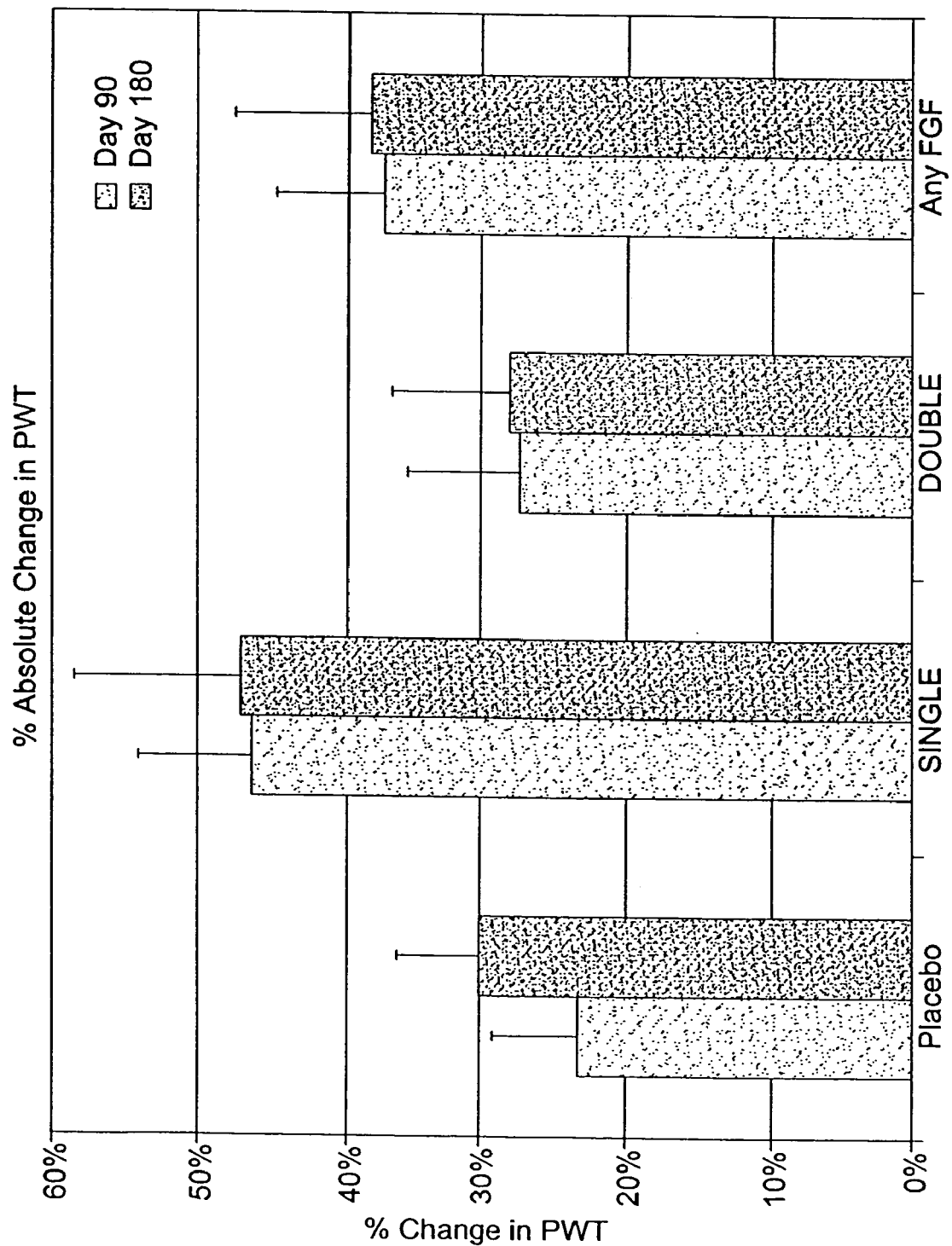
FIG. 8 shows the percent absolute change in PWT in the three patient groups shown at day 90 and day 180. The percent change in PWT averaged across the two rFGF-2 groups is also shown (designated Any FGF).

FIG. 8 shows the percent absolute change in PWT in the three patient groups shown at day 90 and day 180. The percent change in PWT averaged across the two rFGF-2 groups is also shown (designated Any FGF).

Figure 9:
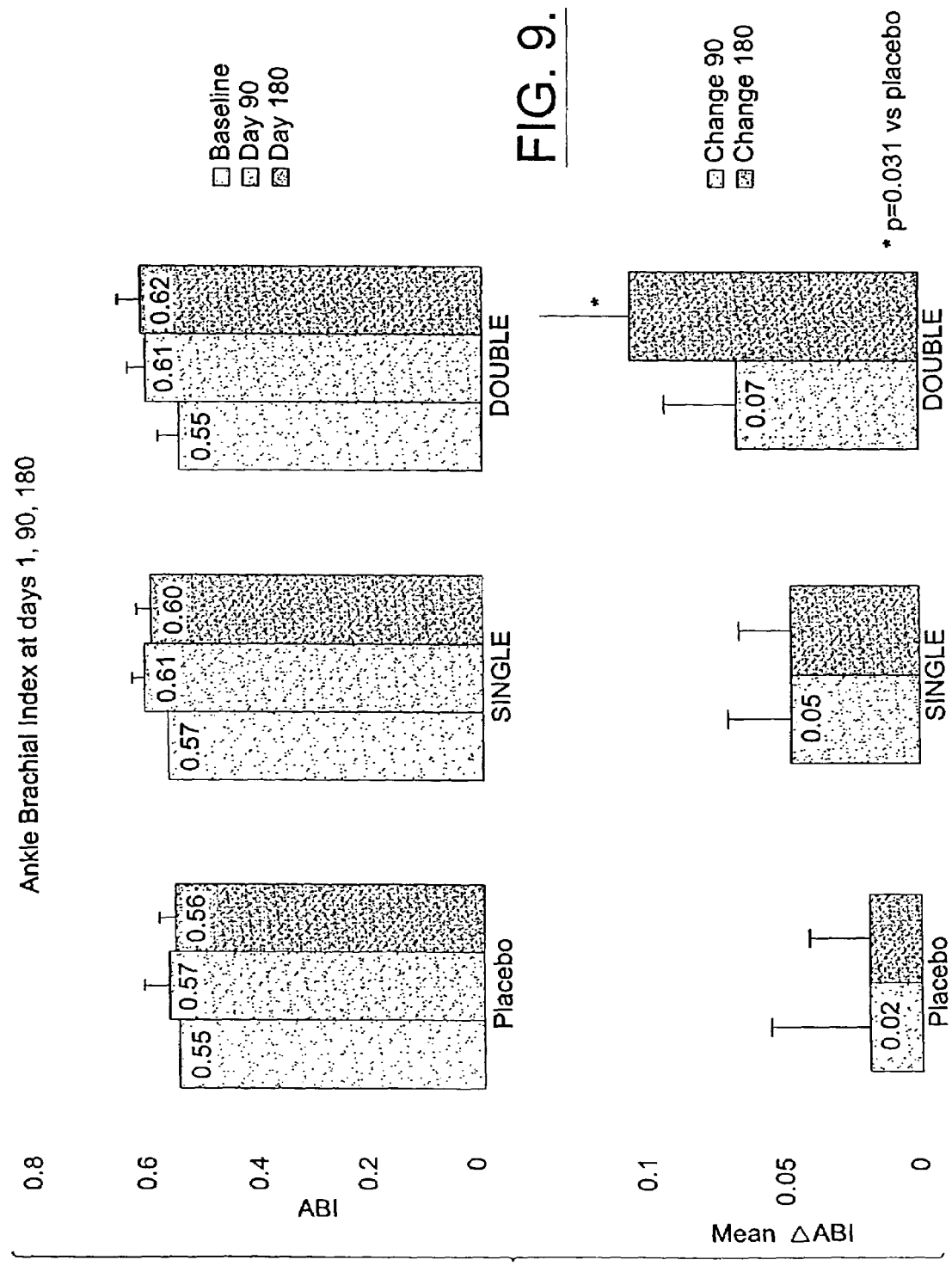
FIG. 9 shows the measured ABI (ankle brachial index) for the three patient groups of the phase II clinical study. A baseline measurement, a day-90 measurement, and the corresponding change between the baseline and day-90 measurement are indicated. The mean change in ABI is also shown for the three patient groups. The ABI is described in *An Office Based Approach to the Diagnosis and Treatment of Peripheral Arterial Disease* (2000) Society of Vascular Medicine and Biology (Medical Communications Media, Inc., Wrightstown, Pa.) herein incorporated by reference. Subjects having an ABI>1.2 at baseline are excluded from the analysis.

FIG. 9 shows the measured ABI (ankle brachial index) for the three patient groups of the phase II clinical study. A baseline measurement, a day-90 measurement, and the corresponding change between the baseline and day-90 measurement are indicated. The mean change in ABI is also shown for the three patient groups. The ABI is described in *An Office Based Approach to the Diagnosis and Treatment of Peripheral Arterial Disease* (2000) Society of Vascular Medicine and Biology (Medical Communications Media, Inc., Wrightstown, Pa.).

The anklebrachial index is the ratio of the systolic pressure in the foot to the systolic pressure in the arm as measured by a Doppler ultrasound device. The normal ABI is 1. An ABI less than 0.9 is considered diagnostic of PAD. The mean ABI of the target population enrolled in the trial was 0.56 in the index leg at rest. The index leg is the leg with the lower ABI. FIG. 9 shows the mean ABI (top panel) at baseline, day 90, and day 180 for each group. The bottom panel shows the mean change in ABI at day 90 and at day 180 for each group. There is a positive directional change in the treatment groups compared to placebo. The difference achieved statistical significance in the double-dose group at day 180 (mean $\Delta ABI=0.11$; p=0.031 versus placebo). As the ABI represents an objective measure of blood flow, this change is consistent with a proposed mechanism of FGF, the formation of new collateral blood vessels.

FIG. 10 represents the WIQ severity of claudication at days 90 and 180 for single- and double-dose groups relative to the placebo group. The bar values represent the percentage of patients in each group who improved, stayed the same, or became worse in each group. At day 90, greater than 50% of the patients in the treatment groups were improved whereas less than 40% of the placebo patients were improved. At day 180 this apparent treatment benefit is lost. For further information on the WIQ, see Regensteiner et al. (1990) *J. Vasc. Med. Biol.* 2:142–153 herein incorporated by reference.

FIG. 11 shows the severity scores at baseline, day 90, and day 180 for distance, speed, and stair climbing for each group. While changes are directionally positive for the FGF treatment groups for distance and speed, the results did not achieve statistical significance. For stair climbing, there was a trend of improvement for the single-dose group versus the placebo group (p=0.11). The figure shows that results for the single-dose group were better than results for placebo group for WIQ distance, speed, and stair climbing. The figure is shown with a scale where higher scores are better.

Figure 12:
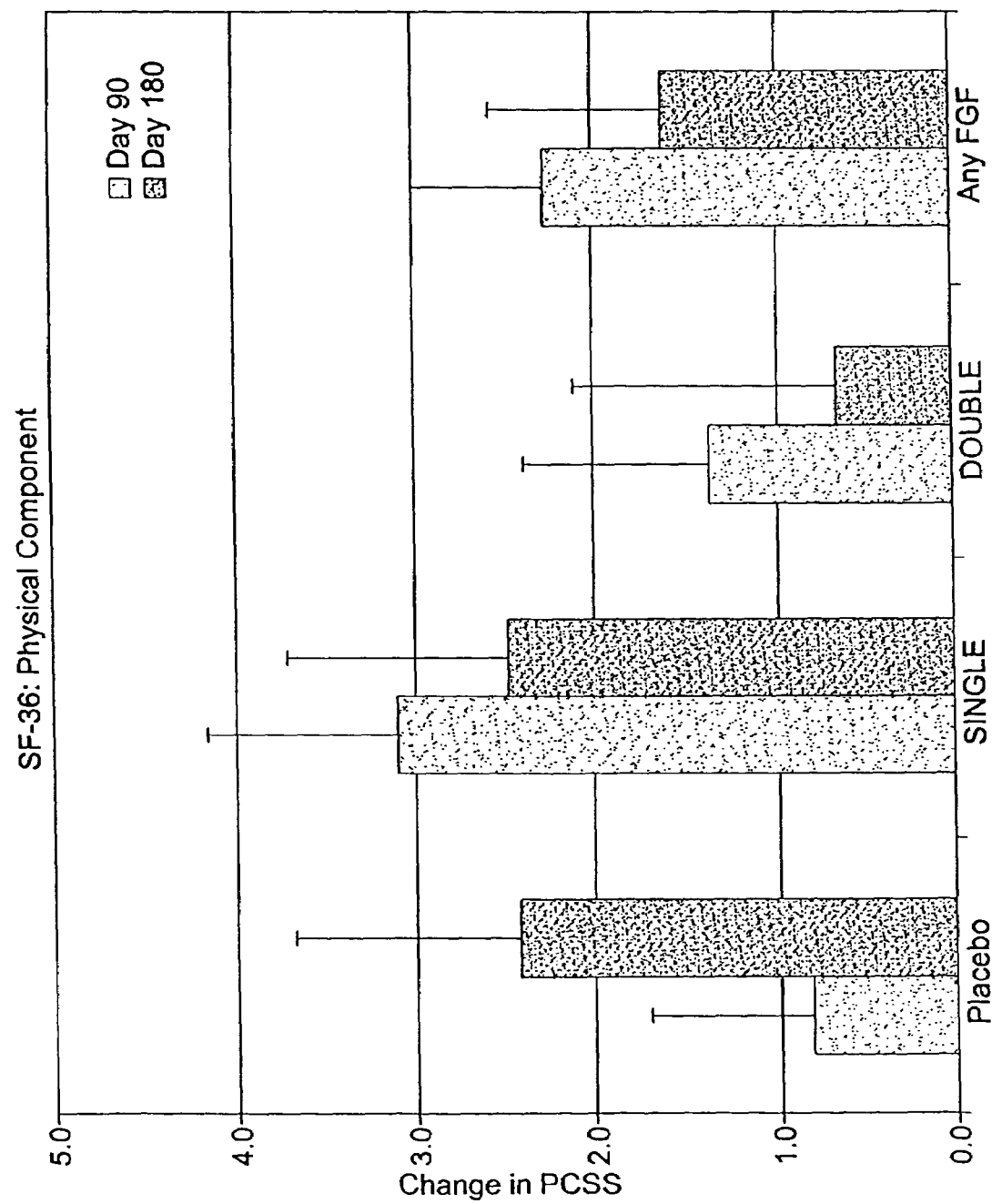
FIG. 12 depicts the physical summary scores from the short form 36 (SF-36). A change of 1 point is associated with an increased lifespan of 2 years. The change scores in the figure indicate an improvement in the single-dose group versus the placebo group by greater than 2 points at day 90.

FIG. 12 depicts the physical summary scores from the short form 36 ( SF-36). The SF-36 is a general validated quality of life instrument consisting of 36 questions. The SF-36 has 12 domains, which can be collapsed into two summary scores, physical and mental. A change of 1 point is associated with an increased lifespan of 2 years. The change scores in the figure indicate an improvement in the single-dose group versus the placebo group by greater than 2 points at day 90.

Results of the study are summarized in FIG. 13.

Examination of Subgroups

The analysis plan provided for the tracking of treatment response in three pre-specified subgroups of the phase II clinical trial patient population: diabetes (type I or II, yes vs no), smoking (current vs non-current, which included those individuals who had smoked in the past or had never smoked), and median age ($\leq$68 years vs >68 years). The results of the primary efficacy measure, change in PWT, are presented below for each subgroup. Data in Tables 7–12 reflect the log-transformed results (to be consistent with the primary efficacy analysis).

Diabetes

The results of PWT at days 90 and 180 are presented in Tables 7 and 8. There was no statistically significant difference between the placebo and FGF-treated groups. Changes were greater in both diabetics and non-diabetics in the FGF-treated groups at day 90. At day 180, changes were smaller in diabetics and similar in non-diabetics in the FGF-treated groups. The percentage of diabetics in the single-dose group was slightly lower (27% versus 37% in the placebo group, and 36% in the double-dose group).

TABLE 7

Change in PWT at day 90 and day 180 in diabetics.

|  | Placebo | Single | Double | Any FGF |
|---|---|---|---|---|
| Day 90 | N = 21 | N = 17 | N = 22 | N = 39 |
| Relative Change in PWT | 12.3% | 26.8% | 18.8% | 21.9% |
| Pair-wise P-value |  | .44 | .70 | .53 |
| Mean Change in PWT (min) | 1.08 | 1.42 | 1.26 | 1.33 |
| (+/−SD) | (1.84) | (2.74) | (3.08) | (2.90) |
| Overall P value = .74 |  |  |  |  |
| Day 180 | N = 20 | N = 17 | N = 21 | N = 38 |
| Relative Change in PWT | 18.2% | 7.6% | 4.6% | 5.8% |
| Pair-wise P-value |  | .64 | .52 | .52 |
| Mean Change in PWT (min) | 1.85 | 1.32 | 1.07 | 1.18 |
| (+/−SD) | (2.47) | (3.27) | (2.94) | (3.05) |
| Overall P value = .81 |  |  |  |  |

TABLE 8

Change in PWT at day 90 and day 180 in non-diabetics.

|  | Placebo | Single | Double | Any FGF |
|---|---|---|---|---|
| Day 90 | N = 37 | N = 45 | N = 32 | N = 77 |
| Relative Change in PWT | 13.0% | 34.9% | 18.7% | 28.0 |
| Pair-wise P-value |  | .061 | .65 | .14 |
| Mean Change in PWT (min) | .75 | 2.12 | 1.90 | 2.03 |
| (+/−SD) | (2.60) | (2.88) | (3.61) | (3.18) |
| Overall P value = .14 |  |  |  |  |
| Day 180 | N = 34 | N = 44 | N = 32 | N = 76 |
| Relative Change in PWT | 19.1% | 22.7% | 20.0% | 21.6% |
| Pair-wise P-value |  | .80 | .96 | .84 |
| Mean Change in PWT (min) | 1.57 | 2.15 | 1.89 | 2.04 |
| (+/−SD) | (2.91) | (3.97) | (2.89) | (3.54) |
| Overall P value = .96 |  |  |  |  |

Smoking

The results of the change in PWT at days 90 and 180 for current and non-current smokers are presented in Tables 9 and 10. For current smokers, no statistically significant difference was seen at day 90 or day 180. For non-current smokers at day 90, there was a statistically significant difference overall (p=0.007) and between the placebo and single-dose groups (P-value=0.002); at day 180, no statistically significant difference was seen. The results of regression analysis suggested smoking was a confounder of outcome.

TABLE 9

Change in PWT at day 90 and day 180 in current smokers.

|  | Placebo | Single | Double | Any FGF |
|---|---|---|---|---|
| Day 90 | N = 23 | N = 14 | N = 13 | N = 25 |
| Relative Change in PWT | 29.3% | 22.1% | 31.3% | 26.2% |
| Pair-wise P-value |  | .76 | .93 | .87 |
| Mean Change in PWT (min) | 1.55 | 2.27 | 2.36 | 2.31 |
| (+/−SD) | (2.67) | (4.22) | (3.91) | (4.00) |
| Overall P value = .93 |  |  |  |  |
| Day 180 | N = 20 | N = 14 | N = 11 | N = 25 |
| Relative Change in PWT | 27.2% | 1.0% | 43.3% | 18.1% |
| Pair-wise P-value |  | .25 | .53 | .66 |
| Mean Change in PWT (min) | 2.03 | 1.89 | 2.19 | 2.02 |
| (+/−SD) | (2.45) | (4.55) | (3.24) | (3.95) |
| Overall P value = .26 |  |  |  |  |

TABLE 10

Change in PWT at day 90 and day 180 in non-current smokers.

|  | Placebo | Single | Double | Any FGF |
|---|---|---|---|---|
| Day 90 | N = 35 | N = 48 | N = 43 | N = 91 |
| Relative Change in PWT | 5.5% | 35.9% | 15.8% | 26.1% |
| Pair-wise P-value |  | .002 | .27 | .019 |
| Mean Change in PWT (min) | 0.42 | 1.83 | 1.45 | 1.65 |
| (+/−SD) | (2.02) | (2.34) | (3.27) | (2.81) |
| Overall P value = .007 |  |  |  |  |
| Day 180 | N = 34 | N = 47 | N = 42 | N = 89 |
| Relative Change in PWT | 19.8% | 29.9 | 10.0% | 20.3% |
| Pair-wise P-value |  | .46 | .46 | .97 |
| Mean Change in PWT (min) | 1.46 | 1.93 | 1.40 | 1.68 |
| (+/−SD) | (2.90) | (3.57) | (2.84) | (3.24) |
| Overall P value = .28 |  |  |  |  |

Age

The results of the change in PWT at days 90 and 180 for subjects >68 years of age and ≦68 years of age are presented in Tables 11 and 12. There was a greater frequency of subjects with high PWT (≧8 minutes) in the double-dose group. For subjects >68 years, an unfavorable statistically significant difference was seen in the double-dose group at day 180 (P-value=0.031). For subjects ≦68 years, the change in PWT was higher in the FGF-treated groups, but no statistically significant difference was seen at day 90 or day 180. The results suggest a greater improvement in subjects ≦68 years of age.

TABLE 11

Change in PWT at day 90 and day 180 in subjects > 68 years of age.

|  | Placebo | Single | Double | Any FGF |
|---|---|---|---|---|
| Day 90 | N = 27 | N = 24 | N = 30 | N = 54 |
| Relative Change in PWT | 16.0% | 29.1% | 8.0% | 17.6% |
| Pair-wise P-value |  | .27 | .53 | .87 |
| Mean Change in PWT (min) | 1.00 | 1.58 | 0.81 | 1.15 |
| (+/−SD) | (2.18) | (2.66) | (2.25) | (2.45) |
| Overall P value = .22 |  |  |  |  |
| Day 180 | N = 25 | N = 25 | N = 29 | N = 54 |
| Relative Change in PWT | 28.8% | 7.1% | −4.0% | 1.4% |
| Pair-wise P-value |  | .19 | .031 | .044 |
| Mean Change in PWT (min) | 1.74 | 0.86 | 1.05 | 0.96 |
| (+/−SD) | (2.73) | (2.89) | (2.75) | (2.79) |
| Overall P value = .095 |  |  |  |  |

TABLE 12

Change in PWT at day 90 and day 180 in subjects ≦ 68 years of age.

|  | Placebo | Single | Double | Any FGF |
|---|---|---|---|---|
| Day 90 | N = 31 | N = 38 | N = 24 | N = 62 |
| Relative Change in PWT | 15.0% | 33.1% | 40.0% | 35.7% |
| Pair-wise P-value |  | .18 | .11 | .099 |
| Mean Change in PWT (min) | 0.76 | 2.16 | 2.67 | 2.36 |
| (+/−SD) | (2.51) | (2.96) | (4.25) | (3.49) |
| Overall P value = .23 |  |  |  |  |
| Day 180 | N = 29 | N = 36 | N = 24 | N = 60 |
| Relative Change in PWT | 25.8% | 31.5% | 48.2% | 37.9% |
| Pair-wise P-value |  | .72 | .25 | .44 |
| Mean Change in PWT (min) | 1.61 | 2.65 | 2.19 | 2.47 |
| (+/−SD) | (2.78) | (4.17) | (3.03) | (3.73) |
| Overall P value = .50 |  |  |  |  |

Post-hoc Responder Analysis

Of those subjects in the study whose PWT increased by ≧2 minutes at day 90, there was a higher frequency of subjects with low PWT (≦4 minutes) at baseline in the single-dose group. The strongest predictor of response at day 180 was the response at day 90. The change in PWT for subjects whose PWT increased by ≧2 minutes and for subjects whose PWT increased by <2 minutes are presented in Tables 13 and 14, respectively. There was a higher percentage of responders at days 90 and 180 and the magnitude of the change was greater in the single-dose group. About 40% of the patients receiving the single-dose treatment had an increase in PWT of greater than 2 minutes at both day 90 and day 180, while only about 22% and about 26% of the patients receiving placebo or a double dose of FGF-2 experienced this magnitude of response. In addition, the treatment effect appears to persist at day 180 by this analysis.

TABLE 13

Change in PWT at day 90 and day 180 in subjects whose PWT increased by ≧ 2 minutes at day 90.

|  | Placebo | Single | Double | Any FGF |
|---|---|---|---|---|
| Day 90 | N = 14 | N = 27 | N = 16 | N = 43 |
| Relative Change in PWT | 62.1% | 85.8% | 68.4% | 79.0% |
| Pair-wise P-value |  | .17 | .76 | .27 |
| Mean Change in PWT (min) | 3.67 | 4.28 | 5.37 | 4.68 |
| (+/−SD) | (1.57) | (2.54) | (4.10) | (3.20) |
| Overall P value = .35 |  |  |  |  |
| Day 180 | N = 14 | N = 26 | N = 16 | N = 42 |
| Relative Change in PWT | 55.3% | 86.0% | 53.2% | 72.7% |
| Pair-wise P-value |  | .17 | .90 | .37 |
| Mean Change in PWT (min) | 3.02 | 4.28 | 4.16 | 4.24 |
| (+/−SD) | (2.39) | (3.85) | (3.31) | (3.61) |
| Overall P value = .24 |  |  |  |  |

TABLE 14

Change in PWT at day 90 and day 180 in subjects whose PWT increased by <2 minutes at day 90.

|  | Placebo | Single | Double | Any FGF |
|---|---|---|---|---|
| Day 90 | N = 44 | N = 35 | N = 38 | N = 73 |

TABLE 14-continued

Change in PWT at day 90 and day 180 in subjects whose
PWT increased by <2 minutes at day 90.

|  | Placebo | Single | Double | Any FGF |
|---|---|---|---|---|
| Relative Change in PWT | 3.8% | 4.4% | 3.9% | 4.1% |
| Pair-wise P-value |  | .93 | .99 | .95 |
| Mean Change in PWT (min) | −.02 | .12 | .07 | .09 |
| (+/−SD) | (1.78) | (1.33) | (1.04) | (1.18) |
| Overall P value = 1.00 |  |  |  |  |
| Day 180 | N = 40 | N = 35 | N = 37 | N = 72 |
| Relative Change in PWT | 14.5% | −5.8% | 2.5% | −1.4% |
| Pair-wise P-value |  | .079 | .31 | .11 |
| Mean Change in PWT (min) | 1.20 | 0.16 | 0.44 | 0.31 |
| (+/−SD) | (2.71) | (2.62) | (1.84) | (2.24) |
| Overall P value = .21 |  |  |  |  |

Post-hoc Analysis of Anklebrachial Index

The initial analysis plan pre-specified that subjects having a baseline ankle brachial index (ABI) >1.2 (consistent with non-compressible artery) be excluded from the analysis (see FIG. 9). In a post-hoc analysis of the data, subjects having an ABI>1.2 at anytime (i.e., baseline, day 90, a As seen in FIG. 14, this post-hoc analysis indicates that both the single-dose and double-dose groups had a statistically significant improvement in ABI compared to the placebo group at day 90. This significance was not apparent at day 180, though the trend persisted for both the single-dose and double-dose groups.

Efficacy Summary

Primary Efficacy Analysis

The overall P-value for the primary efficacy analysis (change in PWT at 90 days) was 0.075 (ANOVA). The overall P-value for the secondary efficacy analysis by ANOVA of Ranks was statistically significant (P-value=0.034). The single-dose group demonstrated a 33.5% increase in PWT at day 90 versus a 20.3% increase in the double-dose group and a 13.8% increase in the placebo group. Pair-wise comparison of single-dose versus placebo was statistically significant (P-value=0.026). This treatment effect was not maintained at day 180 using the log-transformed data.

Secondary Efficacy Variables

Secondary efficacy variables showed no difference in PWT at day 180, no difference in COT at days 90 or 180, a favorable trend in ABI in FGF-treated groups with a statistically significant change in the double-dose group at day 180, and no difference in calf plethysmography. Interpretation of changes in the WIQ was confounded by imbalances at baseline. There was a trend towards improvement in the PCSS of the SF-36 in the single-dose group compared to placebo at day 90; this trend was driven by a statistically significant difference in body-pain score.

In the pre-specified subgroups, the effect of smoking was the most interesting. The overall P-value for change in PWT at day 90 was 0.007 for non-current smokers whereas it was 0.93 for current smokers. The change in PWT in the placebo group was 5.5% for non-current smokers and 29.3% for current smokers. Regression modeling suggests that smoking is a confounding variable (see post-hoc regression analysis below). The over-representation of current smokers in the placebo group (38%, versus 24% in the single-dose group and 21% in the double-dose group) made it more difficult to detect the difference in all evaluable subjects.

Changes in PWT in non-diabetics paralleled changes seen in all evaluable subjects at days 90 and 180. Change in PWT in diabetics paralleled changes seen in all evaluable subjects at day 90 but not at day 180. Regression modeling did not suggest that diabetes was a covariate. Changes in PWT in subjects over the median age (>68 years) were less than those in subjects under the median age at days 90 and 180. Regression modeling did not suggest that age was a covariate.

The post-hoc responder analysis shows a higher percentage of responders in the single-dose group and a greater magnitude of effect in the single-dose group. In addition, it suggests that the treatment effect persists at 180 days. The strongest predictor of response at 180 days is the response at 90 days.

Post-hoc Regression Analysis of Peak Walking Time

Regression models were used to evaluate the criteria underlying the use of absolute change score, relative change score, and PWT at day 90 (PWT90) as analysis variables. The models are discussed below. This post-hoc analysis reveals that both absolute and relative change scores have shortcomings and do not provide the most value for assessing FGF treatment effect in the phase II clinical trial. Using PWT90 as the analysis variable and adjusting for baseline PWT appears to provide a better basis, and value, for assessing the treatment effect of FGF.

Background—Assumptions in the Analysis:

I. Assume absolute change score is the correct variable to be used in the analysis. For each subject, the absolute day 90 change score in PWT $$= (PWT \text{ Day } 90 - PWT \text{ Baseline}) \text{ or}$$

$$= (PWT90 - PWTB).$$

Figure 15:
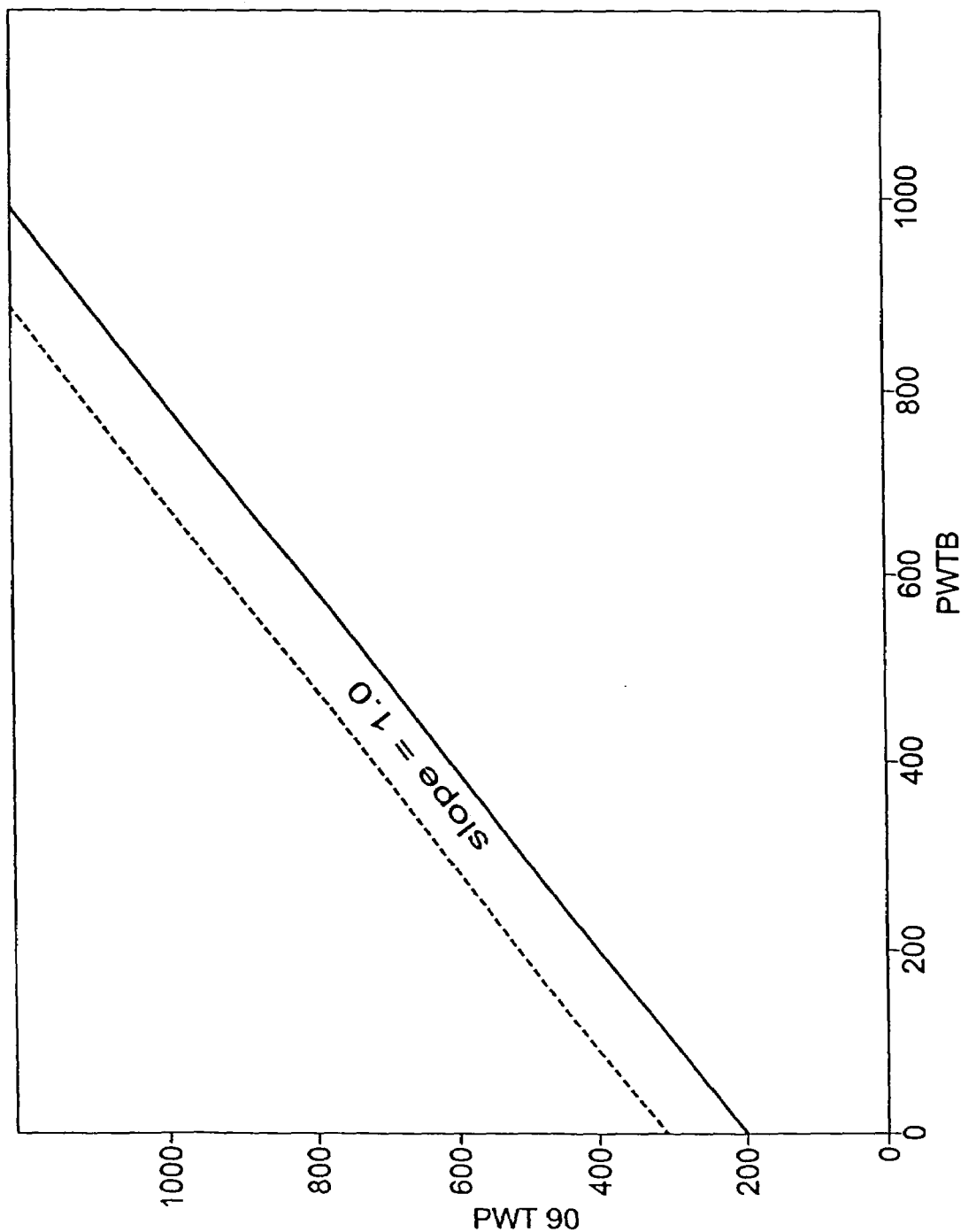
FIG. 15 shows a hypothetical plot of peak walking time at day 90 (PWT90) versus peak walking time at baseline (PWTB) when absolute change score is assumed to be the correct analysis variable. Assumptions: (PWT90−PWTB) =d, then PWT90=1.0*PWTB+d PWT90, scatter plot is linear, slope=1.0, and intercept is d (unrestricted).

Assuming that (PWT90−PWTB)=d, then PWT90=1.0*PWTB+d, (across the full range of PWTB), and the scatter plot of PWT90 versus PWTB would be:
1. Linear,
2. Slope=1.0, and
3. Intercept would be d (unrestricted).
FIG. 15 shows a hypothetical plot of PWT90 versus PWTB when absolute change score is assumed to be the correct variable.

II. Assume relative change score is the correct variable to be used in the analysis. For each subject, the relative day 90 change score in PWT $$=(PWT90/PWTB).$$

Figure 16:
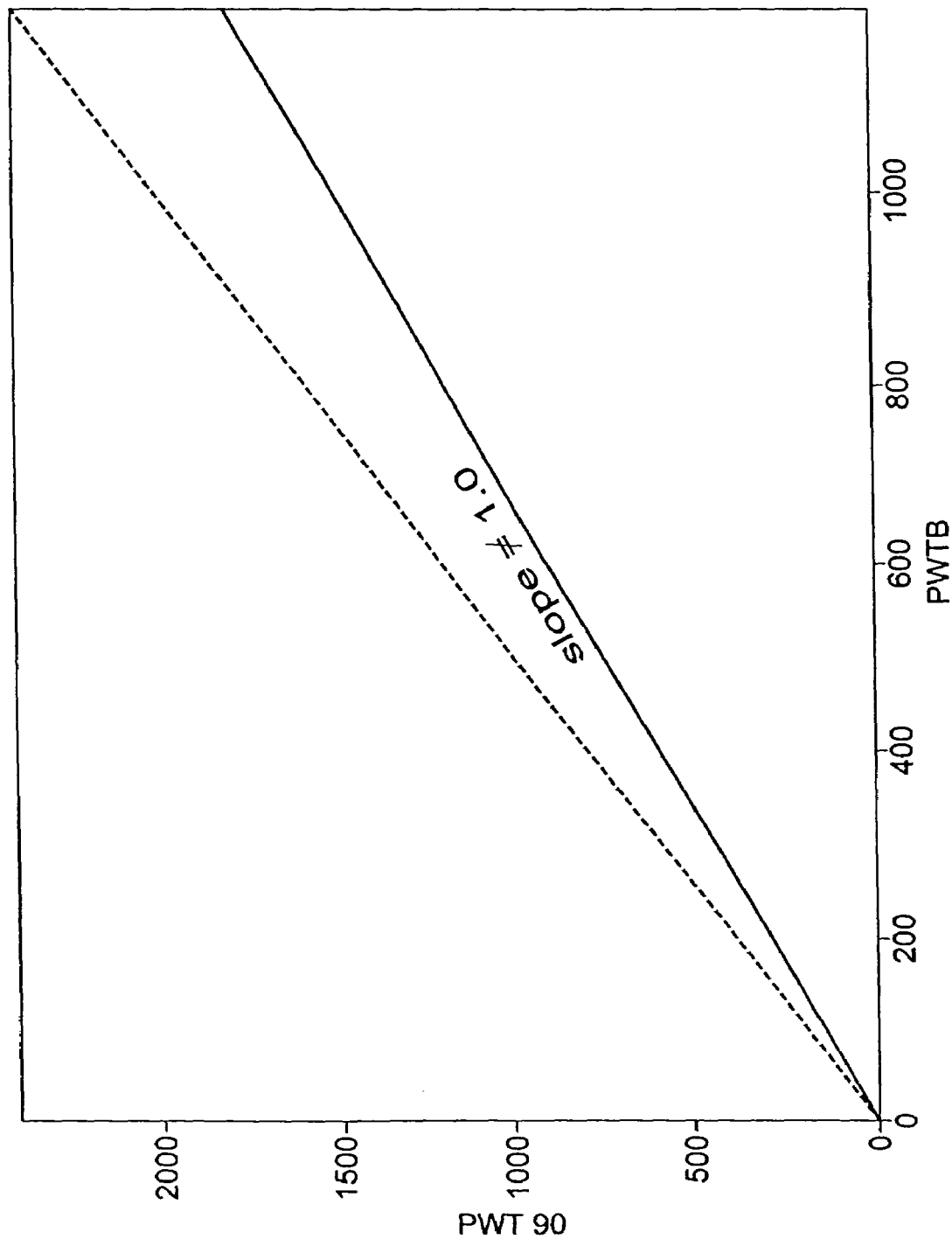
FIG. 16 shows a hypothetical plot of PWT90 versus PWTB when relative change score is assumed to be the correct analysis variable. Assumptions: (PWT90/PWTB) =1d, then PWT90=1d*PWTB+0.0 (across the full range of PWTB), scatter plot is linear, slope is 1d (unrestricted), and intercept is 0.0.

Assuming that (PWT90/PWTB)=1d, then PWT90=1d*PWTB+0.0 (across the full range of PWTB), and the scatter plot of PWT90 versus PWTB would be:
1. Linear,
2. Slope would be ld (unrestricted), and
3. Intercept would be 0.0.
FIG. 16 shows a hypothetical plot of PWT90 versus PWTB when relative change score is assumed correct.

The original analysis plan used absolute change score as the analysis variable, because there was not strong initial guidance from PIs/consultants to use relative score, and the absolute change score was used in the analysis of a related study directed to treatment of coronary artery disease (CAD). There was interest in a potential for a combined indication of FGF for CAD and PAD, which would be facilitated by consistent use of the same analysis variable. However, the analysis plan was amended to use the Log 10 relative change score (Log 10(PWT90/PWTB)=(Log 10 PWT90−Log 10 PWTB)), as a blinded preliminary evaluation of the skewness and kurtosis of the change score indicated the day 90 data did not appear to be symmetric. The day 180 PWT absolute change score appeared (in a post-hoc analysis) to be more nearly symmetric, i.e., the absolute change score appeared to have better distributional properties.

Results

Figure 17:
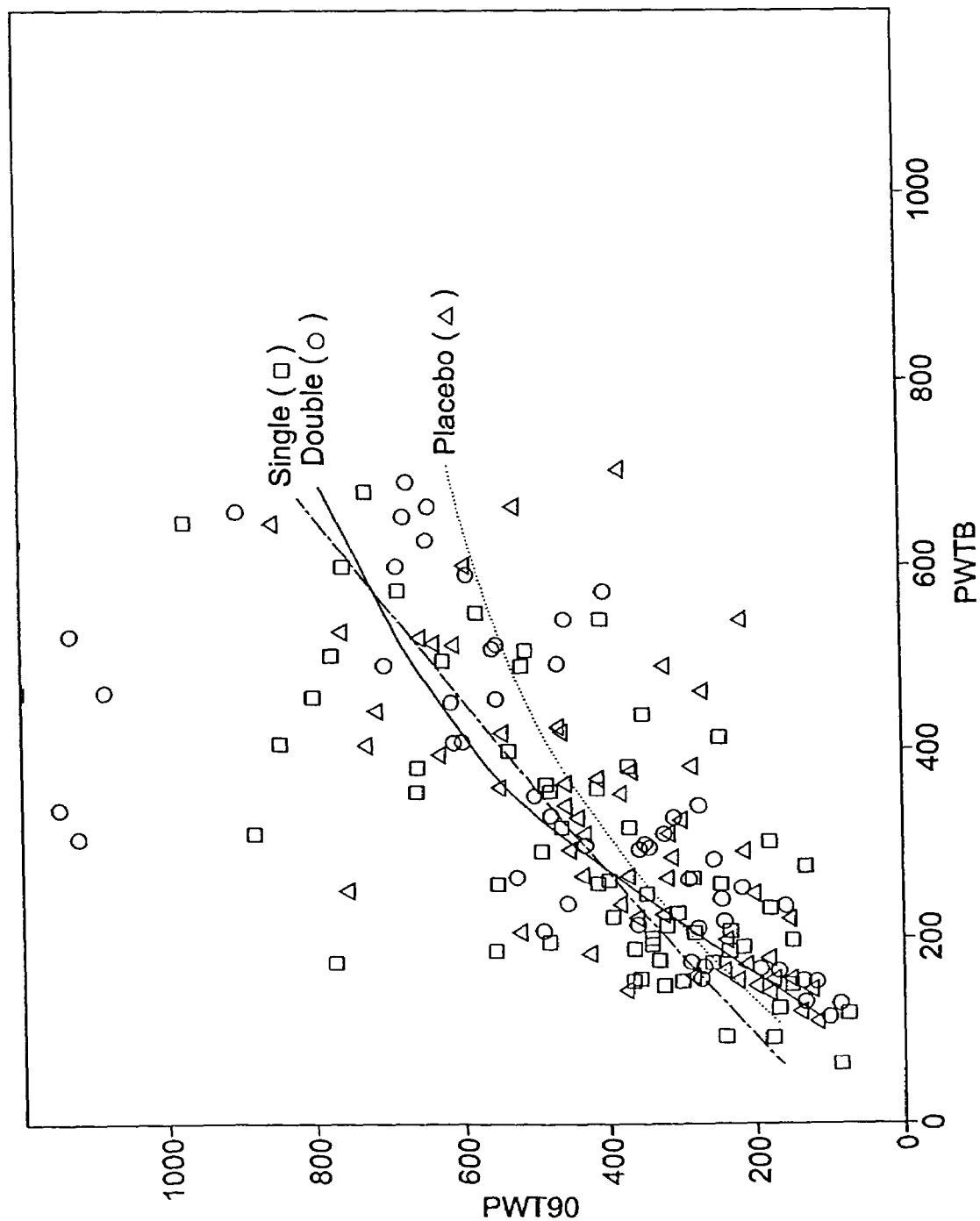
FIG. 17 shows a scatter plot of PWT90 versus PWTB plus an unrestricted spline regression curve for the placebo (Δ), single-dose (□), and double-dose (○) groups.
Figure 18:
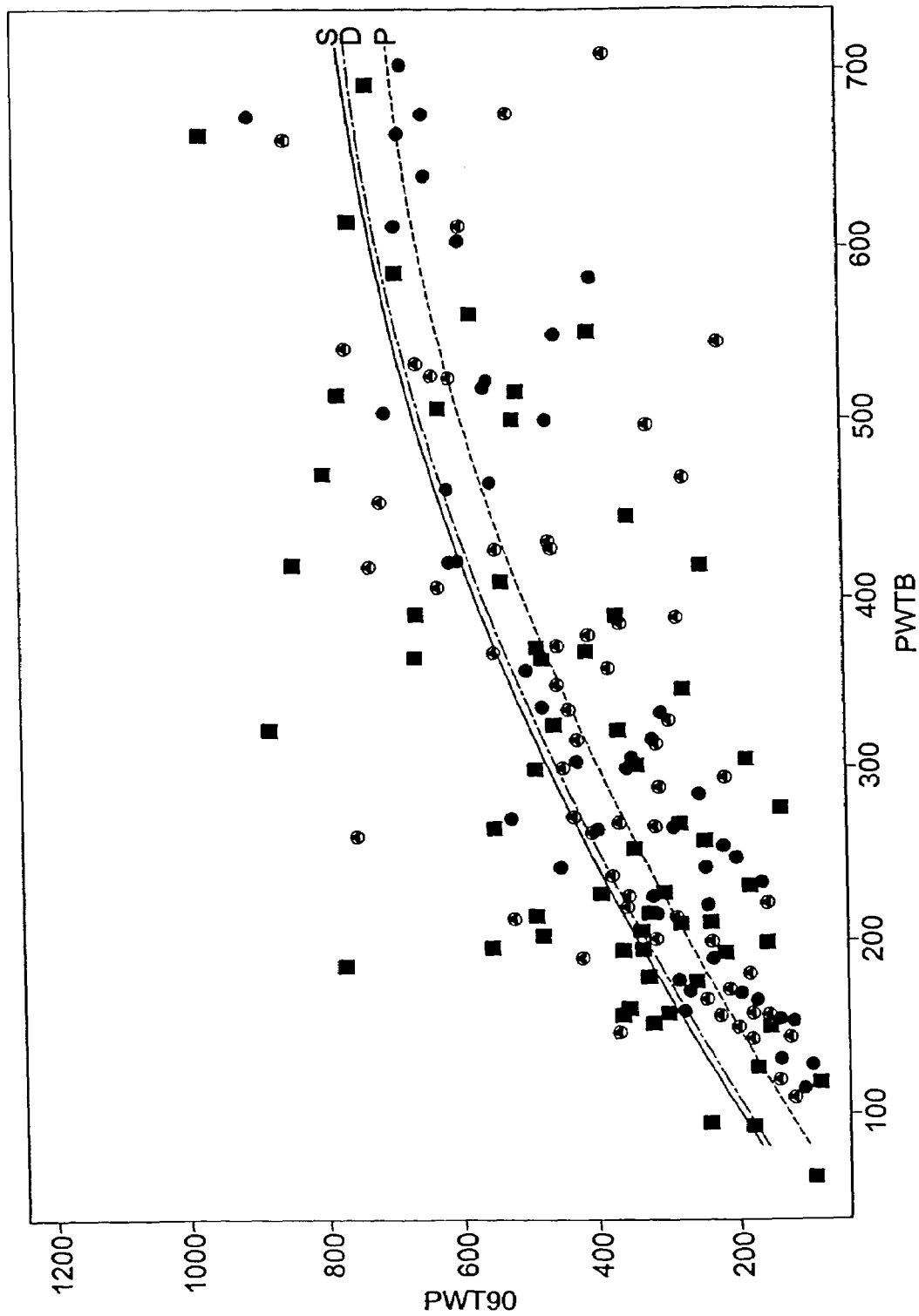
FIG. 18 shows the same scatter plot from FIG. 16 plus curves representing regression model 2 described in Table 15 as applied to the placebo (Δ), single-dose (□), and double-dose (○) groups. P=placebo; S=single-dose; D=double-dose.
Figure 19:
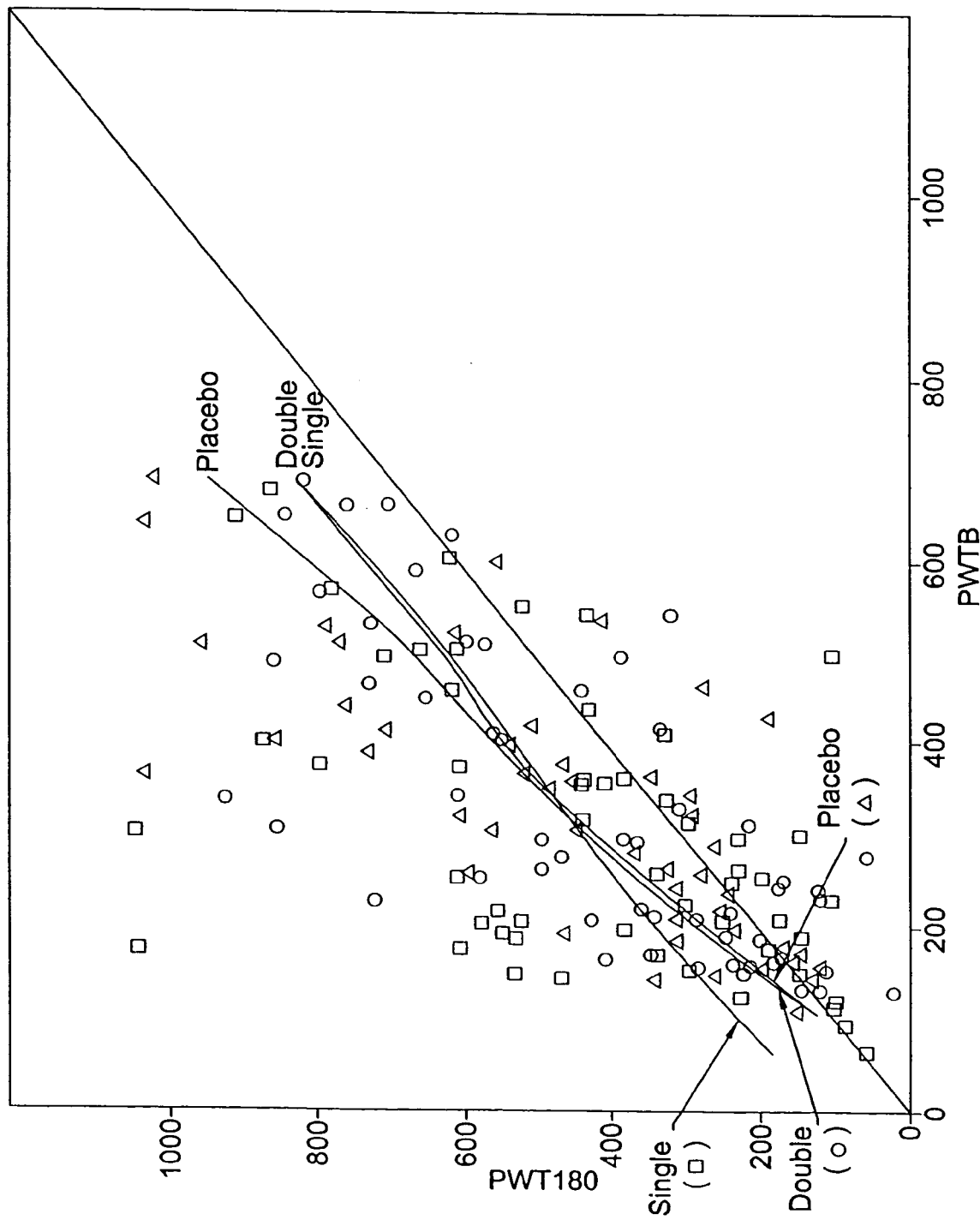
FIG. 19 shows the scatter plot of PWT180 versus PWTB plus an unrestricted spline regression curve for the placebo (Δ), single-dose (□), and double-dose (○) groups.

The results of the post-hoc regression analysis using the models described in Tables 15 and 16 are shown in FIGS. 17–19. FIG. 17 shows a scatter plot of PWT90 versus PWTB plus an unrestricted spline regression curve for each treatment group. FIG. 17 suggests that the first two criteria for use of absolute change score (linearity and slope=1) are not fully satisfied, and the criteria for use of relative change score (linearity and intercept=0.0) are also not satisfied. Thus, use of absolute change score or relative change score as the analysis variable does not appear to be fully consistent with the observed data.

FIG. 18 shows the same scatter plot plus curves representing regression model 2 described below. Regression models provide a more flexible method for assessing the change in PWT at day 90 and adjusting for baseline PWT. The curved shape of the scatter plot suggests that a regression model that produces curves will better represent or fit the study data. To achieve a curved shape, regression models would have PWT90 as the analysis variable, and predictor variables that include PWTB and (PWTB)$^2$. Other baseline variables such as smoking status can also be included in the regression model, if they are important confounders.

Table 15 shows three regression models with PWT90 as the analysis variable and adjusted for PWTB. All models also are adjusted for center (site). Model 1 for PWT90 includes only the predictor variable PWTB but is more flexible than using the absolute change score because model 1 can have any slope (i.e., model 1 does not require the slope to be 1.0). Model 1 better fits the data than either the absolute or relative change scores.

Model 2 for PWT90 includes both PWTB and (PWTB)$^2$ as predictor variables, and accommodates the curve shape of the scatter plot (see FIG. 18). Model 2 appears to provide a better fit to the study data than model 1, as seen by:

1) a p-value=0.027 for the inclusion of PWTB$^2$ in the model, and
2) an increased R$^2$=0.52 compared to model 1, which represents a statistically significant improvement in R$^2$ (p=0.025).

Model 3 for PWT90 includes smoking status (at baseline), PWTB, and (PWTB)$^2$, and adjusts for current smoking status.

TABLE 15

Regression models for PWT90. All regression models are adjusted for Center (Site).

| | 1 | 2 | 3 |
|---|---|---|---|
| Variables in Model | Trt. Single<br>Trt. Double<br>PWTB<br>(straight lines) | Trt. Single<br>Trt. Double<br>PWTB<br>PWTB$^2$<br>(curves) | Trt. Single<br>Trt. Double<br>PWTB<br>PWTB$^2$<br>Smoker<br>(curves) |
| Variable Coefficients | Single: 69.8<br>Double: 56.7<br>PWTB: 0.986 | Single: 71.5<br>Double: 61.8<br>PWTB: 1.917<br>PWTB$^2$: −0.0012 | Single: 79.3<br>Double: 71.5<br>PWTB: 1.93<br>PWTB$^2$: −0.0012<br>Smoker: −23.8 |
| p-value for each variable | Single: 0.032<br>Double: 0.096<br>PWTB: <0.0001 | Single: 0.027<br>Double: 0.067<br>PWTB: <0.0001<br>PWTB$^2$: 0.026 | Single: 0.015<br>Double: 0.037<br>PWTB: <0.0001<br>PWTB$^2$: 0.022<br>Smoker: 0.14 |
| Trt. Effect (seconds) | | | |
| S - Placebo | 69.8 | 71.5 | 79.3 |
| D - Placebo | 56.7 | 61.8 | 71.5 |
| Model R$^2$ | 0.50 | 0.52 | 0.53 |
| Estimated Placebo value for PWT90 when PWTB equals | | | Non-Smk / Smk |
| 100 sec. | 139 sec. | 75 | 33 / 57 |
| 300 sec. | 336 sec. | 363 | 323 / 347 |
| 600 sec. | 632 sec. | 615 | 578 / 602 |

The three regression models with PWT90 suggest:

The single-dose group had a statistically significant improvement in PWT at day 90, with pairwise p-values of 0.032, 0.027, and 0.015 (for models 1, 2, and 3, respectively).

The single-dose group had an average increase in PWT over the placebo group of 69.8, 71.7, and 79.3 seconds.

The double-dose group had a trend or statistically significant improvement in PWT at day 90, with pairwise p-values of 0.096, 0.0678, and 0.037.

The double-dose group had an average increase in PWT over the placebo group of 56.7, 61.8, and 71.5 seconds; and thus the double-dose group is more similar to the single-dose group in increased PWT than to the placebo group.

The regression models explain 50% or more of the variation in PWT at day 90.

FIG. 19 shows the scatter plot of PWT180 versus PWTB plus an unrestricted spline regression curve for each treatment group. The shape of the data also do not support a slope of 1 or an intercept of 0.0. The shape of the day 180 PWT data are only slightly curved.

Table 16 shows the three regression models for PWT180 as the analysis variable and adjusted for PWTB, and other baseline subject characteristics. All three models indicate similar results, with the single-dose group having a 22- to 26-second benefit over the placebo group, and the double-dose group apparently not different than the placebo group.

TABLE 16

Regression models for PWT180. All regression models are adjusted for Center (Site).

| | 1 | 2 | 3 |
|---|---|---|---|
| Variables in Model | Trt. Single<br>Trt. Double<br>PWTB<br>(straight lines) | Trt. Single<br>Trt. Double<br>PWTB<br>PWTB$^2$<br>(curves) | Trt. Single<br>Trt. Double<br>PWTB<br>PWTB$^2$<br>Smoker<br>(curves) |
| Variable Coefficients | Single: 22.3<br>Double: −7.4<br>PWTB: 1.2 | Single: 22.7<br>Double: −5.8<br>PWTB: 1.4<br>PWTB$^2$: −0.003 | Single: 25.9<br>Double: −1.7<br>PWTB: 1.4<br>PWTB$^2$: −0.0003<br>Smoker: −11.4 |
| p-value for each variable | Single: 0.514<br>Double: 0.836<br>PWTB: <0.0001 | Single: 0.506<br>Double: 0.872<br>PWTB: 0.0031<br>PWTB$^2$: 0.630 | Single: 0.454<br>Double: 0.964<br>PWTB: 0.0029<br>PWTB$^2$: 0.608<br>Smoker: 0.508 |
| Trt. Effect (seconds) | | | |
| S - Placebo | 22.3 | 22.7 | 25.9 | |
| D - Placebo | −7.4 | −5.8 | −1.7 | |
| Model R$^2$ | 0.57 | 0.57 | 0.57 | |
| Estimated Placebo value for PWT90 when PWTB equals | | | Non-Smk | Smk |
| 100 sec. | 157 | 141 | 123 | 134 |
| 300 sec. | 393 | 395 | 381 | 392 |
| 600 sec. | 745 | 731 | 723 | 734 |

In summary, the post-hoc regression analysis using the PWT at day 90 as the outcome variable and adjusting for PWT at baseline showed an increase of about 70 seconds (1.16 minutes) over placebo in the single-dose group, and about 57 seconds (0.95 minutes) in the double-dose group (p=0.032, 0.096, respectively). Allowing the relationship to be non-linear (i.e., curved) increased the treatment effect to about 72 seconds (1.19 minutes) in the single-dose group, and about 62 seconds (1.03 minutes) in the double-dose group (p=0.027, 0.067, respectively). Adjusting for smoking status further increased the treatment effect to about 79 seconds (1.32 minutes) in the single-dose group, and about 72 seconds (1.19 minutes) in the double-dose group (p=0.015, 0.035, respectively).

Conclusions from Phase II Clinical Trial

This study defined an effective dose, route, and regimen for treatment of PAD with rFGF-2. A single-dose of 30 μg/kg rFGF-2 given intra-arterially improved PWT of PAD patients. Administering a double-dose of rFGF-2 was not better than administering a single-dose of FGF-2. The magnitude of benefit in PWT was greater than 1 minute, with the duration of benefit observed at both 3 and 6 months. In fact, about 40% of the patients receiving the single-dose treatment experienced an increase in PWT of greater than 2 minutes at both day 90 and day 180, compared with only about 22% of patients receiving placebo and about 26% of patients receiving a double dose of rFGF-2. The data indicated that those patients who responded at Day 90 were more likely to respond at Day 180.

Thus, repeated dosing with rFGF-2 is feasible where necessary without compromising patient safety. The beneficial effect on PWT seen at both day 90 and day 180 with a single dose of rFGF-2 coupled with the safety of multiple dosing offers a method for providing prolonged therapeutic benefit to PAD patients. This can be achieved, for example, by administering to a patient a therapeutically effective dose at day 1, and subsequent therapeutically effective doses as clinically needed, i.e., as symptoms recur.

Example 3

Phase III PAD Clinical Trial

A phase III, multicenter (up to 50 sites), double-blind, placebo-controlled, dose-optimization study is conducted. The primary objective of this trial is to evaluate safety and efficacy of an intra-arterial (IA) infusion of 3.0 μg/kg or 30.0 μg/kg rFGF-2 versus placebo in peripheral artery disease (PAD) subjects with moderate to severe claudication. The trial enrolls 450 subjects (150 per arm) with moderate to severe claudication limiting exercise. Inclusion criteria and exclusion criteria are shown in Table 17. Sample size may be adjusted based on DSMB evaluation of variability of peak walking time at 90 days after 225 subjects are enrolled.

TABLE 17

Synopsis of Phase III Clinical Trial.

| Inclusion Criteria | Male or female ≧ 40 years of age<br>History of moderate to severe claudication limiting exercise for > 6 months<br>ABI > 0.3 and < 0.8 in the index limb at rest or > 20% decrease after exercise<br>Peripheral angiogram (contrast or MRA) within 4 months confirming > 70% obstruction of one or more infra-inguinal vessels, patent femoral inflow bilaterally, and absence of hemodynamically significant supra-inguinal obstruction<br>Able to exercise > 1 minute but < 12 minutes on two Gardner treadmill exercise tests. Exercise time must be limited by claudication at baseline. Duplicate tests will be performed > 24 hours but not > 2 weeks apart. The difference between baseline exercise times must be ≦ 20% of their mean.<br>Medically stable for 3 months with laboratory parameters within clinically acceptable range for required procedures.<br>Serum creatinine ≦ 2.2 mg/dL and urine protein/creatinine ratio < .3<br>Willing and able to give written informed consent |
|---|---|
| Exclusion Criteria | Peripheral Artery Disease<br><br>History of rest pain, non-healing ulcer, or gangrene within 3 months<br>Evidence of hemodynamically significant aorto-iliac obstructive disease<br>Peripheral revascularization (PTI or surgery) within 3 months |

TABLE 17-continued

Synopsis of Phase III Clinical Trial.

Malignancy

History of malignancy within past 5 years (exceptions: curatively treated basal cell carcinoma, squamous cell carcinoma of the skin in sun-exposed areas, or carcinoma of the cervix)
Evidence or suspicion of malignancy after screening according to ACS guidelines Ocular conditions Proliferative retinopathy or moderate or severe non-proliferative retinopathy
Maculopathy with choroidal neovascularization or macular edema
Intra-ocular surgery within 3 months Cardiovascular conditions Myocardial infarction, CABG, PTCA within 3 months
Transient ischemic attack or stroke within 3 months General medical conditions:

Pregnancy, nursing mothers
Participation in clinical trials of other investigational agents, intra-arterial devices, or procedures, for which follow-up visits have not been completed
History of organ transplantation
Any combined condition which makes the subject unsuitable for participation in the opinion of the Investigator, e.g., concurrent medical illness which limits life expectancy to < 12 months, psychosis, severe mental retardation, inability to communicate with study personnel, drug or alcohol abuse
Diagnosis of primary pulmonary hypertension, restrictive or obstructive cardiomyopathy, active vasculitis
Previous participation in any therapeutic angiogenesis trial with any investigational agent unless subject received placebo The study drug, rFGF-2 having the sequence shown in FIG. 2 (SEQ ID NO:2), is contained at 0.35 or 3.5 mg/mL in a lyophilized powder, to be reconstituted with normal saline; it is formulated in 10 mM sodium citrate, 1 mM EDTA, 10 mM dithiothreitol (DTT), 4% glycine, 1% glucose at pH 6.0. Treatment consists of infusion of 20 mL at 1 mL/min of placebo, 3.0 µg/kg or 30.0 µg/kg rFGF-2, divided equally between two legs, via the common femoral artery. Assignment to treatments is randomized 1:1:1 placebo: 3.0 µg/kg rFGF-2:30.0 µg/kg rFGF-2. Blood will be drawn at baseline and at the end of the infusion for analysis of plasma concentration of FGF-2. Each subject is observed in the hospital for 6 hours following study drug administration and followed as an outpatient at specified intervals for 180 days.

Patients are monitored for acute safety variables including systolic hypotension associated with IA infusion and any evidence of allergic reactions, as well as frequency and severity of adverse events, changes in laboratory parameters (especially urine protein), evidence of retinal toxicity, and evidence of seroconversion (antibody formation). DSMB will review SAEs and abnormal laboratory tests during enrollment.

Primary efficacy variable is change from baseline in peak walking time (PWT) at 90 days as measured by Gardner graded exercise test time, adjusted for baseline PWT, smoking status, and center. Secondary efficacy is established based on the following parameters:

Change from baseline in PWT at 45, 135, and 180 days adjusted for baseline PWT, smoking status, and center;

Change from baseline in claudication onset time (COT) at 45, 90, 135, and 180 days;

Change from baseline in anklebrachial index pressure (ABI) at 45, 90, 135, and 180 days;

Change from baseline in severity of claudication, distance, speed, and stair climbing scores of the WIQ at 45, 90, 135, and 180 days;

Change from baseline in physical component summary score (PCSS) of the SF-36 at 45, 90, 135, and 180 days; and Percentage of responders at 90 and 180 days.

Potential substudies include plethysmography, muscle biopsy, and MR spectroscopy. General protocol and information tests at follow-up visits are shown in Table 18.

TABLE 18

General Schedule of Events.

| Tests | Screen DAY −45 to −1 | Dosing DAY 1 | DAY 15 | DAY 45 | Primary Endpoint DAY 90 | DAY 135 | Termination DAY 180 |
|---|---|---|---|---|---|---|---|
| Complete History and Physical Exam consistent with ACS guidelines | X | | | | | | |
| Limited History and | | X | X | X | X | X | X |

TABLE 18-continued

General Schedule of Events.

| Tests | Screen DAY −45 to −1 | Dosing DAY 1 | DAY 15 | DAY 45 | Primary Endpoint DAY 90 | DAY 135 | Termination DAY 180 |
|---|---|---|---|---|---|---|---|
| Physical Exam Telephone FU | | | X | | | | |
| 12-lead ECG | X | X | | | X | | X |
| Chest x-ray | X | | | | | | |
| PSA (males only); serum pregnancy (females only); screen for HIV, hepatitis and drugs of abuse if appropriate | X | | | | | | |
| Laboratory Tests (CBC, platelets, chemistry[1], urine[2]) | X | X | X | X | X | X | X |
| FGF-2 Antibodies | | X | X | X | X | X | X |
| Gardner graded exercise test for PWT and COT; ABIs | X, X | | | X | X | X | X |
| Ophthalmologic exam; fundus photography only if evidence of retinopathy | X | | | | | | X |
| Quality of Life: WIQ, SF-36 | X | | | X | X | X | X |
| Limited Angiogram | | X | | | | | |
| Study Drug Administration | | X | | | | | |
| Blood Sample for FGF-2 and Infusion Solution Sample | | X | | | | | |
| Concomitant Medications | X | X | X | X | X | X | X |
| Adverse events (AEs) | | X | X | X | X | X | X |

[1]CBC (no differential), platelets, electrolytes, BUN, creatinine, cholesterol, liver enzymes, glucose, cotinine
[2]Urine for specific gravity, qualitative protein, protein/creatinine ratio Statistical Analysis Data are analyzed with an intent to treat analysis using ANOVA of Ranks with last value after baseline carried forward for missing data, or lowest rank for subjects without a post-baseline PWT assessment, adjusting for baseline PWT, smoking status, and center.

Example 4

Influence of FGF-2 Dosing Regimens on Collateral Blood Flow in Rats With Peripheral Arterial Insufficiency A study was undertaken to compare the efficacy of three routes of FGF-2 administration (intra-arterial [positive control], intramuscular, and a route used in humans) to increase collateral blood in rats with experimental peripheral arterial insufficiency.

Previous animal model studies have demonstrated that bFGF is effective at improving collateral blood flow to the distal calf muscles following bilateral femoral artery occlusion (Yang et al. (1996) Circ. Res. 79:62–69; Yang and Feng (2000) Am. J. Physiol. 278:H85–H93). The improved blood flow from ~50 ml/min/100 g to 70–80 ml/min/100 g was possible due to a significant decrease in vascular resistance of the collateral vessels of the upper thigh. The increase in collateral blood flow to the calf muscles correlates well with an angiographic score obtained from x-ray images of the thigh arterial tree. Upper thigh collateral vessels are the major site of resistance in the circuit following occlusion of the femoral arteries (Yang et al. (1996) Circ. Res. 79:62–69). It is not likely that de novo synthesis of new capillaries (angiogenesis) could develop into large conduit vessels and account for this vascular response. Rather, the extent of the resistance change and the short time for vascular development to occur (16 days) makes it probable that enlargement of existing vessels was the primary change contributing to the greater blood flow. This increase in collateral blood flow with bFGF is also found in aged rats (Yang and Feng (2000) Am. J. Physiol. 278:H85–H93) and enhanced with physical activity (Yang et al. (1998) Am. J. Physiol. 274: H2053–H2061).

A variety of routes and regimens of bFGF administration have been shown effective at increasing collateral blood flow in animal models. These include close-arterial systemic, and subcutaneous routes with bolus, short-term and relatively long-term delivery regimens achieved by injections or timed infusions with osmotic pumps (Yang and Feng (2000) Am. J. Physiol. 278:H85–H93). While these protocols have been useful to demonstrate the efficacy of bFGF, some of these regimens are not appropriate for patient management in therapeutic angiogenesis. Further, the value of repeated administration of bFGF at timed intervals in patients is expected, but not feasible with many of the procedures used in previous experimental studies. For example, it would be extremely valuable to establish the efficacy of intramuscular injections of bFGF. However, it is presently unclear whether direct intramuscular injections of bFGF impart targeted or generalized improvement in collateral blood flow. Thus, the purpose of the present pilot study was to evaluate the efficacy of FGF-2 administration via intramuscular injections and a clinically relevant protocol used in therapeutic angiogenesis.

Experimental Design:

Animals with peripheral arterial insufficiency were divided into four groups:

| Group 1 | Intra-arterial, 14 day continuous infusion, FGF-2 (5 μg/kg/day) | | N = 6 |
|---|---|---|---|
| Group 2 | Vehicle group comprised of: | | |
| | group 2a | 14 day intra-arterial continuous infusion of vehicle | N = 2 |
| | group 2b | Single intra-arterial injection of vehicle | N = 2 |
| | group 2c | Intramuscular, single bolus of vehicle | N = 4 |
| Group 3 | Single Intra-arterial Injection | | |
| | group 3a | Dose 1 (1.5 μg/kg total) | N = 6 |
| | group 3b | Dose 2 (15 μg/kg total) | N = 6 |
| | group 3c | Dose 3 (30 μg/kg total) | N = 6 |
| Group 4 | Intramuscular Injection | | |
| | group 4a | Dose 1 (0.15 μg/kg total) | N = 6 |
| | group 4b | Dose 2 (1.5 μg/kg total) | N = 6 |
| | group 4c | Dose 3 (15 μg/kg total) | N = 6 |

Because of distinct delivery routes, the study was not performed in a completely blinded manner. However, animals within a delivery route received the treatments of dose (i.e., vehicle, infusion, dose 1, dose 2, or dose 3) in a randomly-assigned blinded manner.

General Protocol:

Adult Sprague-Dawley rats (approximately 325 g) were conditioned to the treadmill by walking for 5–10 min twice daily for 5 days. To initiate the experiment, the animals were subjected to bilateral femoral artery occlusion (cf. Methods). On the same day, animals began a two-week treatment according to the treatment groups described above. On day 16 of the experiment, collateral-dependent blood was determined while the rats were running on a motor-driven treadmill. Following completion of the data set, the results were pooled according to treatment group, and the results were analyzed statistically by ANOVA. It was expected that vehicle-treated animals from each of the delivery routes could be grouped into one reference control group. However, data were assessed to determine whether the intramuscular injection treatment had introduced. a systematic response, for example, caused by an inflammatory response in the muscle.

Peripheral Arterial Insufficiency Model:

Bilateral ligation of the femoral artery is designed to establish peripheral arterial insufficiency without impairing resting muscle blood flow. The high blood flow reserve of muscle is markedly reduced while residual muscle blood flow is sufficient to support resting blood flow needs; e.g., compare (Yang et al. (1990) *J. Appl. Physiol* 69:1353–1359; Yang and Terjung (1993) *J. Appl, Physiol.* 75(1):452–457; Mackie and Terjung (1983) *Am. J. Physiol.* 245: H265–H275). Thus, there is no 'rest pain' nor complications leading to pathological changes, tissue necrosis, or gangrene observed with more proximal vascular obstructions (Chleboun and Martin (1994) *Aust. N. Z. J Surg.* 64:202–207). It is recognized that these surgically treated animals do not represent the broad spectrum of peripheral arterial insufficiency found clinically. Rather, this model is characteristic of large vessel occlusive disease that often presents itself with symptoms of intermittent claudication.

Methods:

Animal Care. Adult Sprague Dawley rats (approximately 325 g), obtained from Taconic Farms, Germantown, N.Y., were housed in a temperature controlled room (20±1° C.), with a 12 hr/12 hr light/dark cycle. Animals were given Purina Rat Chow and tap water ad libitum. Previous studies have established that a complete data set of approximately 12 animals per group is necessary to definitively evaluate treatment effects (Yang et al. (1990) *J. Appl. Physiol* 69:1353–1359). Thus, the present work was a pilot study to assess the general response for future consideration of the half of the study. Since ~90% of rats received from the supplier are willing runners (to be randomly assigned to treatment groups) and some attrition occurs in the conduct of the experiment, it was expected that n=5–6 per experimental group would be obtained.

FGF-2 Delivery. FGF-2 delivery was initiated/achieved at the time of femoral artery ligation by: a) a 14-day continuous intra-arterial infusion; b) a single intramuscular injection; or c) a single intra-arterial injection as follows.

For the positive control, a group of 8 rats received a 14-day infusion from an in-dwelling pump/catheter (rate=0.5 μL/hr). The catheter was placed such that the infusion was delivered upstream of the ligation point in the femoral artery of one hindlimb. Six of the rats received FGF-2 at a dose of 5 μg/kg/day for 14 days for a total of 70 μg/kg; the other two received vehicle alone (PBS). To allow for dead spaces, filling the pump, filling the tubing, etc., a final volume of 0.435 mL of pump solution for each rat was calculated based on the initial rat weight of approximately 325 g. A separate pump solution aliquot was prepared for each rat. Just prior to use, 43.5 μL of sodium citrate and 7 μL of glycerol was added to each aliquot, so that the volume of FGF-2 solution or PBS in each of the prepared tubes was 0.435−0.0435−0.007=0.385 mL. For the FGF aliquots, the concentration of FGF-2 was thus 152.5 μg/mL.

A second group of rats received vehicle or FGF-2 with a single intra-arterial injection. This injection was given over the span of 10 minutes, into the femoral artery of one hindlimb, upstream of the point of ligation. The volume to be injected was 0.35 mL. Six rats received 1.5 μg/kg FGF-2 total dose; six received 15 μg/kg FGF-2; six received 30 μg/kg FGF-2; and two received vehicle alone.

A third group of rats received a single intramuscular injection. This injection was split between two sites in the medial hamstring on one hindlimb, in the region of collateral formation. The volume to be injected was 100 μL per site, for a total volume of 0.2 mL. Six rats received 0.15 μg/kg FGF-2 total dose; six received 1.5 μg/kg FGF-2; six received 15 g/kg FGF-2; and four received vehicle alone.

Ligation Surgery. Under ether anesthesia each femoral artery was isolated just distal to the inguinal ligament. A ligature was placed tightly around the femoral vessel to assure total obstruction to blood flow. Topical antibiotic powder (Neo-Predef, Upjohn) was placed on the wound prior to closure with skin clips. The surgical procedure was brief, was achieved with a 100% success rate, and the animals recovered rapidly. As done routinely (Yang and Terjung(1993) *J. Appl, Physiol.* 75(1):452–457; Yang et al. (1995a) *Circ. Res.* 76.448–456; Yang et al. (1995b) *Am J. Physiol.* 268:H1174–H1180), visual inspection at the time of autopsy verified the success of surgery.

Blood Flow Determination during Treadmill Running In Vivo. Muscle blood flow was determined in a blinded manner, utilizing radiolabeled microspheres during treadmill running, as used extensively (Yang and Terjung(1993)

J. Appl, Physiol. 75(1):452–457; Mackie and Terjung (1983) Am. J. Physiol. 245:H265–H275; Mathien and Terjung (1986) Am. J. Physiol. 245:H1050–H1059; Mathien and Terjung (1990) Am J. Physiol. 258:H759–H765; Yang et al. (1990) J. Appl. Physiol 69:1353–1359; Yang et al. (1995) Circ. Res. 76.448–456; Yang et al. (1995) Am J. Physiol. 268:H1174–H1180; Yang et al. (1996) Circ. Res. 79:62–69). Microspheres (15 µm diameter), labeled with $^{85}$Sr or $^{141}$Ce (~10 mCi/g), were obtained commercially (NEN, Boston) in a suspension of 10% dextran containing 0.05% Tween 80. A well-mixed suspension of microspheres was carefully infused into the arch of the aorta, followed by a saline flush, over a 15–20 second period. Direct comparisons of injection sites (left ventricle versus aortic arch) gave the same blood flows to the kidneys and hindlimb muscles. Approximately 360,000 spheres were infused to establish an adequate microsphere distribution and to permit statistical assurance in the data (Mackie and Terjung (1983) Am. J. Physiol. 245:H265–H275; Mathien and Terjung (1986) Am. J. Physiol. 245:H1050–H1059; Mathien and Terjung (1990) Am J. Physiol. 258:H759–H765). Typically, there were well in excess of 400 microspheres per individual muscle sample during exercise. Withdrawal of the reference blood sample at 500 µl/min (Sage Instruments Model 355 pump) from the caudal artery was initiated 10 sec prior to infusion of microspheres and continued for approximately 100 sec. It has been found that reference blood samples, withdrawn from the right carotid artery, femoral artery, and caudal artery, match within 5–10% of each other (Mackie and Terjung (1983) Am. J. Physiol. 245:H265–H275; Unpub. Obs).

Two blood flow determinations were performed in each animal, at a moderate and higher treadmill speed, to establish peak vascular conductance of the muscle so that the upstream collateral resistance in the upper thigh becomes rate-determining for downstream blood flow to the calf muscles. This is achieved, since muscle contraction (exercise) is the most powerful stimulus for vasodilation. Following exercise, the rats were sacrificed by an overdose of pentobarbital and the tissue samples obtained as described below, and counted (LKB Universal Gamma Counter), with the reference blood sample, to a 1% counting error. Bilateral sections of kidney (middle 3rd) were taken to verify the adequacy of microsphere mixing. Appropriate corrections were made for background and isotopic spillover. Blood flows (ml/min/100 g) were calculated as follows:

$$FLOW = (CPM_T \times FLOW_{RBS} \times 100)/(CPM_{RBS} \times Wt_T)$$

where T is tissue and RBS is the reference blood sample.

Heart rate and arterial pressure were continuously monitored during exercise.

Surgical Procedures for Blood Flow Determination. Surgical preparation for in vivo blood flow determination was a modification of that described by Laughlin et al. (1982) J. Appl. Physiol 52:1629–1635. Animals were anesthetized with ketamine/ACE-promazine (100 mg/0.5 mg per kg) and a catheter was inserted into the right carotid artery to the arch of the aorta for later infusion of the microspheres. A catheter (PE 50 tapered) was also placed into the caudal artery for the withdrawal of blood sample. Both catheters were filled with saline containing heparin (100 IU/ml), led under the skin, and exteriorized at the back of the neck. Each incision site was sutured and covered with 1% xylocaine ointment (Astra Pharm.). Consistent with the experience of others (Gleeson and Baldwin (1981) J. Appl. Physiol. 50:1205–121 1), after 3–4 hr following placement of the catheters the rats were alert, willing to run, and exhibited normal exercise tolerance.

Muscle Sections. All tissues of the hindlimb from the hip socket distal, are dissected, weighed, and counted for radioactivity. Muscles (Greene (1963) Anatomy of the Rat, New York Hafner Pub. Co.) include: biceps femoris, semitendinosus, semimembranosus, caudofemoralis, adductor group, gluteus group, tensor fascias latae, quadriceps group, soleus, plantaris, gastrocnemius, tibialis anterior, extensor digitorurm longus, deep lateral and posterior crural muscles. The tibia, fibula, femur and foot are also weighed and counted. In addition, sections composed primarily of fast-twitch red fibers (deep lateral quadriceps and deep lateral gastrocnemius), fast-twitch white fibers (superficial quadriceps and superficial medial gastrocnemius), and slow-twitch red fibers (soleus) are obtained. A thorough biochemical, physiological and morphological characterization of these muscle fiber sections is known (cf. Saltin and Gollaick (1983) In: Handbook of Physiology—Skeletal Muscle, Am. Physiol. Soc., pp. 555–631). Blood flow to the diaphragm will also be determined to follow the response of an active muscle that is not subject to ligation.

Statistical Procedures. Statistical evaluation employing repeated measures analysis of variance, Tukey's comparison of means, and a t-test were performed as appropriate (Steel and Torrie (1960) Principles & Procedures of Statistics, McGraw-Hill, New York).

Figure 20:
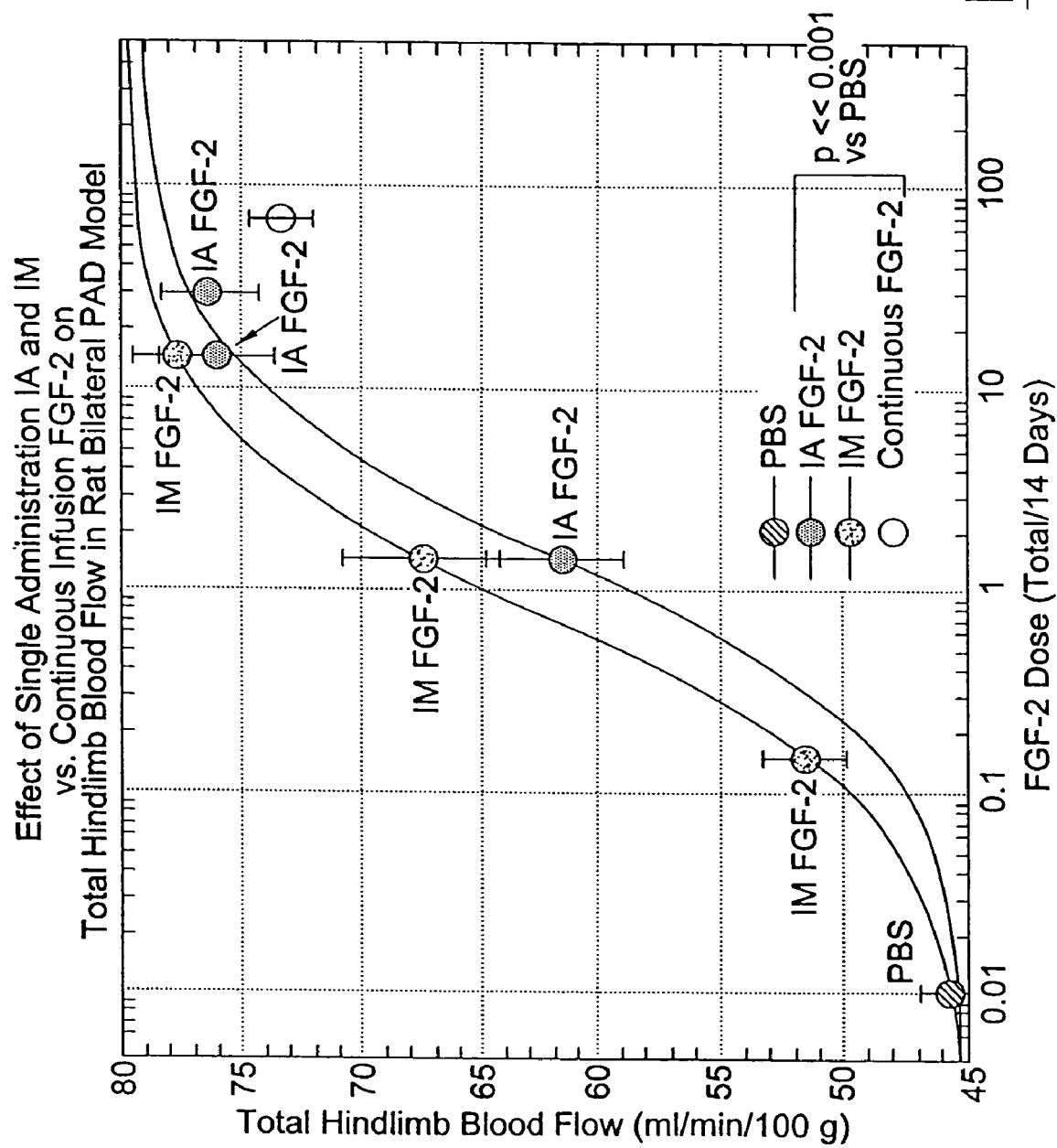
FIG. 20 shows the effect of single administration by intra-arterial infusion (IA) or intramuscular injection (IM) and 14-day continuous intra-arterial infusion on total hindlimb blood flow in a rat bilateral PAD model. Phosphate-buffered solution (PBS) served as the vehicle control.

Results:

Intramuscular administration of rFGF-2 increased blood flow in a dose-dependent manner (FIG. 20). When administered intra-arterially, the 15 µg/kg rFGF-2 dose was just as efficacious as the 30 µg/kg dose. Continuous infusion over a 14-day period did not provide a significantly different efficacy relative to the single IA infusion or single IM injection mode of administration.

These data demonstrate efficacy of single IM injection and single IA infusion of rFGF-2 in enhancing blood flow to the hindlimb quarters in a PAD animal model.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiment.

What is claimed is:

1. A method for treating peripheral artery disease in a patient, said method comprising administering to said patient a therapeutically effective amount of a fibroblast growth factor-2 (FGF-2) or an angiogenically active fragment or angiogenically active mutein thereof, wherein said therapeutically effective amount of said FGF-2 or said angiogenically active fragment or angiogenically active mutein thereof is divided into two doses and a single dose is administered into each leg of said patient within a one hour period, whereby said peripheral artery disease is treated, wherein said FGF-2 comprises the sequence set forth in SEQ ID NO:2, SEQ ID NO:4, SEQ ID NO:6, or SEQ ID NO:8, and wherein said angiogenically active mutein has at least 95% amino acid sequence identity to the FGF-2 sequence set forth in SEQ ID NO:2, SEQ ID NO:4, SEQ ID NO:6, or SEQ ID NO:8.

2. The method of claim 1, wherein said FGF-2 or said angiogenically active fragment or angiogenically active mutein thereof is a recombinant molecule.

3. The method of claim 1, wherein said mutein comprises an FGF-2 molecule wherein at least one constituent cysteine residue is replaced by a neutral amino acid.

4. The method of claim 3, wherein the neutral amino acid is serine or threonine.

5. The method of claim 1, wherein said FGF-2 or said angiogenically active fragment or angiogenically active mutein thereof is administered simultaneously with another molecule selected from the group consisting of heparin, other proteoglycan.

6. The method of claim 5, wherein said heparin is a low molecular weight molecule.

7. The method of claim 5, wherein said heparin is unfractionated heparin.

8. The method of claim 1, wherein said FGF-2 or said angiogenically active mutein thereof is administered within about 5 minutes to about 60 minutes of heparin or other proteoglycan administration to said patient.

9. The method of claim 8, wherein said FGF-2 or said angiogenically active fragment or angiogenically active mutein thereof is administered within about 20 minutes to about 30 minutes of heparin or heparin or other proteoglycan administration to said patient.

10. The method of claim 1, wherein said FGF-2 or said angiogenically active fragment or angiogenically active mutein thereof is administered in the absence of administering a molecule selected from the group consisting of heparin and other proteoglycans.

11. The method of claim 1, wherein said therapeutically effective amount of FGF-2 or said angiogenically active fragment or angiogenically active mutein thereof is administered to said patient once in a 24 hour period.

12. The method of claim 1, wherein said therapeutically effective amount of said FGF-2 or said angiogenically active fragment or angiogenically active mutein thereof is administered to said patient once a week.

13. The method of claim 1, wherein said therapeutically effective amount of FGF-2 or said angiogenically active fragment or angiogenically active mutein thereof is administered to said patient once a month, once every 2 months, once every 3 months, once every four months, once every five months, or once every six months.

14. The method of claim 1, wherein said therapeutically effective amount of said FGF-2 or said angiogenically active mutein thereof is administered as an adjunct to vascular surgery, mechanical bypass surgery, angioplasty, or angiogram.

15. The method of claim 1, wherein said therapeutically effective amount of said FGF-2 or said angiogenically active fragment or angiogenically active mutein thereof is about 0.1 µg/kg to about 1 µg/kg.

16. The method of claim 1, wherein said therapeutically effective amount of said FGF-2 or said angiogenically active fragment or angiogenically active mutein thereof is about 1 µg/kg to about 3 µg/kg.

17. The method of claim 1, wherein said therapeutically effective amount of said FGF-2 or said angiogenically active fragment or angiogenically active mutein thereof is about 3 µg/kg to about 5 µg/kg.

18. The method of claim 1, wherein said therapeutically effective amount of said FGF-2 or said angiogenically active fragment or angiogenically active mutein thereof is about 5 µg/kg to about 7 µg/kg.

19. The method of claim 1, wherein said therapeutically effective amount of said FGF-2 or said angiogenically active fragment or angiogenically active mutein thereof is about 7 µg/kg to about 9 µg/kg.

20. The method of claim 1, wherein said therapeutically effective amount of said FGF-2 or said angiogenically active fragment or angiogenically active mutein thereof is about 9 µg/kg to about 10 µg/kg.

21. The method of claim 1, wherein said therapeutically effective amount of said FGF-2 or said angiogenically active fragment or angiogenically active mutein thereof is about 10 µg/kg to about 15 µg/kg.

22. The method of claim 1, wherein said therapeutically effective amount of said FGF-2 or said angiogenically active fragment or angiogenically active mutein thereof is about 15 µg/kg to about 20 µg/kg.

23. The method of claim 1, wherein said therapeutically effective amount of said FGF-2 or said angiogenically active fragment or angiogenically active mutein thereof is about 20 µg/kg to about 25 µg/kg.

24. The method of claim 1, wherein said therapeutically effective amount of said FGF-2 or said angiogenically active fragment or angiogenically active mutein thereof is about 25 µg/kg to about 30 µg/kg.

25. The method of claim 1, wherein said therapeutically effective amount of said FGF-2 or said angiogenically active fragment or angiogenically active mutein thereof is about 30 µg/kg to about 40 µg/kg.

26. The method of claim 1, wherein said therapeutically effective amount of said FGF-2 or said angiogenically active fragment or angiogenically active mutein thereof is about 40 µg/kg to about 50 µg/kg.

27. The method of claim 1, wherein said therapeutically effective amount of said FGF-2 or said angiogenically active fragment or angiogenically active mutein thereof is about 4 µg to about 0.3 mg.

28. The method of claim 1, wherein said therapeutically effective amount of said FGF-2 or said angiogenically active fragment or angiogenically active mutein thereof is about 1.0 mg to about 2.0 mg.

29. The method of claim 28, wherein said therapeutically effective amount of said FGF-2 or said angiogenically active fragment or angiogenically active mutein thereof is about 1.0 to about 2.0 mg.

30. The method of claim 28, wherein said therapeutically effective amount of said FGF-2 or said angiogenically active fragment or angiogenically active mutein thereof is about 2.0 to about 3.5 mg.

31. The method of claim 1, wherein said FGF-2 or said angiogenically active fragment or angiogenically active mutein thereof is administered to said patient by intraarterial (IA) or intravenous (IV) infusion.

32. The method of claim 1, wherein said FGF-2 or said angiogenically active fragment or angiogenically active mutein thereof is administered to said patient by one or more intramuscular (IM) injections.

33. The method of claim 1, wherein said FGF-2 or said angiogenically active fragment or angiogenically active mutein thereof is administered to said patient by subcutaneous (SC) injection.

34. The method of claim 1, wherein said administering of said FGF-2 or said angiogenically active fragment or angiogenically active mutein thereof provides an improvement in peak walking time (PWT) in said patient relative to PWT in the absence of said administering of FGF-2 or said angiogenically active fragment or angiogenically active mutein thereof.

35. The method of claim 1, wherein said administering of FGF-2 or said angiogenically active fragment or angiogenically active mutein thereof provides an improvement in anklebrachial index (ABI) in said patient relative to ABI in the absence of said administering of FGF-2 or said angiogenically active fragment or angiogenically active mutein thereof.

36. The method of claim 1, wherein said administering of FGF-2 or said angiogenically active fragment or angiogenically active mutein thereof results in a reduction in body pain.

37. The method of claim 1, wherein said administering of FGF-2 or said angiogenically active fragment or angiogenically active mutein thereof improves stair climbing ability.

38. The method of claim 1, wherein said administering of FGF-2 or said angiogenically active fragment or angiogenically active mutein thereof reduces the severity of claudication.

39. A method for treating peripheral artery disease in a patient, said method comprising administering to said patient a therapeutically effective amount of fibroblast growth factor-2 (FGF-2) or an angiogenically active fragment or angiogenically active mutein thereof, wherein said therapeutically effective amount is about 0.1 µg/kg to about 9.9 µg/kg, wherein said therapeutically effective amount of FGF-2 is divided into two doses and a single dose is administered into each leg of said patient within a one hour period, whereby said peripheral artery disease is treated, wherein said FGF-2 comprises the sequence set forth in SEQ ID NO:2, SEQ ID NO:4, SEQ ID NO:6, or SEQ ID NO:8, and wherein said angiogenically active mutein has at least 95% amino acid sequence identity to the FGF-2 sequence set forth in SEQ ID NO:2, SEQ ID NO:4, SEQ ID NO:6, or SEQ ID NO:8.

40. The method of claim 39, wherein said therapeutically effective amount of FGF-2 or said angiogenically active fragment or angiogenically active mutein thereof is administered as part of a pharmaceutical composition.

41. The method of claim 40, wherein said pharmaceutical composition is a stabilized FGF-2-DTT formulation.

42. The method of claim 39, wherein said FGF-2 or said angiogenically active fragment or angiogenically active mutein thereof is administered simultaneously with another molecule selected from the group consisting of heparin and other proteoglycan.

43. The method of claim 39, wherein said therapeutically effective amount of said FGF-2 or said angiogenically active fragment or angiogenically active mutein thereof is about 0.1 µg/kg to about 1 µg/kg.

44. The method of claim 39, wherein said therapeutically effective amount of said FGF-2 or said angiogenically active fragment or angiogenically active mutein thereof is about 1 µg/kg to about 3 µg/kg.

45. The method of claim 39, wherein said therapeutically effective amount of said FGF-2 or said angiogenically active fragment or angiogenically active mutein thereof is about 3 µg/kg to about 5 µg/kg.

46. The method of claim 39, wherein said therapeutically effective amount of said FGF-2 or said angiogenically active fragment or angiogenically active mutein thereof is about 5 µg/kg to about 7 µg/kg.

47. The method of claim 39, wherein said therapeutically effective amount of said FGF-2 or said angiogenically active fragment or angiogenically active mutein thereof is about 7 µg/kg to about 8 µg/kg.

48. The method of claim 39, wherein said therapeutically effective amount of said FGF-2 or said angiogenically active fragment or angiogenically active mutein thereof is about 8 µg/kg to about 9 µg/kg.

49. The method of claim 39, wherein said therapeutically effective amount of said FGF-2 or said angiogenically active fragment or angiogenically active mutein thereof is about 9 µg/kg to about 9.9 µg/kg.

50. The method of claim 39, wherein said therapeutically effective amount of said FGF-2 or said angiogenically active fragment or angiogenically active mutein thereof is about 7.0 µg to about 0.7 mg.

51. The method of claim 50, wherein said therapeutically effective amount of said FGF-2 or said angiogenically active fragment or angiogenically active mutein thereof is about 9.0 µg to about 0.5 mg.

52. The method of claim 51, wherein said therapeutically effective amount of said FGF-2 or said angiogenically active fragment or angiogenically active mutein thereof is about 0.1 mg to about 0.4 mg.

53. The method of claim 52, wherein said therapeutically effective amount of said FGF-2 or said angiogenically active fragment or angiogenically active mutein thereof is about 0.1 mg to about 0.2 mg.

54. The method of claim 39, wherein said FGF-2 or said angiogenically active fragment or angiogenically active mutein thereof is administered to said patient by intra-arterial (IA) or intravenous (IV) infusion.

55. The method of claim 39, wherein said FGF-2 or said angiogenically active mutein thereof is administered to said patient by one or more intramuscular (IM) injections.

56. A method for improving peak walking time in a patient with intermittent claudication, said method comprising administering to said patient a therapeutically effective amount of a fibroblast growth factor-2 or an angiogenically active fragment or angiogenically active mutein thereof, wherein said therapeutically effective amount of said FGF-2 or said angiogenically active fragment or angiogenically active mutein thereof is divided into two doses and a single dose is administered into each leg of said patient within a one hour period, whereby said peak walking time is improved, wherein said FGF-2 comprises the sequence set forth in SEQ ID NO:2, SEQ ID NO;4, SEQ ID NO:6, or SEQ ID NO:8, and wherein said angiogenically active mutein has at least 95% amino acid sequence identity to the FGF-2sequence set forth in SEQ ID NO:2, SEQ ID NO:4, SEQ ID NO:6, or SEQ ID NO:8.

57. The method of claim 56, wherein said therapeutically effective amount of said FGF-2 or said angiogenically active fragment or angiogenically active mutein thereof is about 0.1 µg/kg to about 1 µg/kg.

58. The method of claim 56, wherein said therapeutically effective amount of said FGF-2 or said angiogenically active fragment or angiogenically active mutein thereof is about 1 µg/kg to about 3 µg/kg.

59. The method of claim 56, wherein said therapeutically effective amount of said FGF-2 or said angiogenically active fragment or angiogenically active mutein thereof is about 3 µg/kg to about 5 µg/kg.

60. The method of claim 56, wherein said therapeutically effective amount of said FGF-2 or said angiogenically active fragment or angiogenically active mutein thereof is about 5 µg/kg to about 9 µg/kg.

61. The method of claim 56, wherein said therapeutically effective amount of said FGF-2 or said angiogenically active fragment or angiogenically active mutein thereof is about 9 µg/kg to about 10 µg/kg.

62. The method of claim 56, wherein said therapeutically effective amount of said FGF-2 or said angiogenically active fragment or angiogenically active mutein thereof is about 10 µg/kg to about 20 µg/kg.

63. The method of claim 56, wherein said therapeutically effective amount of said FGF-2 or said angiogenically active fragment or angiogenically active mutein thereof is about 20 µg/kg to about 30 µg/kg.

64. A method for improving ankle-brachial index in a patient with intermittent claudication, said method comprising administering to said patient a therapeutically effective amount of a fibroblast growth factor-2(FGF-2) or an angiogenically active fragment or angiogenically active mutein thereof, wherein said therapeutically effective amount of said FGF-2 or said angiogenically active fragment or angiogenically active mutein thereof is divided into two doses and a single dose is administered into each leg of said patient within a one hour period, whereby said ankle-brachial index is improved, wherein said FGF-2comprises the sequence set forth in SEQ ID NO:2, SEQ ID NO:4, SEQ ID NO:6, or SEQ ID NO:8, and wherein said angiogenically active mutein has at least 95% amino acid sequence identity to the FGF-2 sequence set forth in SEQ ID NO:2, SEQ ID NO:4, SEQ ID NO:6, or SEQ ID NO:8.

65. The method of claim 64, wherein said therapeutically effective amount of said FGF-2 or said angiogenically active fragment or angiogenically active mutein thereof is about 0.1 µg/kg to about 1 µg/kg.

66. The method of claim 64, wherein said therapeutically effective amount of said FGF-2 or said angiogenically active fragment or angiogenically active mutein thereof is about 1 µg/kg to about 3 µg/kg.

67. The method of claim 64, wherein said therapeutically effective amount of said FGF-2 or said angiogenically active fragment or angiogenically active mutein thereof is about 3 µg/kg to about 5 µg/kg.

68. The method of claim 64, wherein said therapeutically effective amount of said FGF-2 or said angiogenically active fragment or angiogenically active mutein thereof is about 5 µg/kg to about 9 µg/kg.

69. The method of claim 64, wherein said therapeutically effective amount of said FGF-2 or said angiogenically active fragment or angiogenically active mutein thereof is about 9 µg/kg to about 10 µg/kg.

70. The method of claim 64, wherein said therapeutically effective amount of said FGF-2 or said angiogenically active fragment or angiogenically active mutein thereof is about 10 µg/kg to about 20 µg/kg.

71. The method of claim 64, wherein said therapeutically effective amount of said FGF-2 or said angiogenically active fragment or angiogenically active mutein thereof is about 20 µg/kg to about 30 µg/kg.

72. The method of claim 31, wherein said FGF-2 or said angiogenically active fragment or angiogenically active mutein thereof is administered by intra-arterial infusion (IA) into at least one artery of each leg of said patient.

73. The method of claim 72, wherein said FGF-2 or said angiogenically active fragment or angiogenically active mutein thereof is administered into the common femoral artery of each leg of said patient.

74. The method of claim 73, wherein said FGF-2 or said angiogenically active fragment or angiogenically active mutein thereof is administered via bilateral delivery using a catheter.

75. The method of claim 73, wherein said FGF-2 or said angiogenically active fragment or angiogenically active mutein thereof is administered via direct IA infusion into the common femoral artery of each leg of said patient.

76. The method of claim 1, wherein said peripheral artery disease is evidenced by claudication.

77. The method of claim 76, wherein said patient has critical limb ischemia.

* * * * *

SEQUENCE LISTING

<160> NUMBER OF SEQ ID NOS: 9

<210> SEQ ID NO 1
<211> LENGTH: 441
<212> TYPE: DNA
<213> ORGANISM: Bos taurus
<220> FEATURE:
<221> NAME/KEY: CDS
<222> LOCATION: (1)...(441)

<400> SEQUENCE: 1

```
cca gcc cta cca gaa gat ggg ggg tcc ggg gcc ttc cca cca ggg cac      48
Pro Ala Leu Pro Glu Asp Gly Gly Ser Gly Ala Phe Pro Pro Gly His
1               5                   10                  15 ttc aaa gat cca aaa cga cta tat tgt aaa aac ggg ggg ttc ttc cta      96
Phe Lys Asp Pro Lys Arg Leu Tyr Cys Lys Asn Gly Gly Phe Phe Leu
            20                  25                  30 cga atc cac cca gat ggg cga gta gat ggg gta cga gaa aaa tcc gat     144
Arg Ile His Pro Asp Gly Arg Val Asp Gly Val Arg Glu Lys Ser Asp
        35                  40                  45 cca cac atc aaa cta caa cta caa gcc gaa gaa cga ggg gta gta tcc     192
Pro His Ile Lys Leu Gln Leu Gln Ala Glu Glu Arg Gly Val Val Ser
    50                  55                  60 atc aaa ggg gta tgt gcc aac cga tat cta gcc atg aaa gaa gat ggg     240
Ile Lys Gly Val Cys Ala Asn Arg Tyr Leu Ala Met Lys Glu Asp Gly
65                  70                  75                  80 cga cta cta gcc tcc aaa tgt gta acc gat gaa tgt ttc ttc ttc gaa     288
Arg Leu Leu Ala Ser Lys Cys Val Thr Asp Glu Cys Phe Phe Phe Glu
                85                  90                  95 cga cta gaa tcc aac aac tat aac acc tat cga tcc cga aaa tat tcc     336
Arg Leu Glu Ser Asn Asn Tyr Asn Thr Tyr Arg Ser Arg Lys Tyr Ser
            100                 105                 110 tcc tgg tat gta gcc cta aaa cga acc ggg caa tat aaa cta ggg cca     384
Ser Trp Tyr Val Ala Leu Lys Arg Thr Gly Gln Tyr Lys Leu Gly Pro
        115                 120                 125 aaa acc ggg cca ggg caa aaa gcc atc cta ttc cta cca atg tcc gcc     432
Lys Thr Gly Pro Gly Gln Lys Ala Ile Leu Phe Leu Pro Met Ser Ala
    130                 135                 140 aaa tcc taa                                                         441
Lys Ser *
145
```

<210> SEQ ID NO 2
<211> LENGTH: 146
<212> TYPE: PRT
<213> ORGANISM: Bos taurus

<400> SEQUENCE: 2

```
Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
```

```
                        85                  90                  95
Arg Leu Glu Ser Asn Asn Tyr Asn Thr Tyr Arg Ser Arg Lys Tyr Ser
            100                 105                 110

Ser Trp Tyr Val Ala Leu Lys Arg Thr Gly Gln Tyr Lys Leu Gly Pro
        115                 120                 125

Lys Thr Gly Pro Gly Gln Lys Ala Ile Leu Phe Leu Pro Met Ser Ala
    130                 135                 140

Lys Ser
145

<210> SEQ ID NO 3
<211> LENGTH: 441
<212> TYPE: DNA
<213> ORGANISM: Homo sapiens
<220> FEATURE:
<221> NAME/KEY: CDS
<222> LOCATION: (1)...(441)

<400> SEQUENCE: 3 ccc gcc ttg ccc gag gat ggc ggc agc ggc gcc ttc ccg ccc ggc cac      48
Pro Ala Leu Pro Glu Asp Gly Gly Ser Gly Ala Phe Pro Pro Gly His
 1               5                  10                  15 ttc aag gac ccc aag cgg ctg tac tgc aaa aac ggg ggc ttc ttc ctg      96
Phe Lys Asp Pro Lys Arg Leu Tyr Cys Lys Asn Gly Gly Phe Phe Leu
            20                  25                  30 cgc atc cac ccc gac ggc cga gtt gac ggg gtc cgg gag aag agc gac     144
Arg Ile His Pro Asp Gly Arg Val Asp Gly Val Arg Glu Lys Ser Asp
        35                  40                  45 cct cac atc aag cta caa ctt caa gca gaa gag aga gga gtt gtg tct     192
Pro His Ile Lys Leu Gln Leu Gln Ala Glu Glu Arg Gly Val Val Ser
    50                  55                  60 atc aaa gga gtg tgt gct aac cgt tac ctg gct atg aag gaa gat gga     240
Ile Lys Gly Val Cys Ala Asn Arg Tyr Leu Ala Met Lys Glu Asp Gly
65                  70                  75                  80 aga tta ctg gct tct aaa tgt gtt acg gat gag tgt ttc ttt ttt gaa     288
Arg Leu Leu Ala Ser Lys Cys Val Thr Asp Glu Cys Phe Phe Phe Glu
                85                  90                  95 cga ttg gaa tct aat aac tac aat act tac cgg tca agg aaa tac acc     336
Arg Leu Glu Ser Asn Asn Tyr Asn Thr Tyr Arg Ser Arg Lys Tyr Thr
            100                 105                 110 agt tgg tat gtg gca ctg aaa cga act ggg cag tat aaa ctt gga tcc     384
Ser Trp Tyr Val Ala Leu Lys Arg Thr Gly Gln Tyr Lys Leu Gly Ser
        115                 120                 125 aaa aca gga cct ggg cag aaa gct ata ctt ttt ctt cca atg tct gct     432
Lys Thr Gly Pro Gly Gln Lys Ala Ile Leu Phe Leu Pro Met Ser Ala
    130                 135                 140 aag agc tga                                                         441
Lys Ser *
145

<210> SEQ ID NO 4
<211> LENGTH: 146
<212> TYPE: PRT
<213> ORGANISM: Homo sapiens

<400> SEQUENCE: 4

Pro Ala Leu Pro Glu Asp Gly Gly Ser Gly Ala Phe Pro Pro Gly His
 1               5                  10                  15

Phe Lys Asp Pro Lys Arg Leu Tyr Cys Lys Asn Gly Gly Phe Phe Leu
            20                  25                  30
```

```
Arg Ile His Pro Asp Gly Arg Val Asp Gly Val Arg Glu Lys Ser Asp
         35                  40                  45

Pro His Ile Lys Leu Gln Leu Gln Ala Glu Glu Arg Gly Val Val Ser
         50                  55                  60

Ile Lys Gly Val Cys Ala Asn Arg Tyr Leu Ala Met Lys Glu Asp Gly
 65                  70                  75                  80

Arg Leu Leu Ala Ser Lys Cys Val Thr Asp Glu Cys Phe Phe Phe Glu
                 85                  90                  95

Arg Leu Glu Ser Asn Asn Tyr Asn Thr Tyr Arg Ser Arg Lys Tyr Thr
                100                 105                 110

Ser Trp Tyr Val Ala Leu Lys Arg Thr Gly Gln Tyr Lys Leu Gly Ser
            115                 120                 125

Lys Thr Gly Pro Gly Gln Lys Ala Ile Leu Phe Leu Pro Met Ser Ala
        130                 135                 140

Lys Ser
145
```

<210> SEQ ID NO 5
<211> LENGTH: 468
<212> TYPE: DNA
<213> ORGANISM: Bos taurus
<220> FEATURE:
<221> NAME/KEY: CDS
<222> LOCATION: (1)...(468)

<400> SEQUENCE: 5

```
atg gca gcc ggg agc atc acc acg ctg cca gcc cta cca gaa gat ggg     48
Met Ala Ala Gly Ser Ile Thr Thr Leu Pro Ala Leu Pro Glu Asp Gly
 1               5                  10                  15 ggg tcc ggg gcc ttc cca cca ggg cac ttc aaa gat cca aaa cga cta     96
Gly Ser Gly Ala Phe Pro Pro Gly His Phe Lys Asp Pro Lys Arg Leu
             20                  25                  30 tat tgt aaa aac ggg ggg ttc ttc cta cga atc cac cca gat ggg cga    144
Tyr Cys Lys Asn Gly Gly Phe Phe Leu Arg Ile His Pro Asp Gly Arg
         35                  40                  45 gta gat ggg gta cga gaa aaa tcc gat cca cac atc aaa cta caa cta    192
Val Asp Gly Val Arg Glu Lys Ser Asp Pro His Ile Lys Leu Gln Leu
     50                  55                  60 caa gcc gaa gaa cga ggg gta gta tcc atc aaa ggg gta tgt gcc aac    240
Gln Ala Glu Glu Arg Gly Val Val Ser Ile Lys Gly Val Cys Ala Asn
 65                  70                  75                  80 cga tat cta gcc atg aaa gaa gat ggg cga cta cta gcc tcc aaa tgt    288
Arg Tyr Leu Ala Met Lys Glu Asp Gly Arg Leu Leu Ala Ser Lys Cys
                 85                  90                  95 gta acc gat gaa tgt ttc ttc ttc gaa cga cta gaa tcc aac aac tat    336
Val Thr Asp Glu Cys Phe Phe Phe Glu Arg Leu Glu Ser Asn Asn Tyr
            100                 105                 110 aac acc tat cga tcc cga aaa tat tcc tcc tgg tat gta gcc cta aaa    384
Asn Thr Tyr Arg Ser Arg Lys Tyr Ser Ser Trp Tyr Val Ala Leu Lys
        115                 120                 125 cga acc ggg caa tat aaa cta ggg cca aaa acc ggg cca ggg caa aaa    432
Arg Thr Gly Gln Tyr Lys Leu Gly Pro Lys Thr Gly Pro Gly Gln Lys
    130                 135                 140 gcc atc cta ttc cta cca atg tcc gcc aaa tcc taa                    468
Ala Ile Leu Phe Leu Pro Met Ser Ala Lys Ser *
145                 150                 155
```

<210> SEQ ID NO 6
<211> LENGTH: 155
<212> TYPE: PRT

<213> ORGANISM: Bos taurus

<400> SEQUENCE: 6

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
130                 135                 140

Ala Ile Leu Phe Leu Pro Met Ser Ala Lys Ser
145                 150                 155
```

<210> SEQ ID NO 7
<211> LENGTH: 474
<212> TYPE: DNA
<213> ORGANISM: Homo sapiens
<220> FEATURE:
<221> NAME/KEY: CDS
<222> LOCATION: (1)...(468)

<400> SEQUENCE: 7

```
atg gca gcc ggg agc atc acc acg ctg ccc gcc ttg ccc gag gat ggc      48
Met Ala Ala Gly Ser Ile Thr Thr Leu Pro Ala Leu Pro Glu Asp Gly
1               5                   10                  15 ggc agc ggc gcc ttc ccg ccc ggc cac ttc aag gac ccc aag cgg ctg      96
Gly Ser Gly Ala Phe Pro Pro Gly His Phe Lys Asp Pro Lys Arg Leu
            20                  25                  30 tac tgc aaa aac ggg ggc ttc ttc ctg cgc atc cac ccc gac ggc cga     144
Tyr Cys Lys Asn Gly Gly Phe Phe Leu Arg Ile His Pro Asp Gly Arg
        35                  40                  45 gtt gac ggg gtc cgg gag aag agc gac cct cac atc aag cta caa ctt     192
Val Asp Gly Val Arg Glu Lys Ser Asp Pro His Ile Lys Leu Gln Leu
50                  55                  60 caa gca gaa gag aga gga gtt gtg tct atc aaa gga gtg tgt gct aac     240
Gln Ala Glu Glu Arg Gly Val Val Ser Ile Lys Gly Val Cys Ala Asn
65                  70                  75                  80 cgt tac ctg gct atg aag gaa gat gga aga tta ctg gct tct aaa tgt     288
Arg Tyr Leu Ala Met Lys Glu Asp Gly Arg Leu Leu Ala Ser Lys Cys
                85                  90                  95 gtt acg gat gag tgt ttc ttt ttt gaa cga ttg gaa tct aat aac tac     336
Val Thr Asp Glu Cys Phe Phe Phe Glu Arg Leu Glu Ser Asn Asn Tyr
            100                 105                 110 aat act tac cgg tca agg aaa tac acc agt tgg tat gtg gca ctg aaa     384
Asn Thr Tyr Arg Ser Arg Lys Tyr Thr Ser Trp Tyr Val Ala Leu Lys
        115                 120                 125 cga act ggg cag tat aaa ctt gga tcc aaa aca gga cct ggg cag aaa     432
Arg Thr Gly Gln Tyr Lys Leu Gly Ser Lys Thr Gly Pro Gly Gln Lys
```

-continued

```
                130                 135                 140
gct ata ctt ttt ctt cca atg tct gct aag agc tga tttttaa                    474
Ala Ile Leu Phe Leu Pro Met Ser Ala Lys Ser *
145                 150                 155
```

<210> SEQ ID NO 8
<211> LENGTH: 155
<212> TYPE: PRT
<213> ORGANISM: Homo sapiens

<400> SEQUENCE: 8

```
Met Ala Ala Gly Ser Ile Thr Thr Leu Pro Ala Leu Pro Glu Asp Gly
  1               5                  10                  15

Gly Ser Gly Ala Phe Pro Pro Gly His Phe Lys Asp Pro Lys Arg Leu
                 20                  25                  30

Tyr Cys Lys Asn Gly Gly Phe Phe Leu Arg Ile His Pro Asp Gly Arg
             35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155
```

<210> SEQ ID NO 9
<211> LENGTH: 9
<212> TYPE: PRT
<213> ORGANISM: Bos taurus

<400> SEQUENCE: 9

```
Met Ala Ala Gly Ser Ile Thr Thr Leu
  1               5
```